(12) United States Patent
Scheible et al.

(10) Patent No.: US 11,629,126 B2
(45) Date of Patent: Apr. 18, 2023

(54) MATERIALS FOR ORGANIC ELECTROLUMINESCENT DEVICES

(71) Applicant: Merck Patent GmbH, Darmstadt (DE)

(72) Inventors: Katja Maria Scheible, Darmstadt (DE); Fabrice Eckes, Saint Louis (FR); Holger Heil, Frankfurt am Main (DE); Beate Burkhart, Darmstadt (DE); Dominik Joosten, Frankfurt am Main (DE); Elvira Montenegro, Weinheim (DE)

(73) Assignee: MERCK PATENT GMBH, Darmstadt (DE)

( * ) Notice: Subject to any disclaimer, the term of this patent is extended or adjusted under 35 U.S.C. 154(b) by 607 days.

(21) Appl. No.: 16/336,720

(22) PCT Filed: Oct. 2, 2017

(86) PCT No.: PCT/EP2017/074961
§ 371 (c)(1),
(2) Date: Mar. 26, 2019

(87) PCT Pub. No.: WO2018/065357
PCT Pub. Date: Apr. 12, 2018

(65) Prior Publication Data
US 2019/0225581 A1 Jul. 25, 2019

(30) Foreign Application Priority Data

Oct. 6, 2016 (EP) .................... 16192507

(51) Int. Cl.
| | | |
|---|---|---|
| *C07D 209/82* | (2006.01) | |
| *C07D 333/76* | (2006.01) | |
| *C07D 307/91* | (2006.01) | |
| *H01L 51/00* | (2006.01) | |
| *C07C 211/61* | (2006.01) | |
| *C07C 305/06* | (2006.01) | |
| *C07F 7/08* | (2006.01) | |
| *H01L 51/50* | (2006.01) | |

(52) U.S. Cl.
CPC .......... *C07D 209/82* (2013.01); *C07C 211/61* (2013.01); *C07C 305/06* (2013.01); *C07D 307/91* (2013.01); *C07D 333/76* (2013.01); *C07F 7/0816* (2013.01); *H01L 51/006* (2013.01); *H01L 51/0058* (2013.01); *H01L 51/0061* (2013.01); *H01L 51/0072* (2013.01); *H01L 51/0073* (2013.01); *H01L 51/0074* (2013.01); *H01L 51/0094* (2013.01); *C07C 2602/06* (2017.05); *C07C 2603/18* (2017.05); *C07C 2603/26* (2017.05); *H01L 51/0067* (2013.01); *H01L 51/0085* (2013.01); *H01L 51/50* (2013.01); *H01L 51/506* (2013.01); *H01L 51/5056* (2013.01); *Y02E 10/549* (2013.01)

(58) Field of Classification Search
CPC .............. C07C 211/61; C07C 2602/06; C07C 2603/18; C07C 2603/26; C07C 305/06; C07D 209/82; C07D 307/91; C07D 333/76; C07F 7/0816; H01L 51/0058; H01L 51/006; H01L 51/0061; H01L 51/0067; H01L 51/0072; H01L 51/0073; H01L 51/0074; H01L 51/0085; H01L 51/0094; H01L 51/50; H01L 51/5056; H01L 51/506
See application file for complete search history.

(56) References Cited

U.S. PATENT DOCUMENTS 5,518,824 A    5/1996  Funhoff et al.
5,922,481 A *  7/1999  Etzbach .............. H05B 33/14
                                              428/690

(Continued)

FOREIGN PATENT DOCUMENTS

CN    1978441 A    6/2007
CN    102959008 A  3/2013

(Continued)

OTHER PUBLICATIONS

Hreha et al., Tetrahedron 60, (2004), pp. 7169-7176. (Year: 2004).*

(Continued)

*Primary Examiner* — Dawn L Garrett
(74) *Attorney, Agent, or Firm* — Faegre Drinker Biddle & Reath LLP

(57) ABSTRACT

The present invention relates to compounds of formula (1). The compounds are suitable for use in electronic devices, in particular organic electroluminescent devices, comprising these compounds. In some embodiments, the compounds are used as matrix materials for phosphorescent or fluorescent emitters as well as a hole-blocking or electron-transport materials.

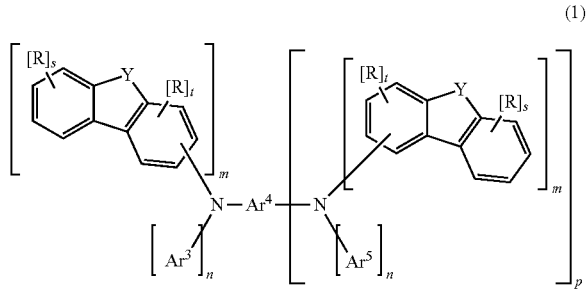

(1)

13 Claims, No Drawings

(56) References Cited

U.S. PATENT DOCUMENTS

| | | | |
|---|---|---|---|
| 9,583,717 B2 | 2/2017 | Ludemann et al. | |
| 9,644,070 B2 | 5/2017 | Eckes et al. | |
| 2003/0118866 A1* | 6/2003 | Oh | H01L 51/006 428/690 |
| 2006/0051690 A1 | 3/2006 | Matoliukstyte et al. | |
| 2012/0001127 A1 | 1/2012 | Brown et al. | |
| 2015/0094437 A1† | 4/2015 | Caille | |
| 2017/0186953 A1* | 6/2017 | Brown | C09D 11/102 |

FOREIGN PATENT DOCUMENTS

| | | | |
|---|---|---|---|
| CN | 104271632 A | | 1/2015 |
| CN | 104321362 A | | 1/2015 |
| CN | 105733562 A | | 7/2016 |
| CN | 106699573 A | | 5/2017 |
| CN | 108026254 A | | 5/2018 |
| EP | 0637899 A1 | | 2/1995 |
| EP | 2732479 A1 | | 5/2014 |
| JP | 2004-206893 A | | 7/2004 |
| JP | 2007-514654 A | | 6/2007 |
| JP | 2014-527037 A | | 10/2014 |
| JP | 2015-511215 A | | 4/2015 |
| KR | 20090117078 A | † | 11/2009 |
| KR | 101695270 B1 | | 1/2017 |
| WO | 96/20253 A1 | | 7/1996 |
| WO | 2013/007348 A1 | | 1/2013 |
| WO | 2013/096832 A2 | | 6/2013 |
| WO | 2013/146806 A1 | | 10/2013 |
| WO | 2013/156130 A1 | | 10/2013 |
| WO | 2013/180036 A1 | | 12/2013 |
| WO | 2016/026122 A1 | | 2/2016 |
| WO | WO 2016/026122 A1 * | | 2/2016 |

OTHER PUBLICATIONS

Huang et al., Journal of Materials Chemistry, (2008), vol. 18, pp. 4495-4509. (Year: 2008).*

Machine translation for CN 105733562 A (Publication date: Jul. 2016). (Year: 2016).*

International Search Report for PCT/EP2017/074961 dated Mar. 22, 2018.

Written Opinion of the International Searching Authority for PCT/EP2017/074961 dated Mar. 22, 2018.

Chang, Y., "Blade coating of Tris(8-hydroxyquinolinato)aluminum as the electron-transport layer for all-solution blue fluorescent organic light-emitting diodes," Organic Electronics, vol. 29, 2016, pp. 99-106.

Lin, C., "Hole mobilities of thermally polymerized triaryldiamine derivatives and their application as hole-transport materials in organic light-emitting diodes (OLEDs)" Organic Electronics, vol. 10, 2009, pp. 181-188.

Lin, H., "Solution-processed hexaazatriphenylene hexacarbonitrile as a universal hole-injection layer for organic light-emitting diodes," Organic Electronics, vol. 14, 2013, pp. 1204-1210.

* cited by examiner
† cited by third party

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2017/074961, filed Oct. 2, 2017, which claims benefit of European Application No. 16192507.8, filed Oct. 6, 2016, both of which are incorporated herein by reference in their entirety.

The present invention relates to crosslinkable compounds, to the crosslinked compounds obtained from these compounds, and to processes for the preparation thereof. The invention is furthermore directed to the use of these compounds in electronic devices, in particular in organic electroluminescent devices, and to the corresponding electronic devices themselves.

In electronic or opto-electronic devices, in particular in organic electroluminescent devices (OLED), components of various functionality are required. In OLEDs, the different functionalities are normally present in different layers. In this case, the term multilayered OLED systems is used. These multilayered OLED systems have, inter alia, charge-injecting layers, such as, for example, electron- and hole-injecting layers, charge-transporting layers, such as, for example, electron- and hole-conducting layers, and layers which comprise light-emitting components. These multilayered OLED systems are generally produced by successive layer-wise application.

In addition, however, it is also necessary to match the functionalities of the individual layers to one another from the material side in such a way that the best possible results, for example with respect to lifetime, efficiency, etc., are achieved. Thus, in particular, the layers which are directly adjacent to an emitting layer, in particular the hole-transporting layer (HTL=hole transport layer), have a significant influence on the properties of the adjacent emitting layer.

The different layers in an OLED are usually applied by vapour deposition in a vacuum chamber or are processed from solution. The processes based on vapour deposition lead to good results but such processes are complex and thus expensive and unsuitable, in particular, for relatively high-molecular-weight compounds, such as, for example, polymers. Polymeric OLED materials are therefore usually applied by coating from solution.

In the case of low-molecular-weight organic compounds (so-called "Small Molecules"), processing from solution would also be desirable owing to the high technical complexity in the case of vacuum processing. Furthermore, it is also desirable to replace polymeric OLED materials with Small Molecules because the synthesis of Small Molecules is easier to control in terms of reproducibility than the synthesis of polymeric materials. The purification of Small Molecules is also easier than the purification of polymeric materials.

If a plurality of layers are applied from solution, it must be ensured that a layer that has already been applied is not destroyed after it has been dried, by the subsequent application of the solution for the production of the next layer. This can be achieved, for example, by making a layer insoluble, for example by crosslinking. Such processes are disclosed, for example, in EP 0 637 899 and WO 96/20253.

As crosslinking activation, temperature treatment is generally preferred over UV irradiation, since a thermal drying process is generally carried out anyway in order to remove the solvent in the case of organic semiconductors applied from solution. Thus, the crosslinking process can easily be integrated into the production process and damage to the semiconducting material by UV radiation can be excluded. It is likewise preferred to avoid the use of an initiator. For the thermal crosslinking, the temperature is selected in such a way that the crosslinking reaction can take place. It is desirable here to select a temperature range in which the crosslinkable material and the other materials already present in the layer structure do not decompose.

In EP2732479, crosslinkable Small Molecules that can be processed from solution are used to build-up hole injection and hole transport layers. However, there is still a demand for crosslinkable Small Molecules which have hole-transport properties and are thus suitable for use in a hole-transport or hole-injection layer, and which contain groups which are suitable for crosslinking. It is advantageous here for these crosslinkable groups to be crosslinked easily, i.e. with low expenditure of energy, and, even in the crosslinked state, to have no negative effects on the function of the electronic device. The compounds should furthermore result in advantageous properties with respect to efficiency, lifetime and voltage of the OLED or at least not impair them compared with the corresponding uncrosslinked compounds or compared with crosslinked polymers.

One of the objects of the present invention was therefore to provide compounds which, on the one hand, can be processed from solution and which, on the other hand, result in an improvement in the properties of the OLEDs, more particularly in terms of lifetime, efficiency and operating voltage, especially when these compounds are used in the hole-transport layer thereof.

Surprisingly, it has been found that certain arylamine derivatives, described in greater detail below, which are substituted by one or more crosslinkable group(s), which is/are not part of the conjugation system of the amine group, achieve this object. Particularly efficient and long-lived OLEDs, in particular also those which are based on triplet emission or on blue singlet emission, can be built up using these crosslinkable compounds. The crosslinkable compounds can be crosslinked thermally or optically, with or without initiator, on the substrate or on a layer comprising a conductive doped polymer and in this way allow the controlled application of a further layer from solution. This operation can also be repeated a number of times, where either the same or different crosslinkable compounds can be used for this purpose.

The present invention therefore relates to a compound of the following formula (1), formula (1)

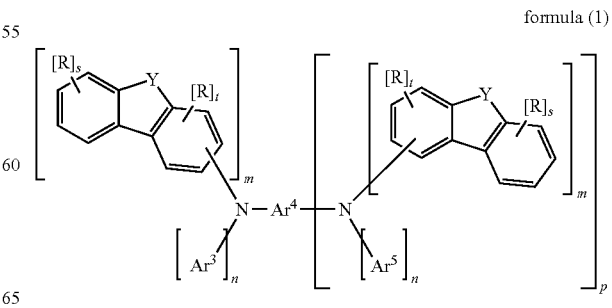

where:
Y is a group of formula (Y-1), (Y-2) or (Y-3),

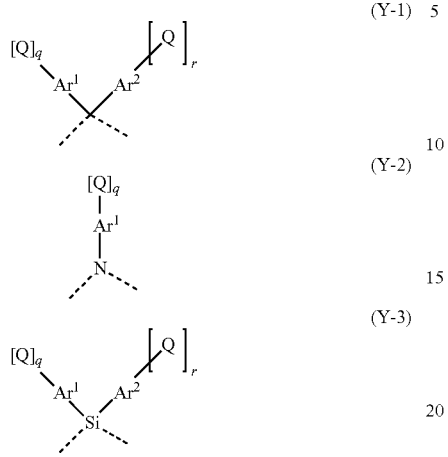

where the dashed bonds indicate the bonds to the ring comprising Y;
- $Ar^1$, $Ar^2$, $Ar^3$, $Ar^4$, $Ar^5$ are selected on each occurrence, identically or differently, from the group consisting of an aromatic or heteroaromatic ring system having 5 to 60 aromatic ring atoms, which may be substituted by one or more radicals R; where two groups $Ar^1$ and $Ar^2$ are allowed to be connected via a single bond or a divalent bridge;
- Q is on each occurrence, identically or differently, a crosslinkable group bonded to $Ar^1$ via a single bond, or Q is a crosslinkable mono- or polycyclic group condensed on $Ar^1$;
- R is on each occurrence, identically or differently, H, D, F, Cl, Br, I, CHO, $N(Ar)_2$, $C(=O)Ar$, $P(=O)(Ar)_2$, $S(=O)Ar$, $S(=O)_2Ar$, $(R)C=C(R)Ar$, CN, $NO_2$, $Si(R^1)_3$, $B(OR^1)_2$, $B(R^1)_2$, $B(N(R^1)_2)_2$, $OSO_2R^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^1$, where one or more, preferably non-adjacent $CH_2$ groups may be replaced by $(R^1)C=C(R^1)$, $C\equiv C$, $Si(R^1)_2$, $Ge(R^1)_2$, $Sn(R^1)_2$, $C=O$, $C=S$, $C=Se$, $P(=O)(R^1)$, SO, $SO_2$, $N(R^1)$, O, S or $CON(R^1)$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may be substituted by one or more radicals $R^1$, where optionally two adjacent substituents R can form a mono- or polycyclic, aliphatic, aromatic or heteroaromatic ring system with one another;
- Ar is an aromatic or heteroaromatic ring system having 5 to 60 aromatic ring atoms, which may be substituted by one or more radicals $R^1$;
- $R^1$ is on each occurrence, identically or differently, H, D, F, Cl, Br, I, CHO, $N(R^2)_2$, $C(=O)R^2$, $P(=O)(R^2)_2$, $S(=O)R^2$, $S(=O)_2R^2$, $(R^2)C=C(R^2)_2$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more, preferably non-adjacent $CH_2$ groups may be replaced by $(R^2)C=C(R^2)$, $C\equiv C$, $Si(R^2)_2$, $Ge(R^2)_2$, $Sn(R^2)_2$, $C=O$, $C=S$, $C=Se$, $P(=O)(R^2)$, SO, $SO_2$, $N(R^2)$, O, S or $CON(R^2)$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, where optionally two adjacent substituents $R^1$ can form a mono- or polycyclic, aliphatic, aromatic or heteroaromatic ring system with one another;
- $R^2$ is on each occurrence, identically or differently, H, D, F, Cl, Br, I, CHO, CN, $NO_2$, a straight-chain alkyl, alkoxy or thioalkoxy group having 1 to 20 C atoms or a straight-chain alkenyl or alkynyl group having 2 to 20 C atoms or a branched or cyclic alkyl, alkenyl, alkynyl, alkoxy or thioalkoxy group having 3 to 20 C atoms, or an aromatic or heteroaromatic ring system having 5 to 30 aromatic ring atoms or an aryloxy or heteroaryloxy group having 5 to 30 aromatic ring atoms; where optionally two adjacent substituents $R^2$ can form a mono- or polycyclic, aliphatic, aromatic or heteroaromatic ring system with one another;
- m is on each occurrence, identically or differently, 1 or 2;
- n is on each occurrence, identically or differently, 0 or 1; with the proviso that m+n=2 in the amino moiety comprising a group $Ar^3$ and an aromatic or heteroaromatic ring system containing Y, and m+n=2 in the amino moiety comprising a group $Ar^5$ and an aromatic or heteroaromatic ring system containing Y;
- p is 0 or 1;
- q is 1, 2 or 3;
- r is, 0, 1, 2 or 3;
- s is on each occurrence, identically or differently, 0, 1, 2, 3 or 4; and
- t is on each occurrence, identically or differently, 0, 1, 2 or 3.

"Crosslinkable group" in the sense of the present invention means a functional group which is capable of undergoing a reaction, preferably a polymerisation reaction, and thus forming an insoluble compound. The crosslinkable group is thus a polymerisable group. As a result of the reaction of the crosslinkable group, a corresponding crosslinked compound is obtained. The chemical reaction can also be carried out in the layer, with an insoluble layer forming. The crosslinking can usually be supported by heat or by UV, microwave, X-ray or electron radiation, if necessary in the presence of an initiator. "Insoluble" in the sense of the present invention preferably means that the compound has a solubility after the crosslinking reaction, i.e. after the reaction of the crosslinkable groups, in toluene at room temperature which is at least a factor of 3, preferably at least a factor of 10, lower than that of the uncrosslinked compound of the formula (1).

"Adjacent" substituents in the sense of the present invention are substituents which are bonded to two different carbon atoms, which are linked directly to one another, or which are bonded to the same carbon atom.

Furthermore, the following definitions of chemical groups apply for the purposes of the present application:

An aryl group in the sense of this invention contains 6 to 60 aromatic ring atoms preferably 6 to 40 aromatic ring atoms; a heteroaryl group in the sense of this invention contains 5 to 60, preferably 5 to 40 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another. An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyl-triazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

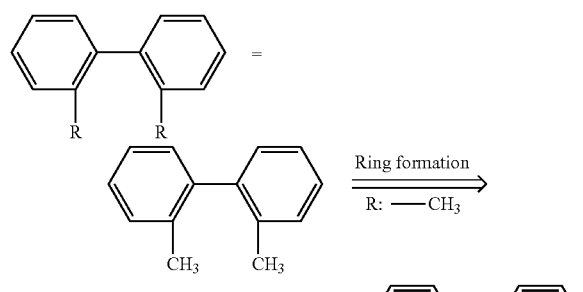

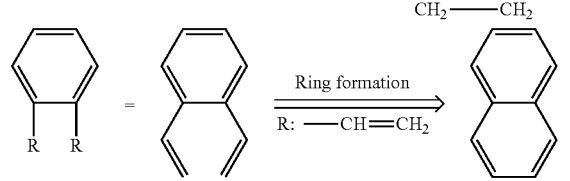

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

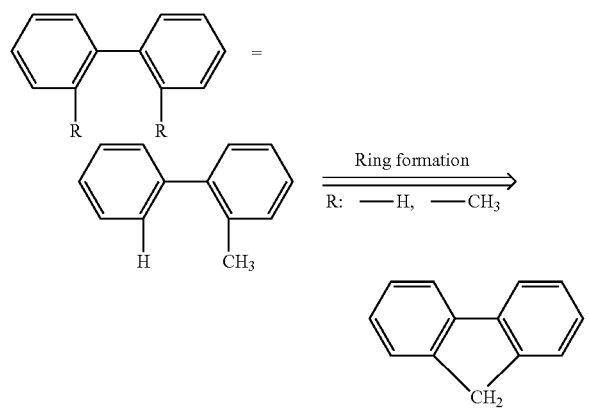

In a preferred embodiment of the present invention, the compounds of formula (1) are selected from the compounds of formulae (2) to (5),

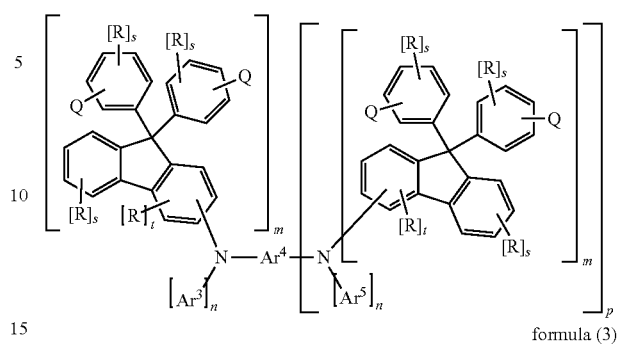
formula (2)

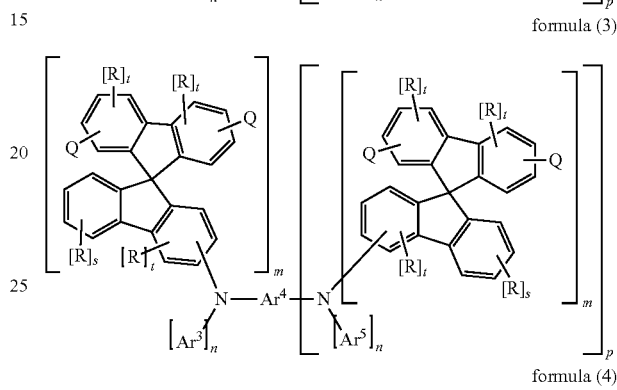
formula (3)

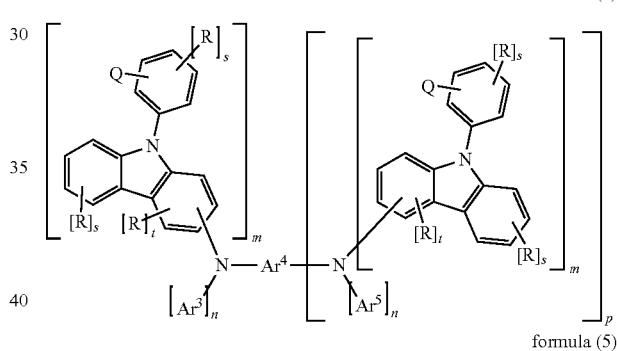
formula (4)

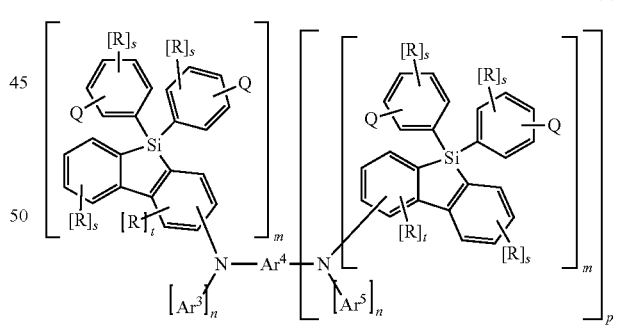
formula (5)

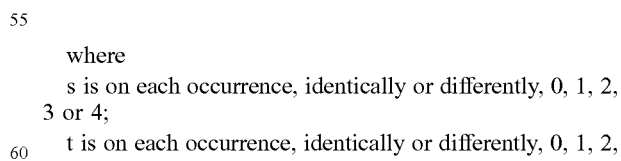

where s is on each occurrence, identically or differently, 0, 1, 2, 3 or 4;

t is on each occurrence, identically or differently, 0, 1, 2, 3;

with the proviso that s≤3 and t≤2 when the corresponding phenyl ring is substituted by a group Q which corresponds to a mono- or polycyclic group condensed on this phenyl ring; and where the others symbols and indices used have the same meanings as above.

where the symbols and indices used have the same meanings as given above.

In a very preferred embodiment of the present invention, the compounds of formula (1) are selected from the compounds of formulae (2a) to (5a),

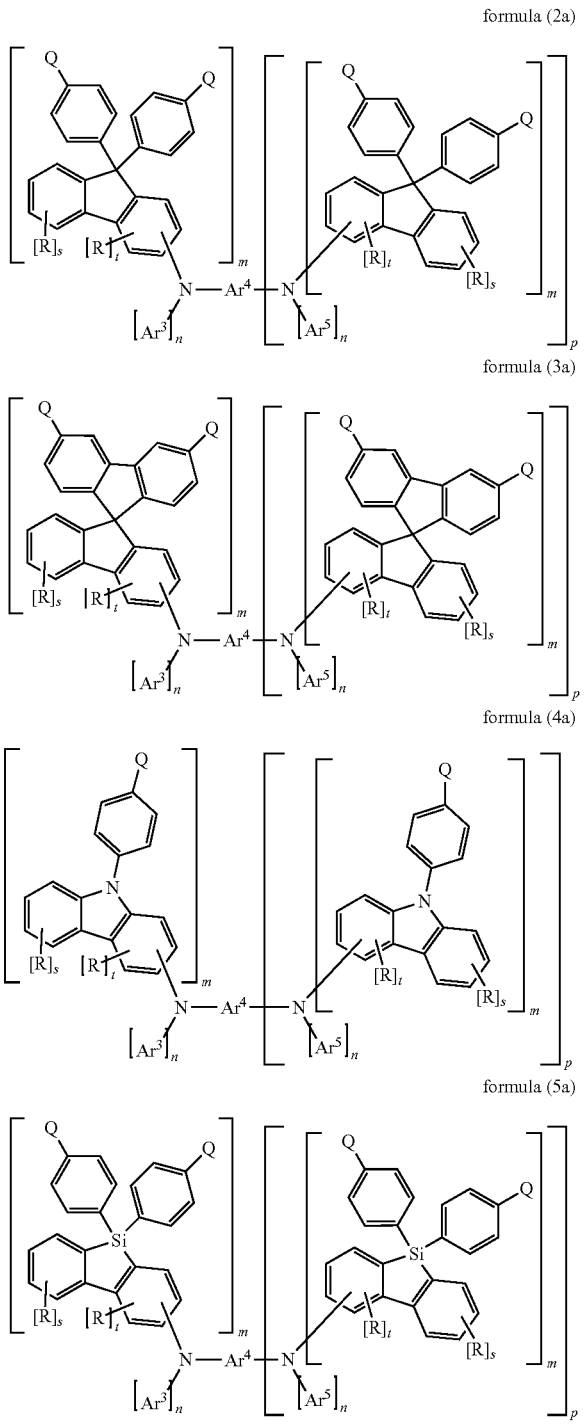

formula (2a)

formula (3a)

formula (4a)

formula (5a)

where the symbols and indices used have the same meanings as given above.

In accordance with a preferred embodiment, m is equal to 1 and n is equal to 1.

In accordance with a further preferred embodiment, m is equal to 1, n is equal to 1 and p is equal to 1.

In accordance with another preferred embodiment, m is equal to 1, n is equal to 1 and p is equal to 0.

As described above, the crosslinkable group Q is a functional group which is capable of undergoing a chemical reaction and thus forming an insoluble layer comprising the crosslinked compounds. In general, all groups Q which are known to the person skilled in the art for this purpose can be employed. The task of this group is, in particular, to link the compounds according to the invention to one another, optionally to further reactive compounds, by a crosslinking reaction. This results in a crosslinked compound, or, if the reaction is carried out in a layer, in a crosslinked layer. A crosslinked layer in the sense of the present invention is taken to mean a layer which is obtainable by carrying out the crosslinking reaction from a layer of the crosslinkable, polymeric compound according to the invention. The crosslinking reaction can in general be initiated by heat and/or by UV, microwave, X-ray or electron radiation and/or by the use of free-radical formers, anions, cations, acids and/or photoacids. The presence of catalysts may likewise be helpful or necessary. The crosslinking reaction is preferably a reaction for which no initiator and no catalyst has to be added.

Crosslinkable groups Q which are preferred in accordance with the invention are the groups mentioned below:

a) Terminal or Cyclic Alkenyl or Terminal Dienyl and Alkynyl Groups:

Suitable units are those which contain a terminal or cyclic double bond, a terminal dienyl group or a terminal triple bond, in particular terminal or cyclic alkenyl, terminal dienyl or terminal alkynyl groups having 2 to 40 C atoms, preferably having 2 to 10 C atoms, where individual $CH_2$ groups and/or individual H atoms may also be replaced by the above-mentioned groups R. Furthermore suitable are also groups which are to be regarded as precursors and are capable of the in-situ formation of a double or triple bond.

b) Alkenyloxy, Dienyloxy or Alkynyloxy Groups:

Furthermore suitable are alkenyloxy, dienyloxy or alkynyloxy groups, preferably alkenyloxy groups.

c) Acrylic Acid Groups:

Furthermore suitable are acrylic acid units in the broadest sense, preferably acrylates, acrylamides, methacrylates and methacrylamides. $C_{1-10}$-alkyl acrylate and $C_{1-10}$-alkyl methacrylate are particularly preferred.

The crosslinking reaction of the groups mentioned above under a) to c) can take place via a free-radical, cationic or anionic mechanism, but also via cycloaddition.

It may be helpful to add a corresponding initiator for the crosslinking reaction. Suitable initiators for free-radical crosslinking are, for example, dibenzoyl peroxide, AIBN or TEMPO. Suitable initiators for cationic crosslinking are, for example, $AlCl_3$, $BF_3$, triphenylmethyl perchlorate or tropylium hexachloroantimonate. Suitable initiators for anionic crosslinking are bases, in particular butyllithium.

In a preferred embodiment of the present invention, however, the crosslinking is carried out without the addition of an initiator and is initiated exclusively thermally. This preference is due to the fact that the absence of the initiator prevents contamination of the layer, which could result in impairment of the device properties.

d) Oxetanes and Oxiranes:

A further suitable class of crosslinkable groups Q are oxetanes and oxiranes, which crosslink cationically by ring opening.

It may be helpful to add a corresponding initiator for the crosslinking reaction. Suitable initiators are, for example, AlCl$_3$, BF$_3$, triphenylmethyl perchlorate or tropylium hexachloroantimonate. Photoacids can likewise be added as initiators.

e) Silanes:

Furthermore suitable as a class of crosslinkable groups are silane groups SiR$_3$, where at least two groups R, preferably all three groups R, stand for Cl or an alkoxy group having 1 to 20 C atoms.

This group reacts in the presence of water to give an oligo- or polysiloxane.

f) Cyclobutane Groups

The above-mentioned crosslinkable groups Q are generally known to the person skilled in the art, as are the suitable reaction conditions which are used for the reaction of these groups.

Preferred crosslinkable groups Q include alkenyl groups of the following formula Q1, dienyl groups of the following formula Q2, alkynyl groups of the following formula Q3, alkenyloxy groups of the following formula Q4, dienyloxy groups of the following formulae Q5, alkynyloxy groups of the following formula Q6, acrylic acid groups of the following formulae Q7 and Q8, oxetane groups of the following formulae Q9 and Q10, oxirane groups of the following formula Q11 and cyclobutane groups of the following formula Q12:

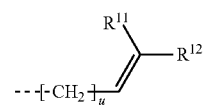
Q1

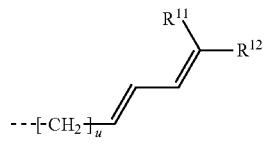
Q2

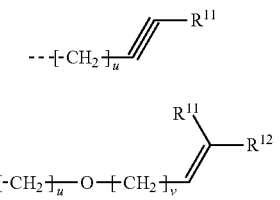
Q3

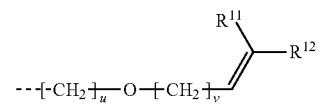
Q4

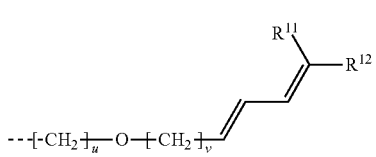
Q5

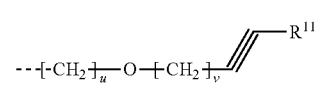
Q6

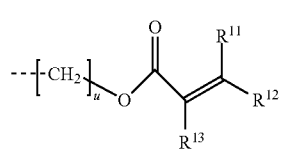
Q7

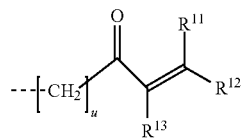
Q8

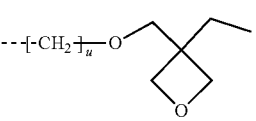
Q9

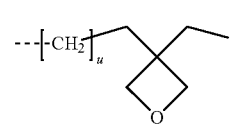
Q10

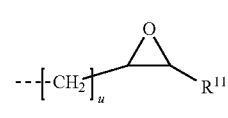
Q11

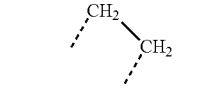
Q12 where the dashed bond in the formula formulae Q1 to Q11 and the dashed bonds in the formula Q12 represent the linking of the crosslinkable group to the structural units; and where R$^{11}$, R$^{12}$ and R$^{13}$ in the formulae Q1 to Q8 and Q11 are on each occurrence, identically or differently, H, a straight-chain or branched alkyl group having 1 to 6 C atoms, preferably 1 to 4 C atoms. The radicals R$^{11}$, R$^{12}$ and R$^{13}$ are particularly preferably H, methyl, ethyl, n-propyl, isopropyl, n-butyl, sec-butyl or tert-butyl and very particularly preferably H or methyl;

u is an integer from 0 to 8; and v is an integer from 1 to 8.

The crosslinkable groups of the formulae Q1 to Q12 may be linked directly to the structural unit, or else indirectly, via a further mono- or polycyclic, aromatic or heteroaromatic ring system Ar$^{10}$, as depicted in the following formulae Q13 to Q24:

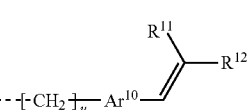
Q13

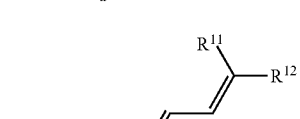
Q14

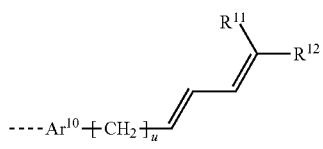
Q15

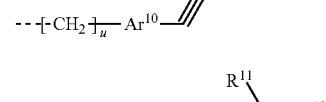
Q16

-continued

Q17 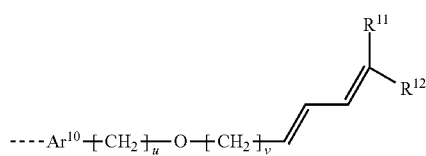

Q18 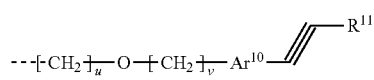

Q19 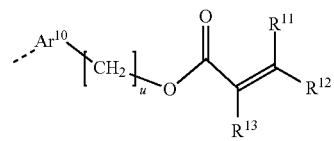

Q20 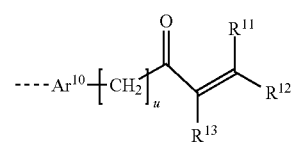

Q21 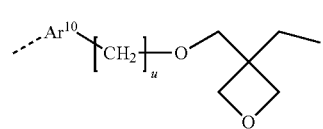

Q22 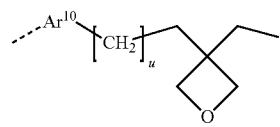

Q23 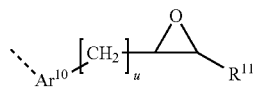

Q24 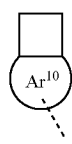

where the dashed bond in formulae Q13 to Q24 represent the linking of the crosslinkable group to the structural units; and where $Ar^{10}$ is on each occurrence, in each case identically or differently, a mono- or polycyclic, aromatic or heteroaromatic ring system having 5 to 60 aromatic ring atoms, which may be substituted by one or more radicals R, where R is as defined above. More preferably, $Ar^{10}$ is on each occurrence, in each case identically or differently, an aryl or heteroaryl group having 5 to 30 aromatic ring atoms, which may be substituted by one or more radicals R. Very preferably, $Ar^{10}$ is on each occurrence, in each case identically or differently, a benzene or a biphenyl group, which may be substituted by one or more radicals R.

Particularly preferred crosslinkable groups Q are the following:

Q1a 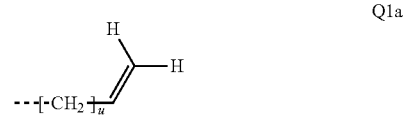

Q2a 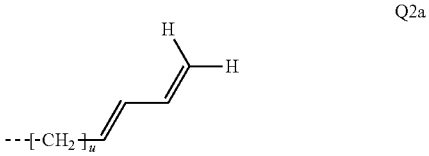

Q4a 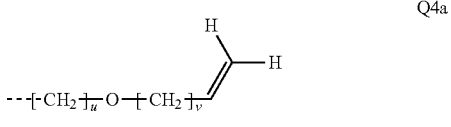

Q7a 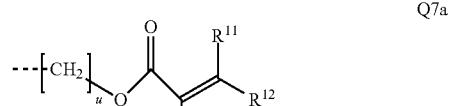

Q7b 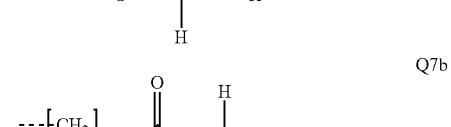

Q9a 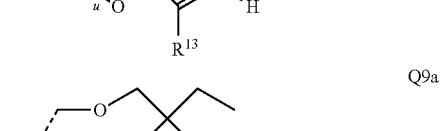

Q12a 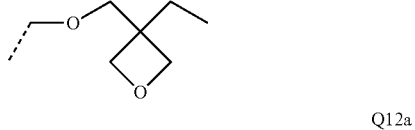

Q13a 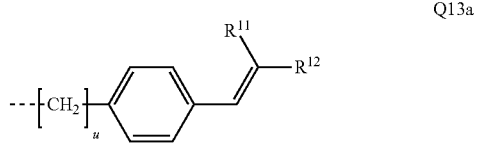

Q14a 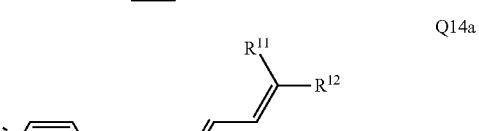

Q16a 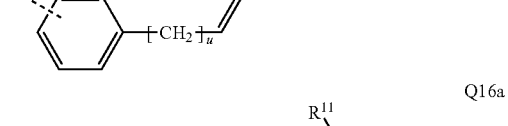

Q19a 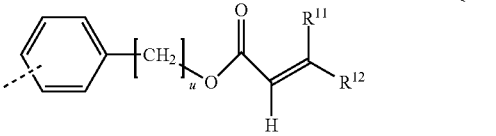

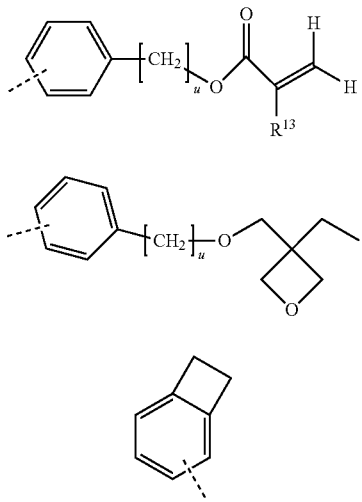

Q19b

Q21a

Q24a

The radicals $R^{11}$ and $R^{12}$ in the formulae Q7a and Q13a to Q19a are on each occurrence, identically or differently, H or a straight-chain or branched alkyl group having 1 to 6 C atoms, preferably 1 to 4 C atoms. The radicals $R^{11}$ and $R^{12}$ are particularly preferably methyl, ethyl, n-propyl, isopropyl, n-butyl, sec-butyl or tert-butyl and very particularly preferably methyl.

The radical $R^{13}$ in the formulae Q7b and Q19b is on each occurrence a straight-chain or branched alkyl group having 1 to 6 C atoms, preferably 1 to 4 C atoms. The radical $R^{13}$ is particularly preferably methyl, ethyl, n-propyl, isopropyl, n-butyl, sec-butyl or tert-butyl and very particularly preferably methyl.

The indices used have the following meaning: u=0 to 8 and v=1 to 8.

Very particularly preferred crosslinkable groups Q are the following:

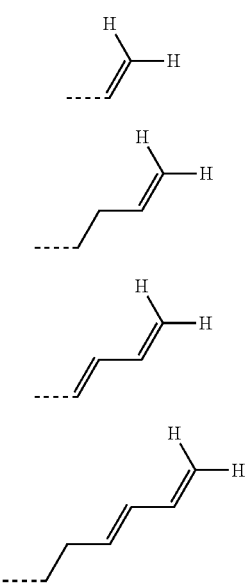

Q1b

Q1c

Q2b

Q2c

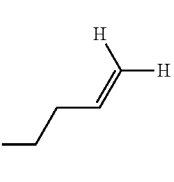

Q4b

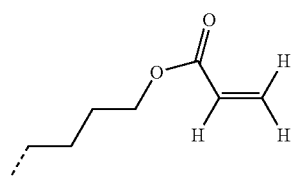

Q7c

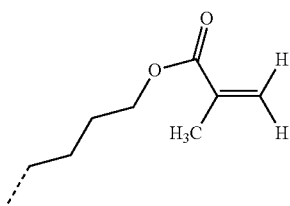

Q7d

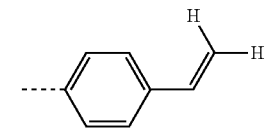

Q12b

Q13b

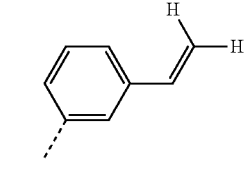

Q13c

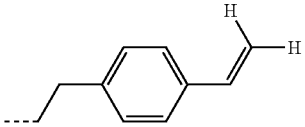

Q13d

Q13e

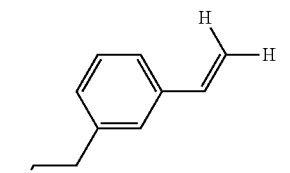

Q14b

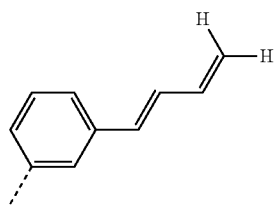
Q14c

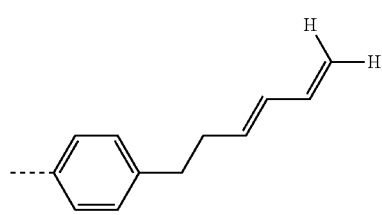
Q14d

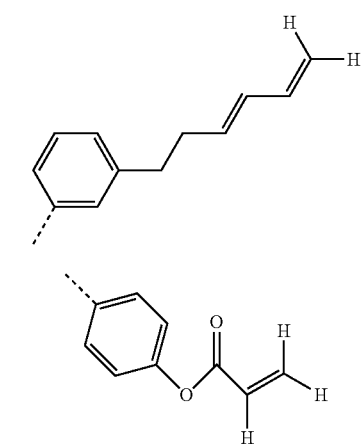
Q14e

Q19c

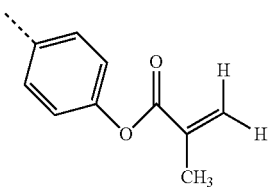
Q19d

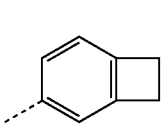
Q24b

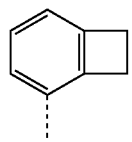
Q24c

In the preferred groups Q1 to Q24, in the particularly preferred groups Q1a to Q24a and in the very particularly preferred groups Q1b to Q24c, the dashed lines represent the bonds to the structural units. It should be noted in this connection that the groups Q12, Q12a, Q12b and Q24 each have two bonds to two adjacent ring carbon atoms of the structural unit. All other crosslinkable groups have only one bond to the structural unit.

In accordance with a preferred embodiment, Q, in formulae (2a) to (5a), is a crosslinkable group corresponding to Q1b, and compounds of formulae (2a) to (5a) are selected from compounds of the following formulae (2b) to (5b),

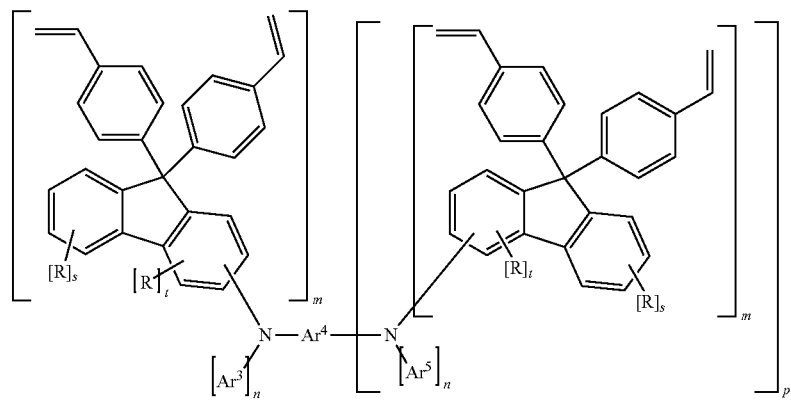

formula (2b)

formula (3b)
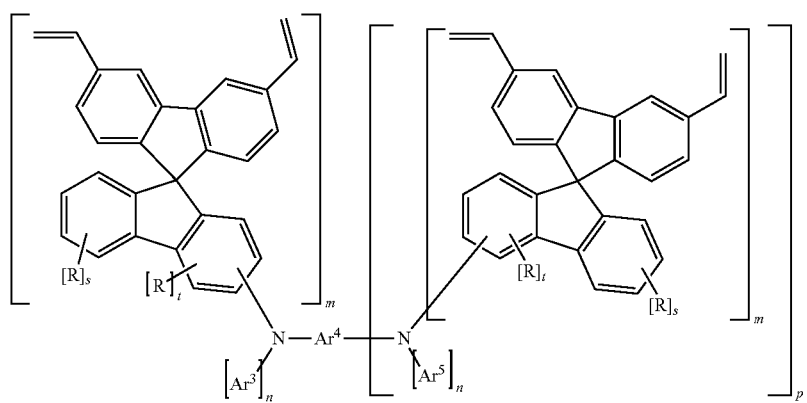
formula (4b)
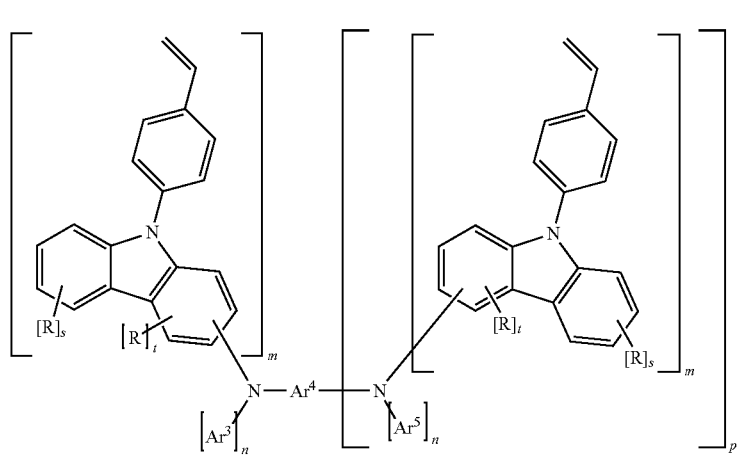
formula (5b)
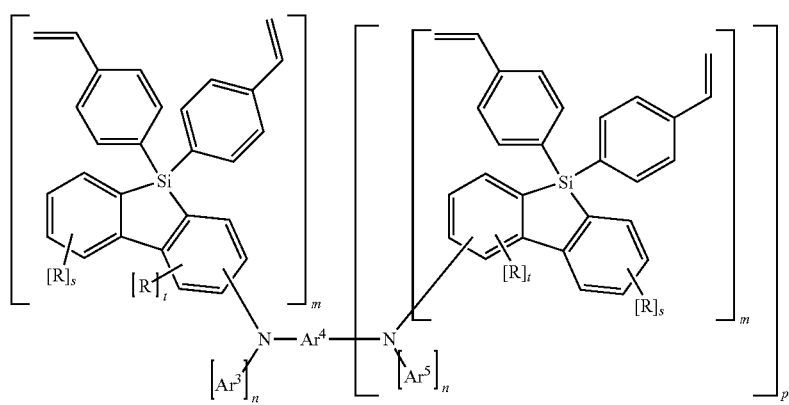

In accordance with another preferred embodiment, Q, in formulae (2a) to (5a), is a condensed crosslinkable mono- or polycyclic group corresponding to the group Q12b and compounds of formulae (2a) to (5a) are selected from compounds of the following formulae (2c) to (5c),
formula (2c)
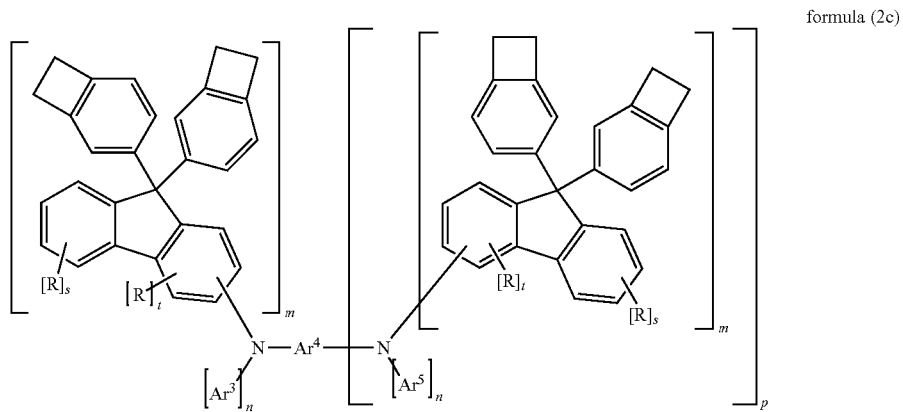
formula (3c)
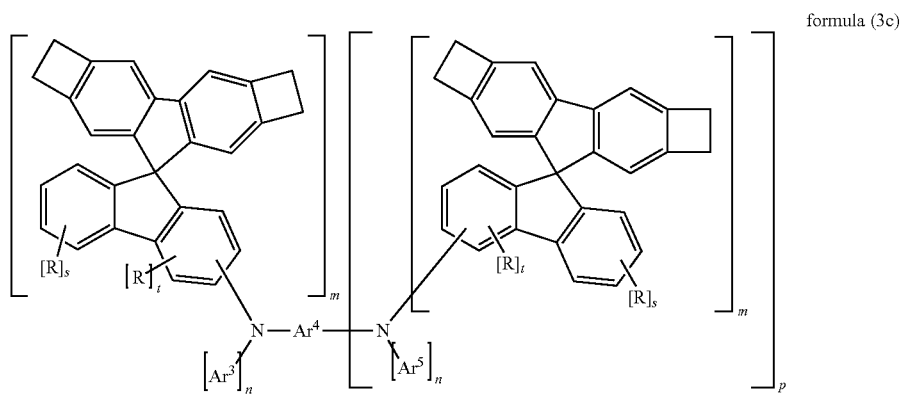
formula (4c)
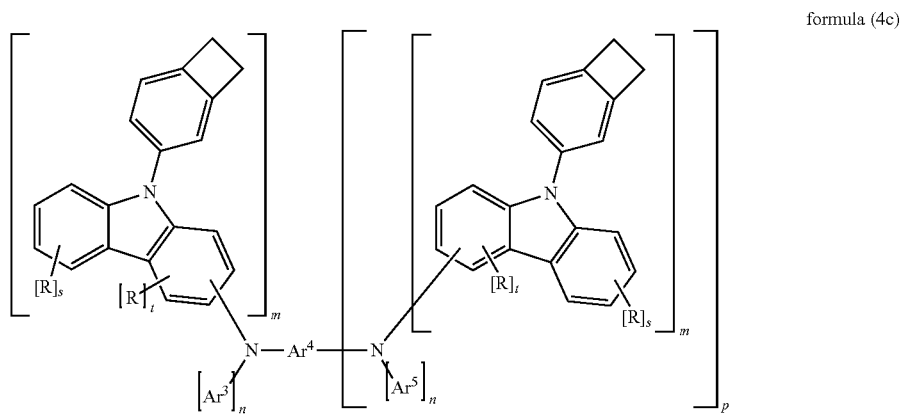

formula (5c)

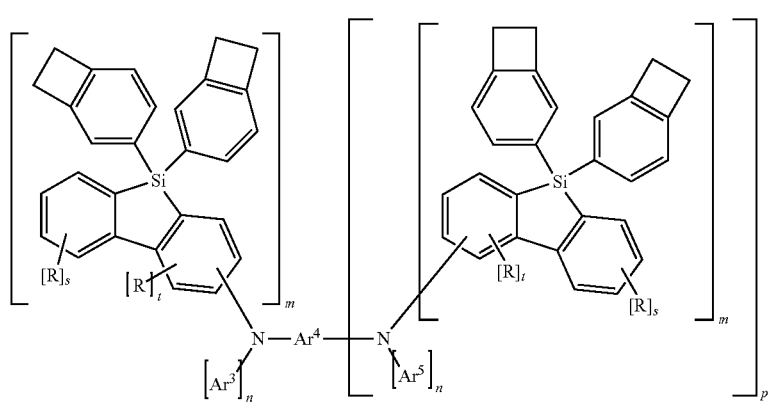

In accordance with a preferred embodiment of the invention, the groups $Ar^3$, $Ar^4$ and $Ar^5$ are selected on each occurrence, identically or differently, from the group consisting of an aromatic or heteroaromatic ring system having 5 to 30 aromatic ring atoms, which may be substituted by one or more radicals R as defined above.

It is preferred that the groups $Ar^3$, $Ar^4$ and $Ar^5$ are selected on each occurrence, identically or differently, from the group consisting of benzene, naphthalene, anthracene, phenanthrene, biphenyl, terphenyl, quaterphenyl, fluorene, dibenzofuran, dibenzothiophene, carbazole, indolocarbazole, indenocarbazole, pyridine, quinoline, isoquinoline, pyridazine, benzopyridazine, pyrimidine, benzopyrimidine, quinoxaline, pyrazine, azacarbazole, benzocarboline, 1,3,5-triazine, 1,2,4-triazine, 1,2,3-triazine, each of which may be substituted by one or more radicals R as defined above.

In a very preferred embodiment of the invention, the groups $Ar^3$ and $Ar^5$ are selected on each occurrence, identically or differently, from the groups of the following formulae (A-1) to (A-51),

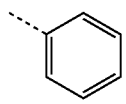
(A-1)

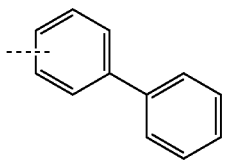
(A-2)

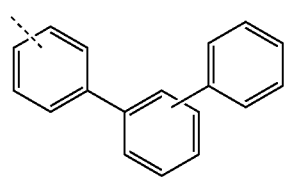
(A-3)

-continued

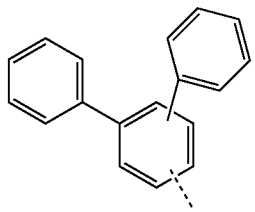
(A-4)

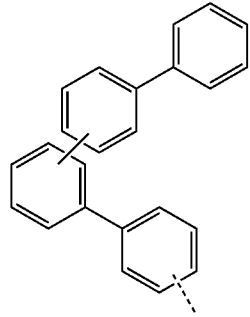
(A-5)

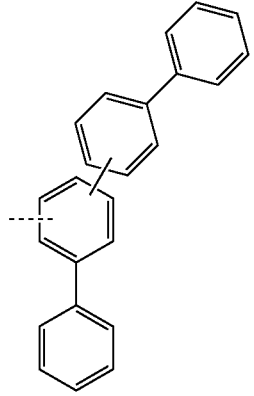
(A-6)

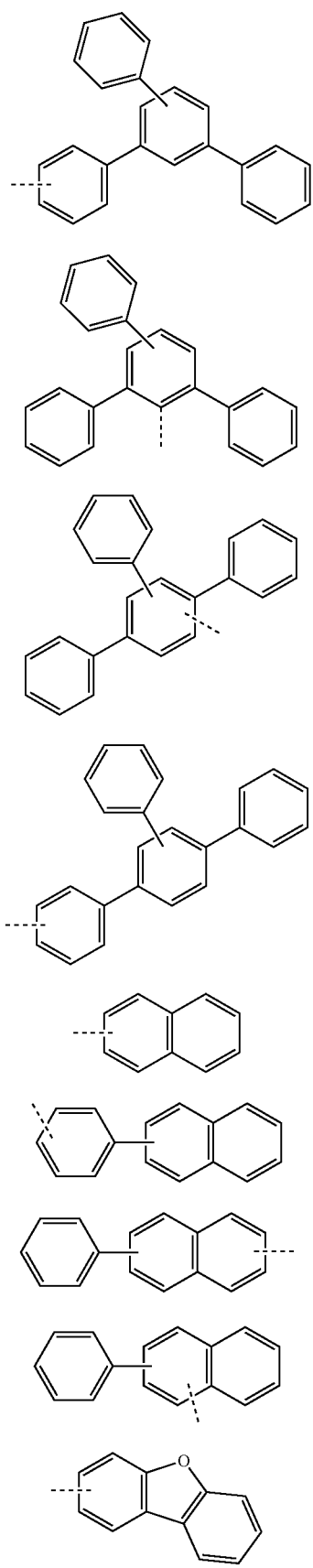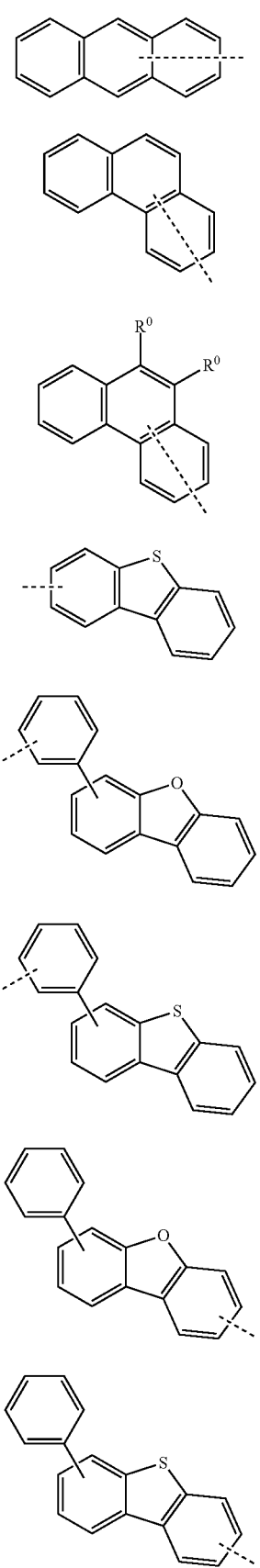

-continued
(A-24)
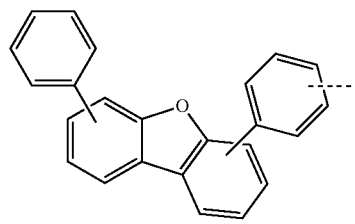
(A-25)
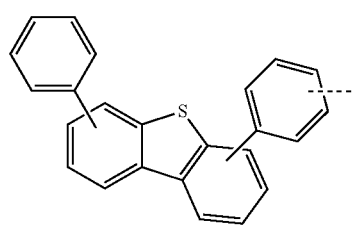
(A-26)
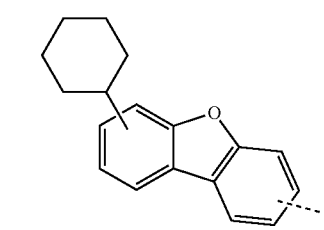
(A-27)
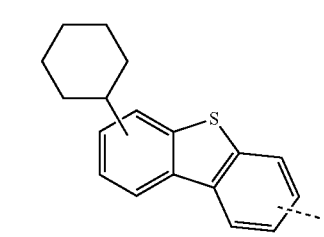
(A-28)
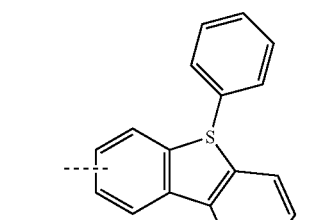
(A-29)
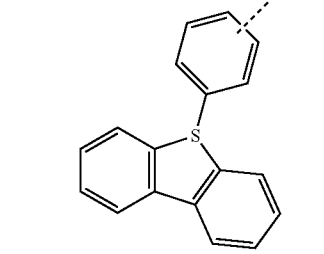
(A-30)
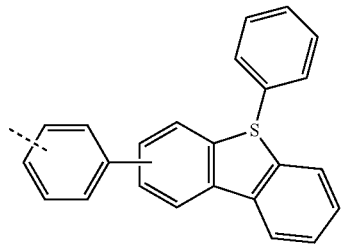
(A-31)
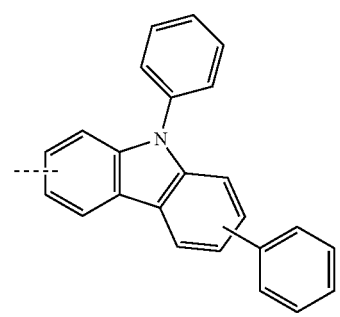
(A-32)
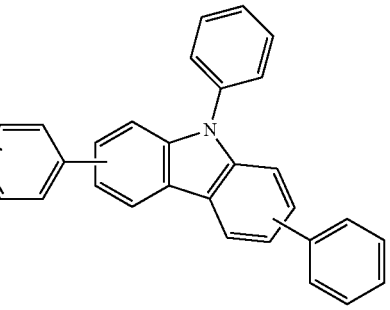
(A-33)
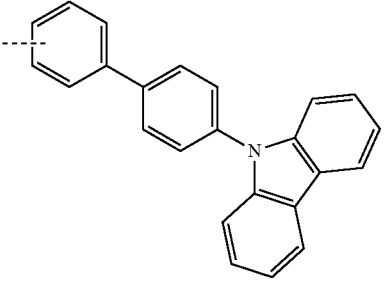
(A-34)
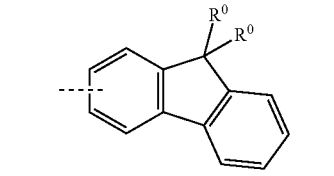
(A-35)
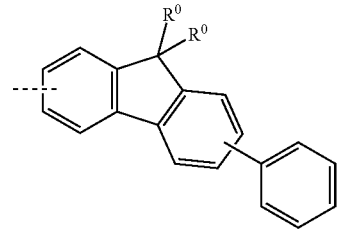

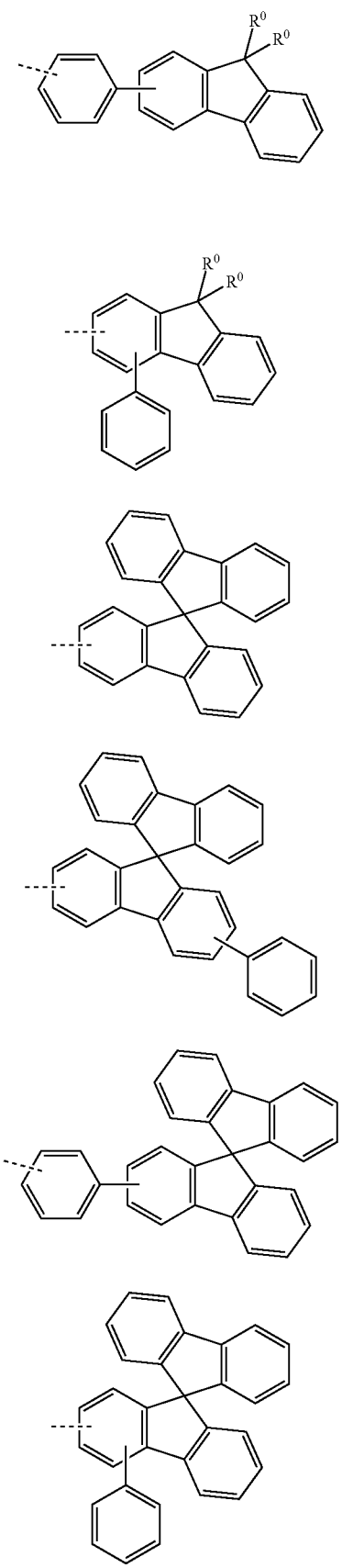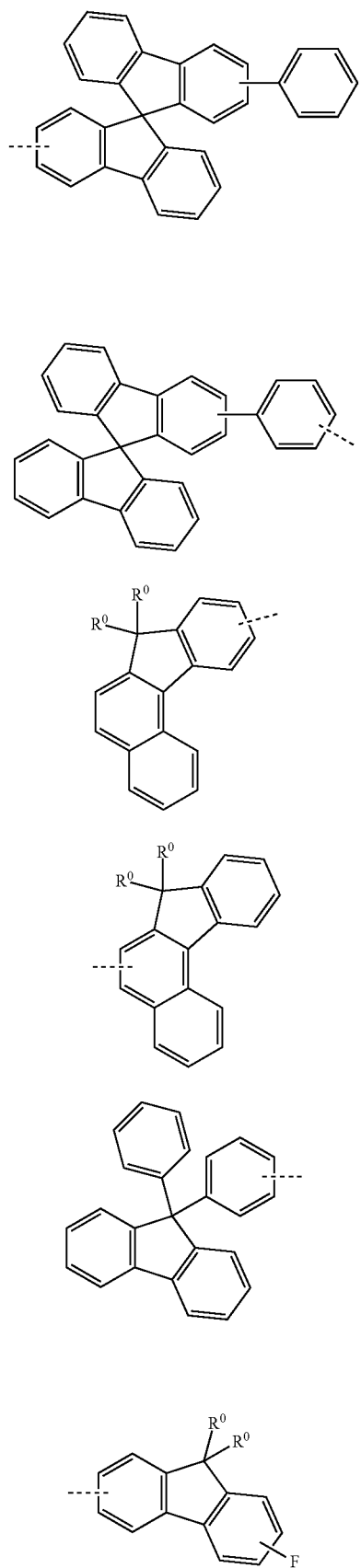

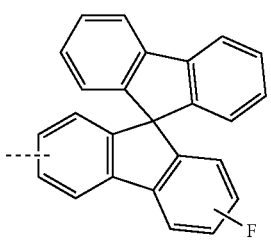 (A-48)

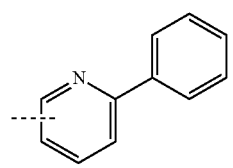 (A-49)

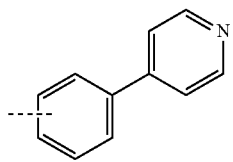 (A-50)

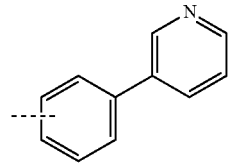 (A-51)

where the dashed bond indicates the bond to the nitrogen atom,
where the groups of formulae (A-1) to (A-51) may further be substituted at each free position by a group R as defined above,
and where
$R^0$, in formulae (A-18), (A-34) to (A-37), (A-44), (A-45) and (A-47), is selected on each occurrence, identically or differently, from the group consisting of H, D, F, CN, $Si(R^3)_3$, a straight-chain alkyl group having 1 to 20 C atoms or a branched or cyclic alkyl group having 3 to 20 C atoms, each of which may be substituted by one or more radicals $R^1$, an aromatic or heteroaromatic ring system having 5 to 18 aromatic ring atoms, which may in each case be substituted by one or more radicals $R^1$, where two adjacent substituents $R^0$ may optionally form a mono- or polycyclic, aliphatic ring system or aromatic ring system, which may be substituted by one or more radicals $R^1$. The group $R^0$ is preferably selected from the group consisting of H, F, a straight-chain alkyl group having 1 to 10 C atoms or a branched or cyclic alkyl group having 3 to 10 C atoms, each of which may be substituted by one or more radicals $R^1$, an aryl or heteroaryl group having 5 to 12 aromatic ring atoms, which may in each case be substituted by one or more radicals $R^1$, where two adjacent substituents $R^0$ may optionally form a mono- or polycyclic, aliphatic ring system or aromatic ring system, which may be substituted by one or more radicals $R^1$.

In accordance with a preferred embodiment, p is equal to 0 and $Ar^4$ is on each occurrence, identically or differently, selected from the groups of the formulae (A-1) to (A-51) as defined above.

In accordance with another preferred embodiment, p is equal to 1 and $Ar^4$ is on each occurrence, identically or differently, selected from the groups of the following formulae (B-1) to (B-24),

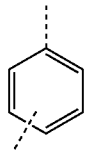 B-1

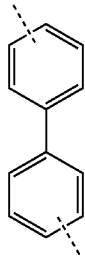 B-2

B-3

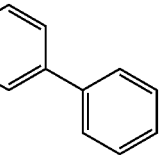

B-4

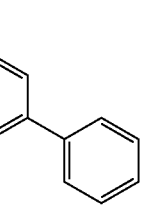

B-5

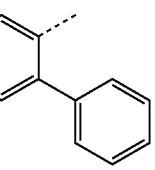

B-6

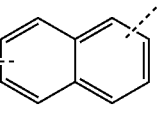

B-7

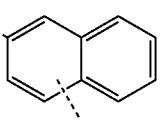

B-8

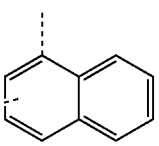

B-9

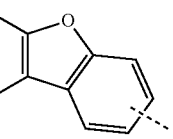

B-10
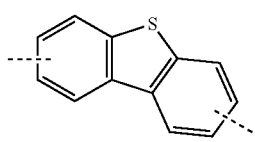
B-11
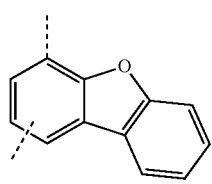
B-12
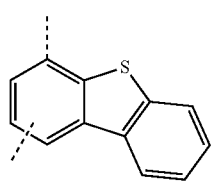
B-13
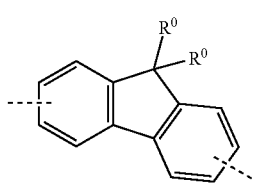
B-14
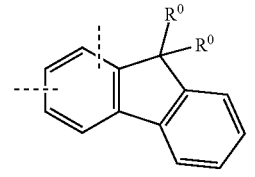
B-15
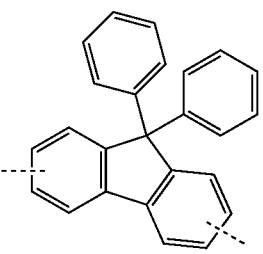
B-16
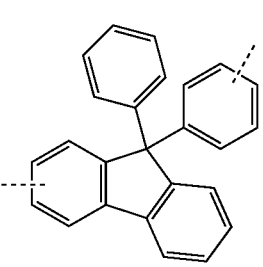
B-17
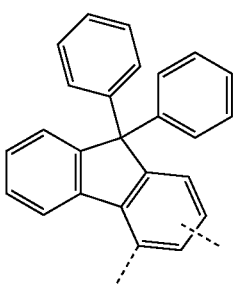
B-18
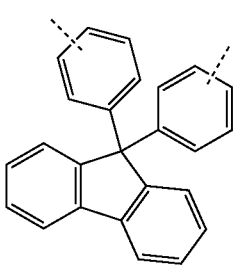
B-19
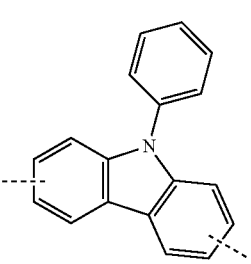
B-20
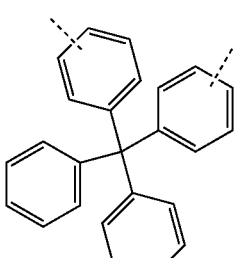
B-21
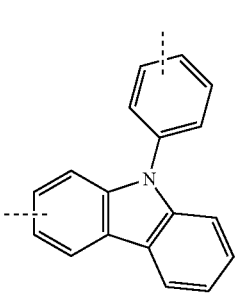
B-22
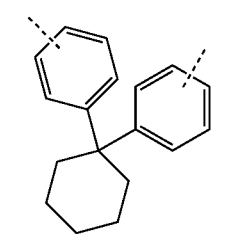

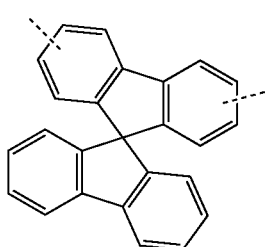

B-23

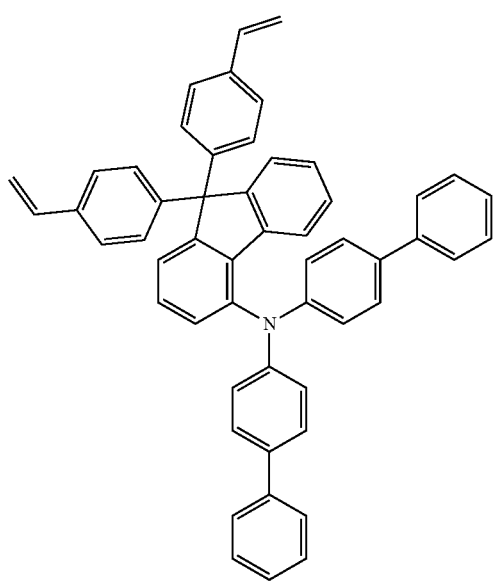 [SMILES: C=Cc1ccc(C2(c3ccc(C=C)cc3)c3ccccc3-c3c(N(c4ccc(-c5ccccc5)cc4)c4ccc(-c5ccccc5)cc4)cccc32)cc1]

B-24 where the dashed bonds in (B-1) to (B-24) indicate the bonds to the nitrogen atoms of the arylamino groups depicted in formula (1);

where the groups of formulae (B-1) to (B-24) may further be substituted at each free position by a group R as defined above, and where $R^0$ has the same meaning as above.

In accordance with a preferred embodiment, R is on each occurrence, identically or differently, H, D, F, $N(Ar)_2$, a straight-chain alkyl group having 1 to 20 C atoms or a straight-chain alkenyl group having 2 to 20 C atoms or a branched or cyclic alkyl group having 3 to 20 C atoms, each of which may be substituted by one or more radicals $R^1$, where one or more, preferably non-adjacent $CH_2$ groups may be replaced by $(R^1)C=C(R^1)$, C≡C, $Si(R^1)_2$, $Ge(R^1)_2$, $Sn(R^1)_2$, C=O, C=S, C=Se, P(=O)($R^1$), SO, $SO_2$, N($R^1$), O, S or CON($R^1$) and where one or more H atoms may be replaced by D or F, or an aromatic or heteroaromatic ring system having 5 to 18 aromatic ring atoms, which may in each case be substituted by one or more radicals $R^1$, where optionally two adjacent substituents R can form a mono- or polycyclic, aliphatic, aromatic or heteroaromatic ring system with one another.

In accordance with a preferred embodiment, Ar is an aromatic or heteroaromatic ring system having 5 to 18 aromatic ring atoms, which may be substituted by one or more radicals $R^1$.

In accordance with a preferred embodiment, $R^1$ is on each occurrence, identically or differently, H, D, F, $N(R^2)_2$, a straight-chain alkyl group having 1 to 10 C atoms or a straight-chain alkenyl group having 2 to 10 C atoms or a branched or cyclic alkyl group having 3 to 10 C atoms, each of which may be substituted by one or more radicals $R^2$, and where one or more H atoms may be replaced by D or F, or an aromatic or heteroaromatic ring system having 5 to 18 aromatic ring atoms, which may in each case be substituted by one or more radicals $R^2$; where optionally two adjacent substituents $R^1$ can form a mono- or polycyclic, aliphatic, aromatic or heteroaromatic ring system with one another.

In accordance with a preferred embodiment, the compounds of formula (1) comprise at least one substituent R and/or at least one substituent $R^0$, which stands for a straight-chain alkyl group having 1 to 20 C atoms or a branched or cyclic alkyl group having 3 to 20 C atoms, each of which may be substituted by one or more radicals $R^1$.

Suitable compounds according to formula (1) are the compounds shown in the following table:

-continued
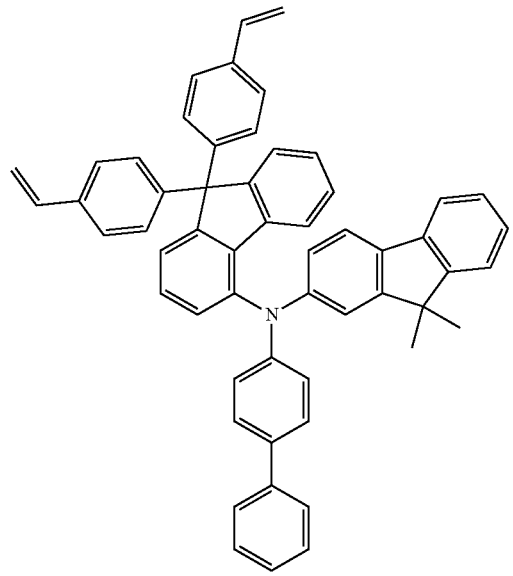 [SMILES: C=Cc1ccc(C2(c3ccc(C=C)cc3)c3ccccc3-c3c(N(c4ccc(-c5ccccc5)cc4)c4ccc5c(c4)C(C)(C)c4ccccc4-5)cccc32)cc1]
2
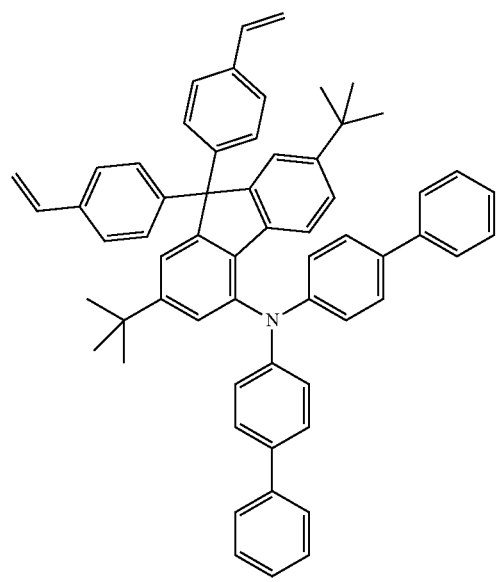 [SMILES: C=Cc1ccc(C2(c3ccc(C=C)cc3)c3cc(C(C)(C)C)ccc3-c3c(N(c4ccc(-c5ccccc5)cc4)c4ccc(-c5ccccc5)cc4)cc(C(C)(C)C)cc32)cc1]
3
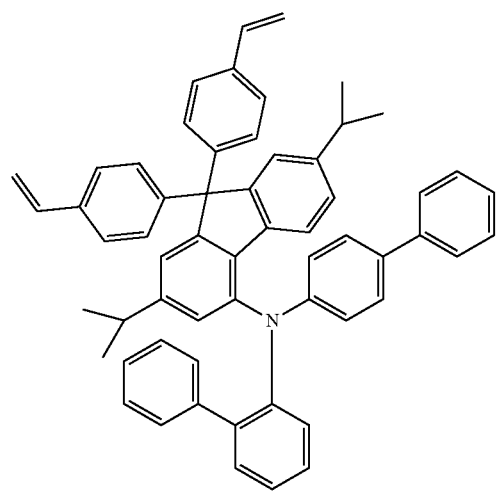 [SMILES: C=Cc1ccc(C2(c3ccc(C=C)cc3)c3cc(C(C)C)ccc3-c3c(N(c4ccc(-c5ccccc5)cc4)c4ccccc4-c4ccccc4)cc(C(C)C)cc32)cc1]
4

-continued
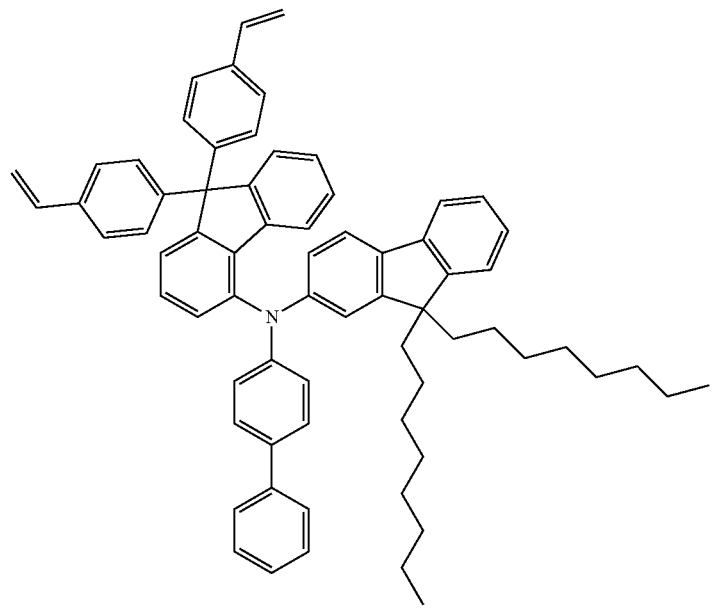 [SMILES: C=Cc1ccc(C2(c3ccc(C=C)cc3)c3ccccc3-c3c(N(c4ccc(-c5ccccc5)cc4)c4ccc5c(c4)C(CCCCCCCC)(CCCCCCCC)c4ccccc4-5)cccc32)cc1]
5
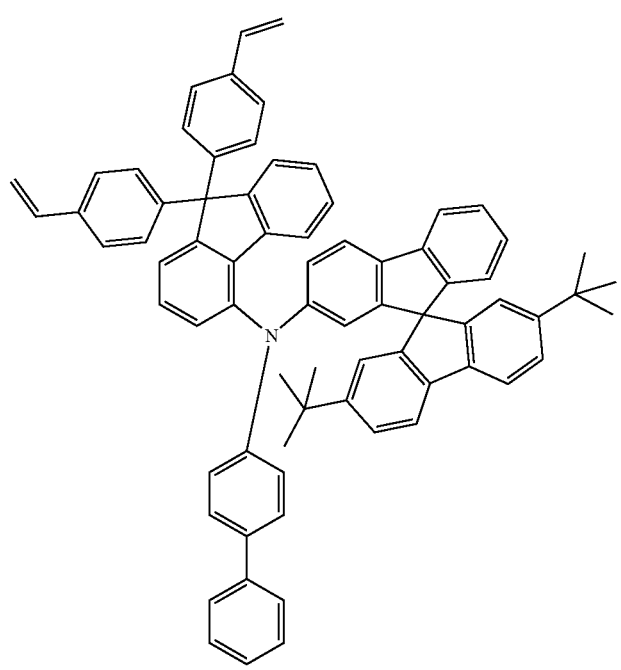 [SMILES: C=Cc1ccc(C2(c3ccc(C=C)cc3)c3ccccc3-c3c(N(c4ccc(-c5ccccc5)cc4)c4ccc5c(c4)C4(c6ccccc6-5)c5cc(C(C)(C)C)ccc5-c5ccc(C(C)(C)C)cc54)cccc32)cc1]
6

-continued
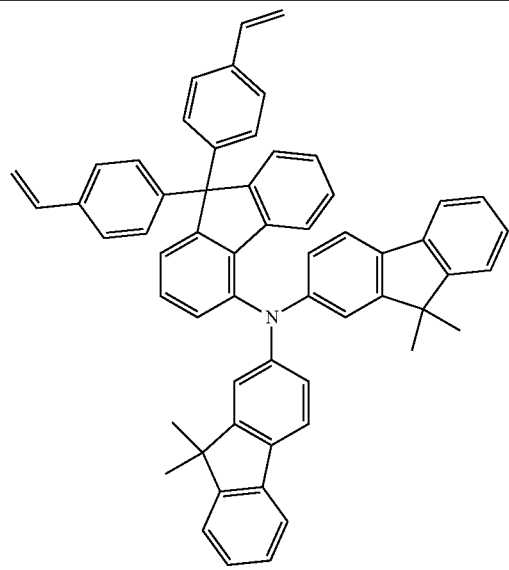
7
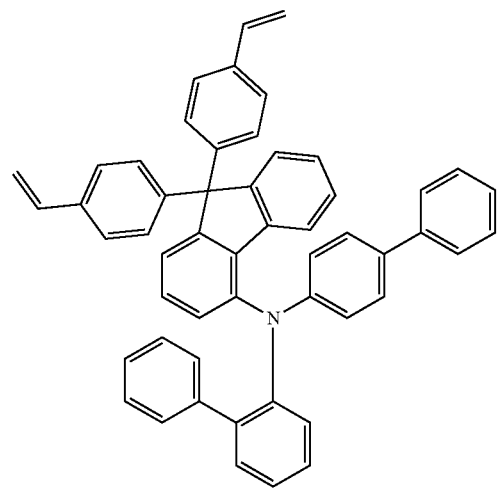 [SMILES: C=Cc1ccc(C2(c3ccc(C=C)cc3)c3ccccc3-c3c(N(c4ccc(-c5ccccc5)cc4)c4ccccc4-c4ccccc4)cccc32)cc1]
8
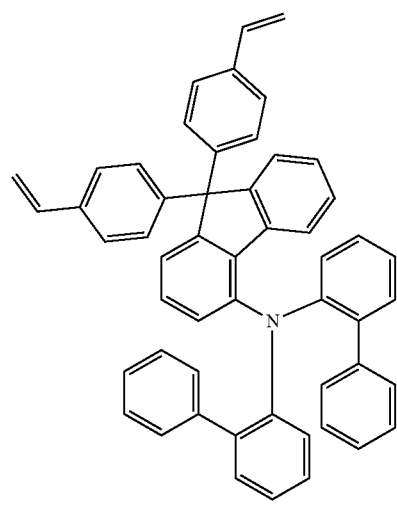 [SMILES: C=Cc1ccc(C2(c3ccc(C=C)cc3)c3ccccc3-c3c(N(c4ccccc4-c4ccccc4)c4ccccc4-c4ccccc4)cccc32)cc1]
9

10
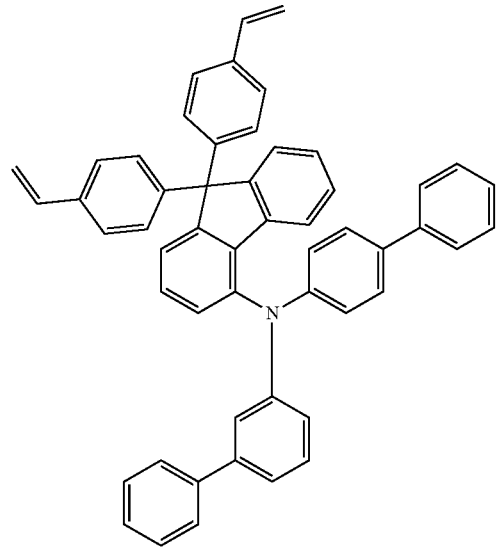 [SMILES: C=Cc1ccc(C2(c3ccc(C=C)cc3)c3ccccc3-c3c(N(c4ccc(-c5ccccc5)cc4)c4cccc(-c5ccccc5)c4)cccc32)cc1]
11
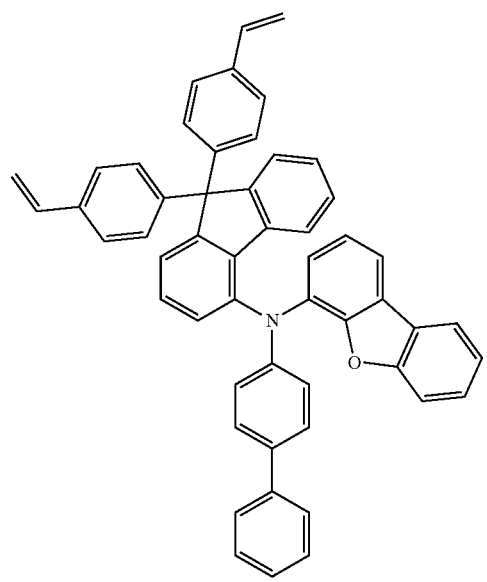 [SMILES: C=Cc1ccc(C2(c3ccc(C=C)cc3)c3ccccc3-c3c(N(c4ccc(-c5ccccc5)cc4)c4cccc5c4oc4ccccc45)cccc32)cc1]

-continued
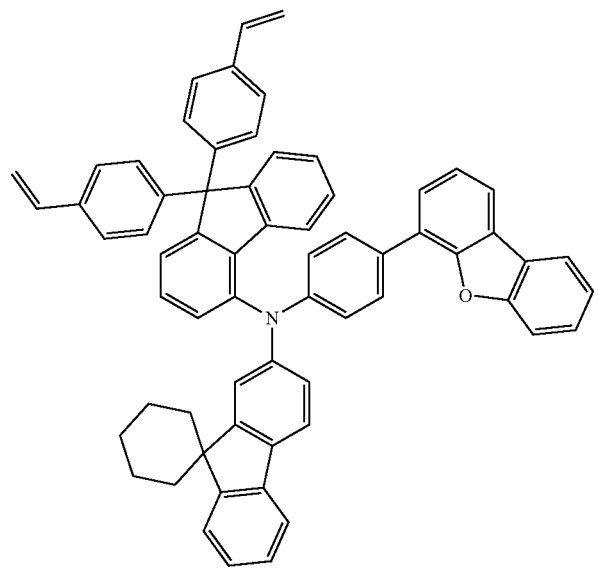 [SMILES: C=Cc1ccc(C2(c3ccc(C=C)cc3)c3ccccc3-c3c(N(c4ccc(-c5cccc6c5oc5ccccc56)cc4)c4ccc5c(c4)C4(CCCCC4)c4ccccc4-5)cccc32)cc1]
12
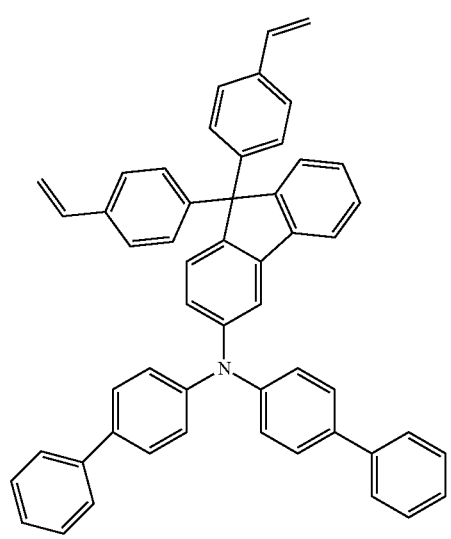 [SMILES: C=Cc1ccc(C2(c3ccc(C=C)cc3)c3ccccc3-c3cc(N(c4ccc(-c5ccccc5)cc4)c4ccc(-c5ccccc5)cc4)ccc32)cc1]
13
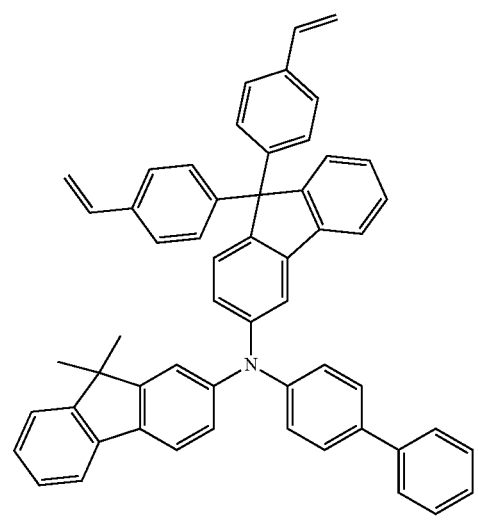 [SMILES: C=Cc1ccc(C2(c3ccc(C=C)cc3)c3ccccc3-c3cc(N(c4ccc(-c5ccccc5)cc4)c4ccc5c(c4)C(C)(C)c4ccccc4-5)ccc32)cc1]
14

-continued
15
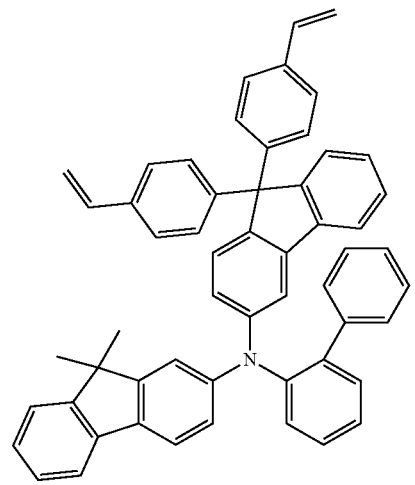 [SMILES: C=Cc1ccc(C2(c3ccc(C=C)cc3)c3ccccc3-c3cc(N(c4ccc5c(c4)C(C)(C)c4ccccc4-5)c4ccccc4-c4ccccc4)ccc32)cc1]
16
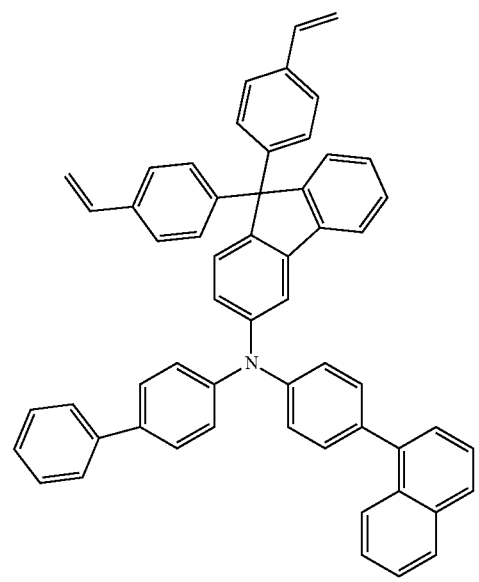 [SMILES: C=Cc1ccc(C2(c3ccc(C=C)cc3)c3ccccc3-c3cc(N(c4ccc(-c5ccccc5)cc4)c4ccc(-c5cccc6ccccc56)cc4)ccc32)cc1]

17
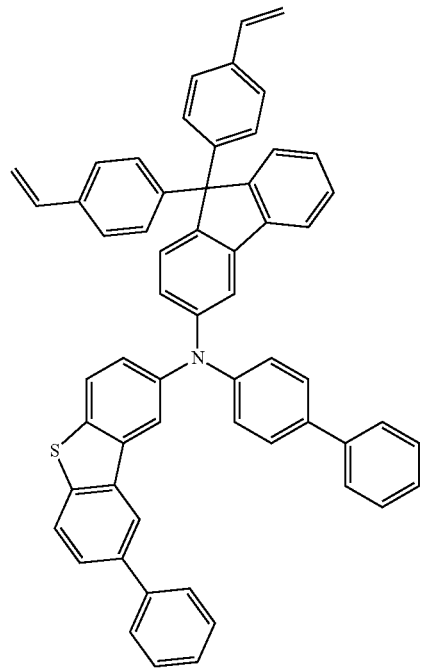 [SMILES: C=Cc1ccc(C2(c3ccc(C=C)cc3)c3ccccc3-c3cc(N(c4ccc(-c5ccccc5)cc4)c4ccc5sc6ccc(-c7ccccc7)cc6c5c4)ccc32)cc1]
18
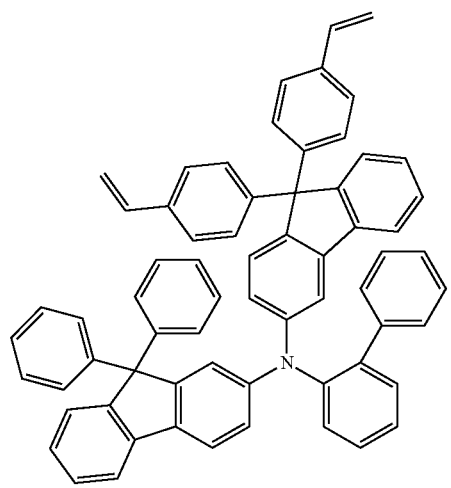 [SMILES: C=Cc1ccc(C2(c3ccc(C=C)cc3)c3ccccc3-c3cc(N(c4ccc5c(c4)C(c4ccccc4)(c4ccccc4)c4ccccc4-5)c4ccccc4-c4ccccc4)ccc32)cc1]

-continued
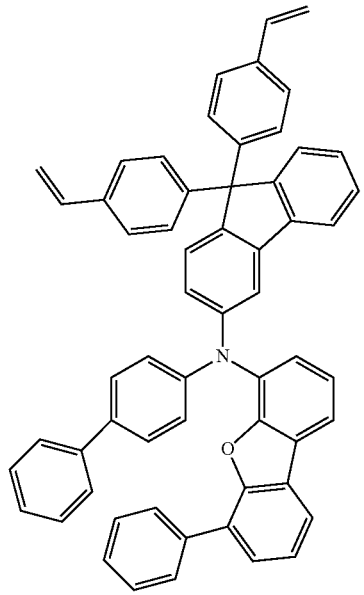 [SMILES: C=Cc1ccc(C2(c3ccc(C=C)cc3)c3ccccc3-c3cc(N(c4ccc(-c5ccccc5)cc4)c4cccc5c4oc4c(-c6ccccc6)cccc45)ccc32)cc1]
19
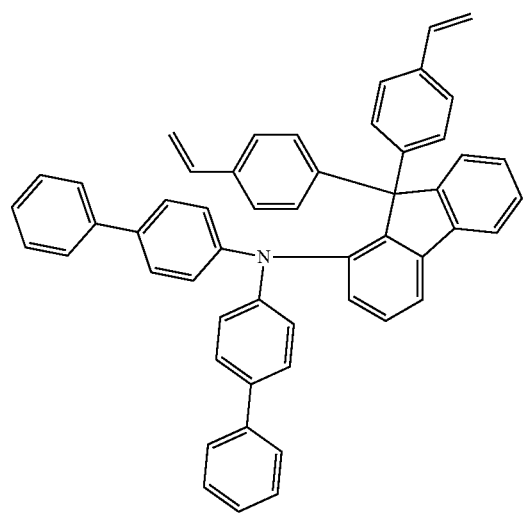 [SMILES: C=Cc1ccc(C2(c3ccc(C=C)cc3)c3ccccc3-c3cccc(CN(c4ccc(-c5ccccc5)cc4)c4ccc(-c5ccccc5)cc4)c32)cc1]
20
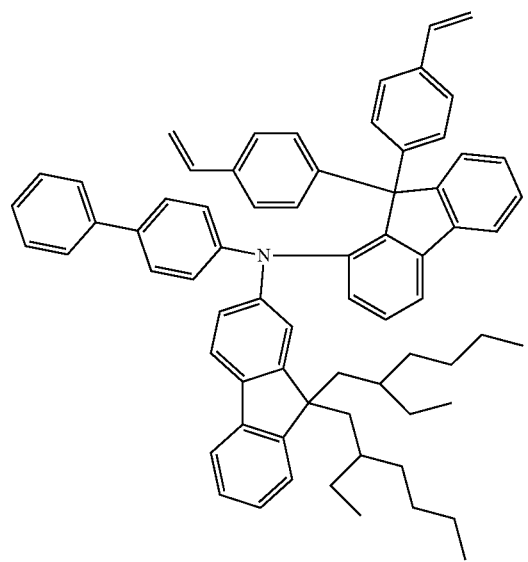 [SMILES: C=Cc1ccc(C2(c3ccc(C=C)cc3)c3ccccc3-c3cccc(CN(c4ccc(-c5ccccc5)cc4)c4ccc5c(c4)C(CC(CC)CCCC)(CC(CC)CCCC)c4ccccc4-5)c32)cc1]
21

22
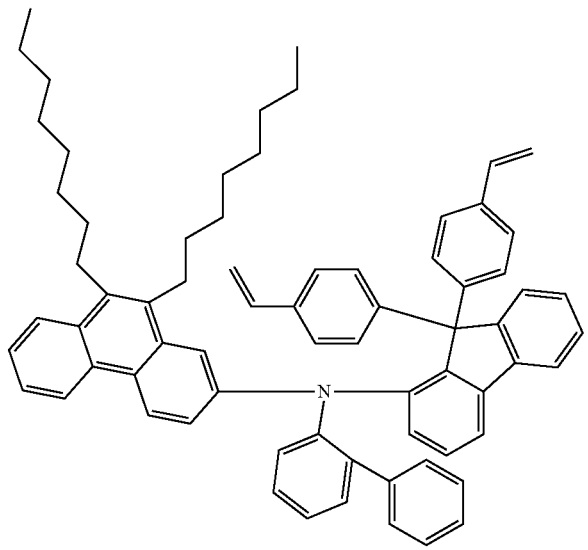 [SMILES: C=Cc1ccc(C2(c3ccc(C=C)cc3)c3ccccc3-c3cccc(CN(c4ccc5c(c4)c(CCCCCCCC)c(CCCCCCCC)c4ccccc45)c4ccccc4-c4ccccc4)c32)cc1]
23
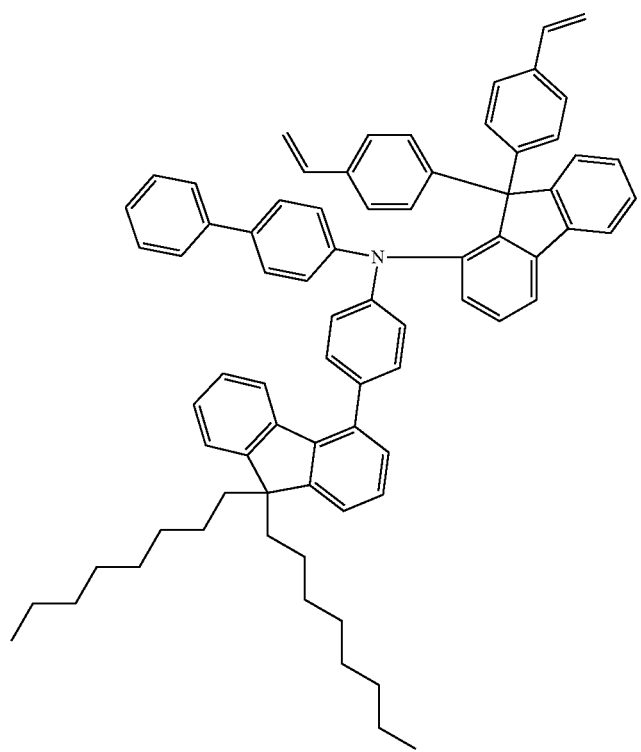 [SMILES: C=Cc1ccc(C2(c3ccc(C=C)cc3)c3ccccc3-c3cccc(CN(c4ccc(-c5ccccc5)cc4)c4ccc(-c5cccc6c5-c5ccccc5C6(CCCCCCCC)CCCCCCCC)cc4)c32)cc1]

-continued
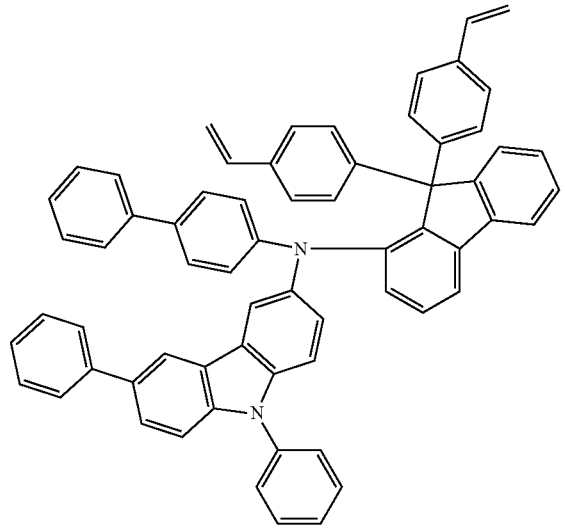 [SMILES: C=Cc1ccc(C2(c3ccc(C=C)cc3)c3ccccc3-c3cccc(CN(c4ccc(-c5ccccc5)cc4)c4ccc5c(c4)c4cc(-c6ccccc6)ccc4n5-c4ccccc4)c32)cc1]
24
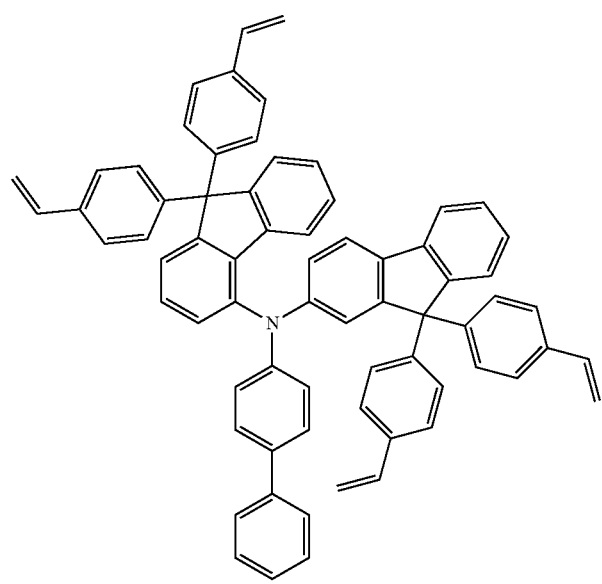 [SMILES: C=Cc1ccc(C2(c3ccc(C=C)cc3)c3ccccc3-c3ccc(N(c4ccc(-c5ccccc5)cc4)c4cccc5c4-c4ccccc4C5(c4ccc(C=C)cc4)c4ccc(C=C)cc4)cc32)cc1]
25

-continued
26
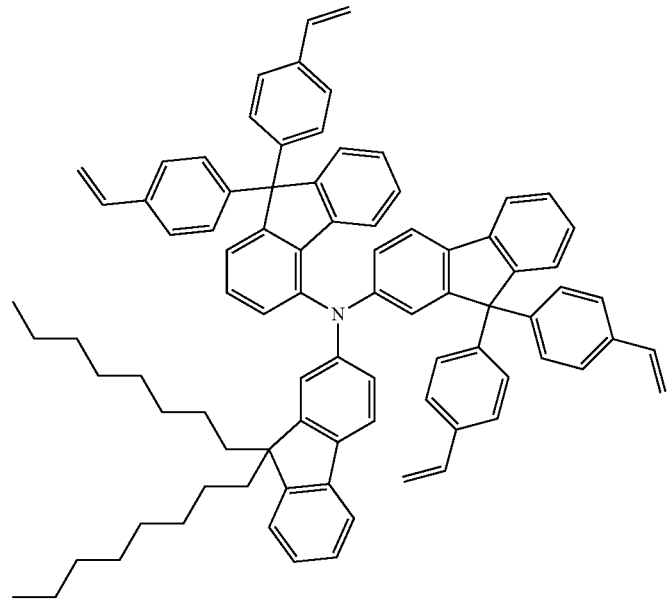 [SMILES: C=Cc1ccc(C2(c3ccc(C=C)cc3)c3ccccc3-c3ccc(N(c4ccc5c(c4)C(CCCCCCCC)(CCCCCCCC)c4ccccc4-5)c4cccc5c4-c4ccccc4C5(c4ccc(C=C)cc4)c4ccc(C=C)cc4)cc32)cc1]
27
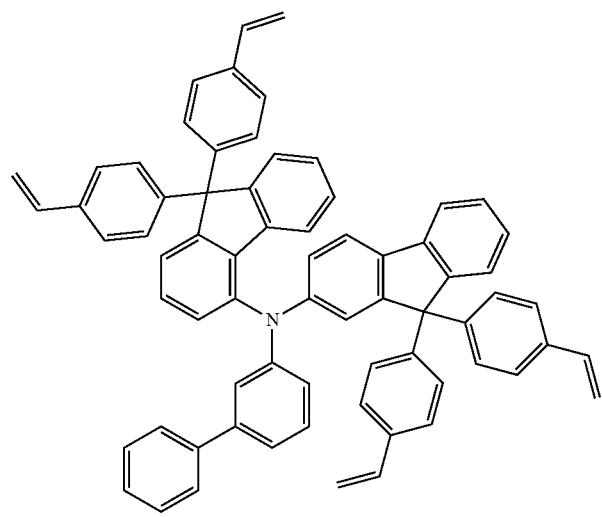 [SMILES: C=Cc1ccc(C2(c3ccc(C=C)cc3)c3ccccc3-c3ccc(N(c4cccc(-c5ccccc5)c4)c4cccc5c4-c4ccccc4C5(c4ccc(C=C)cc4)c4ccc(C=C)cc4)cc32)cc1]
28
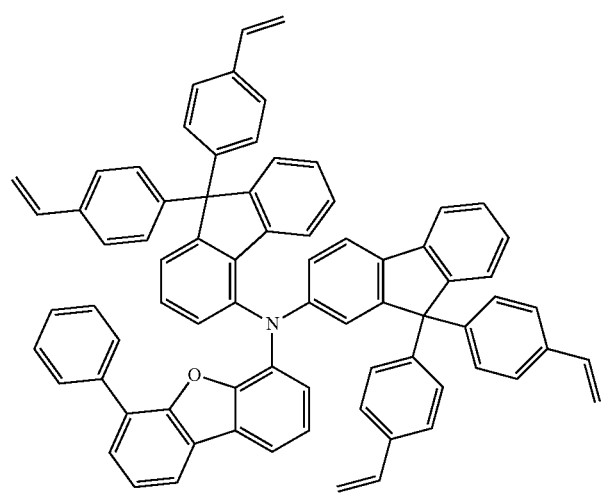 [SMILES: C=Cc1ccc(C2(c3ccc(C=C)cc3)c3ccccc3-c3ccc(N(c4cccc5c4-c4ccccc4C5(c4ccc(C=C)cc4)c4ccc(C=C)cc4)c4cccc5c4oc4c(-c6ccccc6)cccc45)cc32)cc1]

29
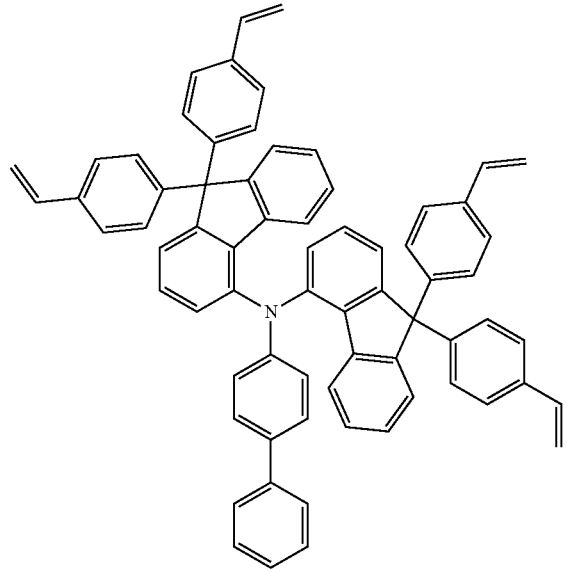 [SMILES: C=Cc1ccc(C2(c3ccc(C=C)cc3)c3ccccc3-c3c(N(c4ccc(-c5ccccc5)cc4)c4cccc5c4-c4ccccc4C5(c4ccc(C=C)cc4)c4ccc(C=C)cc4)cccc32)cc1]
30
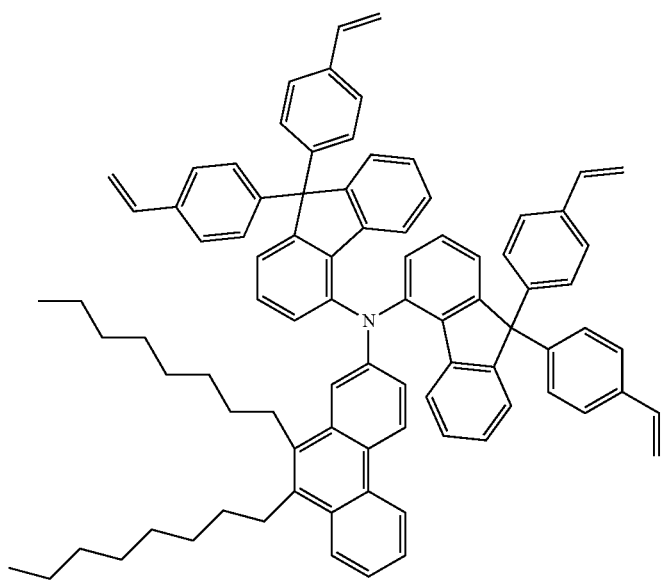 [SMILES: C=Cc1ccc(C2(c3ccc(C=C)cc3)c3ccccc3-c3c(N(c4ccc5c(c4)c(CCCCCCCC)c(CCCCCCCC)c4ccccc45)c4cccc5c4-c4ccccc4C5(c4ccc(C=C)cc4)c4ccc(C=C)cc4)cccc32)cc1]

31
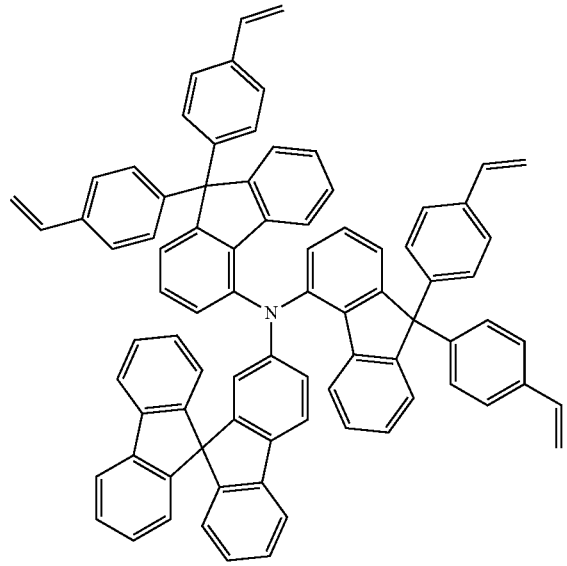 [SMILES: C=Cc1ccc(C2(c3ccc(C=C)cc3)c3ccccc3-c3c(N(c4ccc5c(c4)C4(c6ccccc6-c6ccccc64)c4ccccc4-5)c4cccc5c4-c4ccccc4C5(c4ccc(C=C)cc4)c4ccc(C=C)cc4)cccc32)cc1]
32
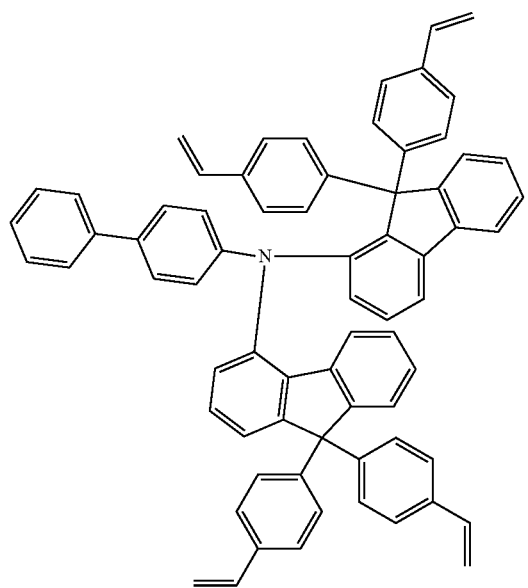 [SMILES: C=Cc1ccc(C2(c3ccc(C=C)cc3)c3ccccc3-c3c(N(c4ccc(-c5ccccc5)cc4)c4cccc5c4C(c4ccc(C=C)cc4)(c4ccc(C=C)cc4)c4ccccc4-5)cccc32)cc1]

-continued
33
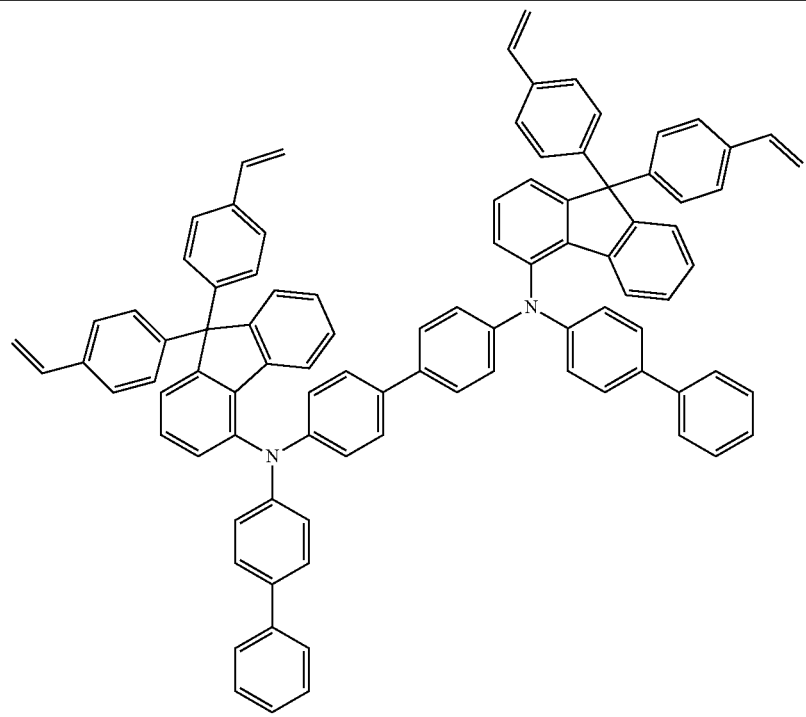
34
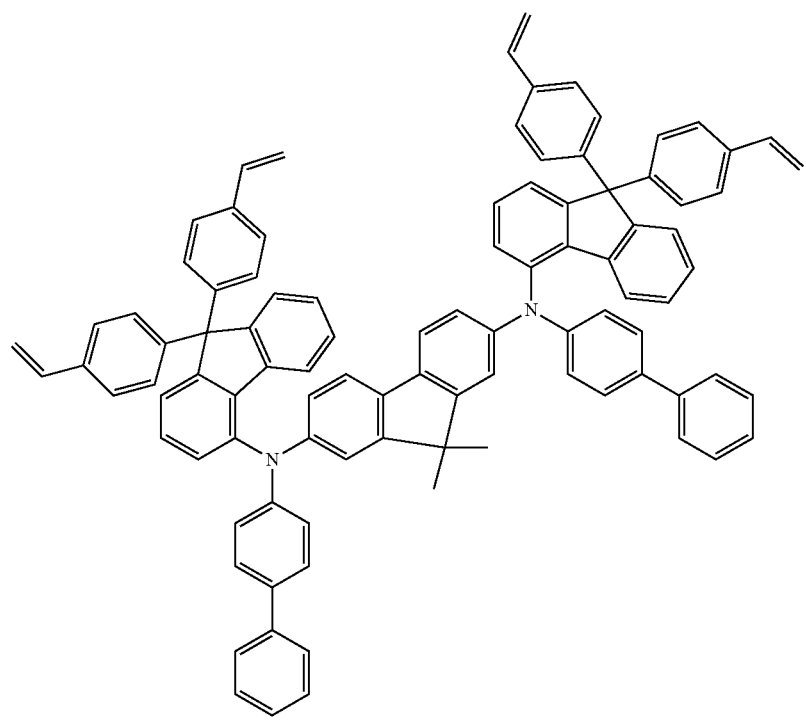 [SMILES: C=Cc1ccc(C2(c3ccc(C=C)cc3)c3ccccc3-c3c(N(c4ccc(-c5ccccc5)cc4)c4ccc5c(c4)C(C)(C)c4cc(N(c6ccc(-c7ccccc7)cc6)c6cccc7c6-c6ccccc6C7(c6ccc(C=C)cc6)c6ccc(C=C)cc6)ccc4-5)cccc32)cc1]

35
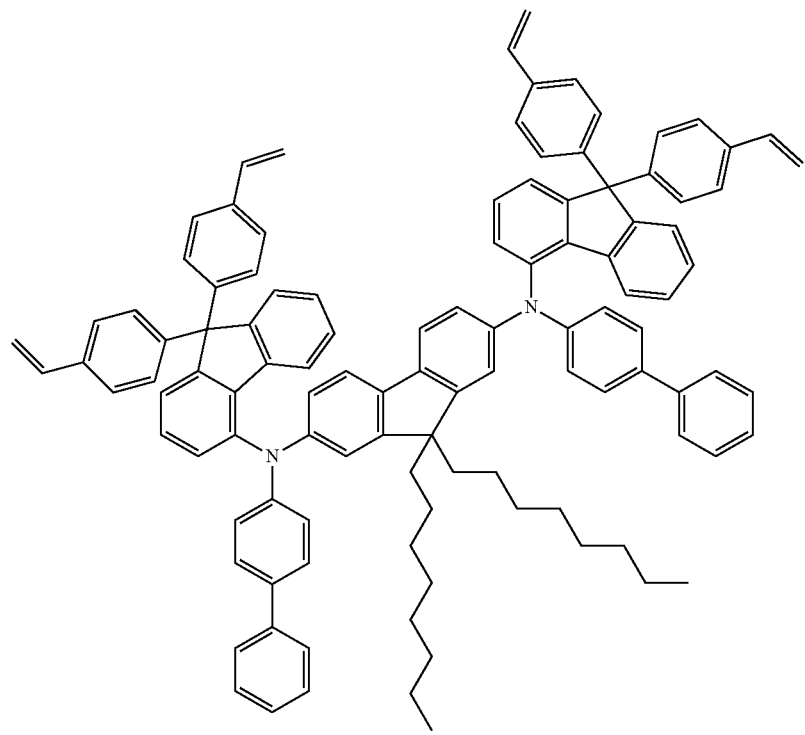 [SMILES: C=Cc1ccc(C2(c3ccc(C=C)cc3)c3ccccc3-c3c(N(c4ccc(-c5ccccc5)cc4)c4ccc5c(c4)C(CCCCCCCC)(CCCCCCCC)c4cc(N(c6ccc(-c7ccccc7)cc6)c6cccc7c6-c6ccccc6C7(c6ccc(C=C)cc6)c6ccc(C=C)cc6)ccc4-5)cccc32)cc1]
36
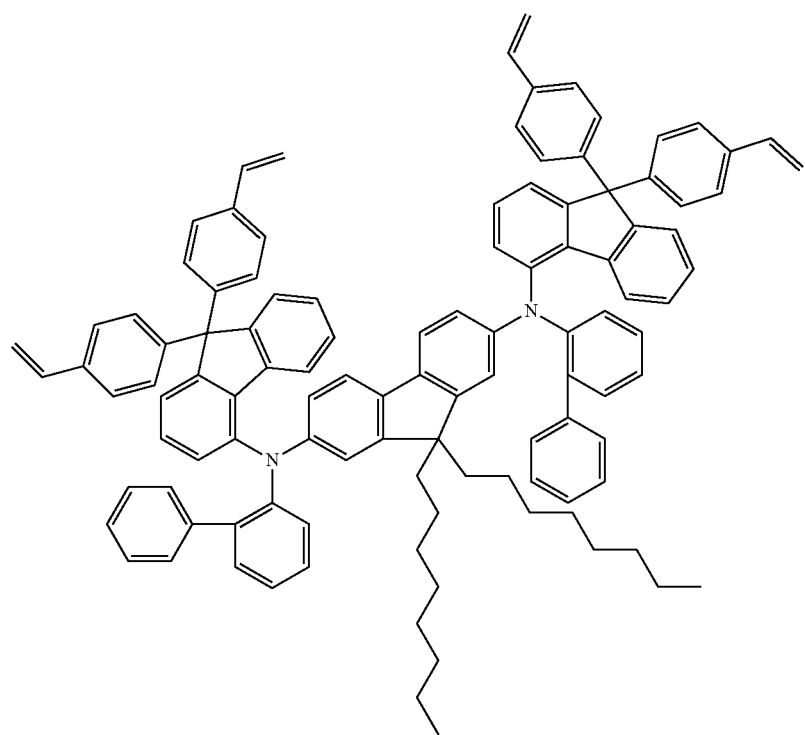 [SMILES: C=Cc1ccc(C2(c3ccc(C=C)cc3)c3ccccc3-c3c(N(c4ccc5c(c4)C(CCCCCCCC)(CCCCCCCC)c4cc(N(c6ccccc6-c6ccccc6)c6cccc7c6-c6ccccc6C7(c6ccc(C=C)cc6)c6ccc(C=C)cc6)ccc4-5)c4ccccc4-c4ccccc4)cccc32)cc1]

-continued
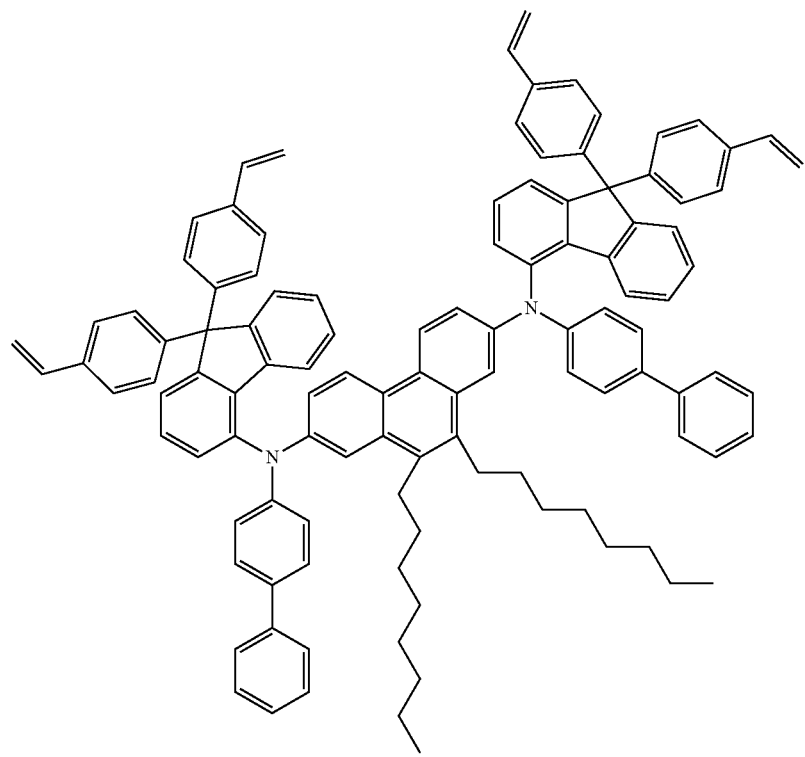 [SMILES: C=Cc1ccc(C2(c3ccc(C=C)cc3)c3ccccc3-c3c(N(c4ccc(-c5ccccc5)cc4)c4ccc5c(c4)c(CCCCCCCC)c(CCCCCCCC)c4cc(N(c6ccc(-c7ccccc7)cc6)c6cccc7c6-c6ccccc6C7(c6ccc(C=C)cc6)c6ccc(C=C)cc6)ccc45)cccc32)cc1]
37
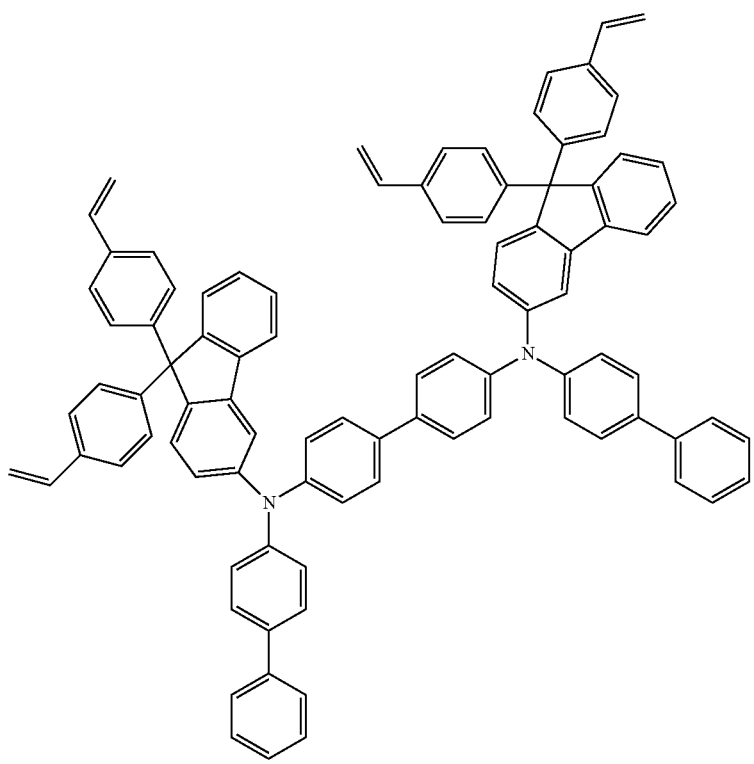 [SMILES: C=Cc1ccc(C2(c3ccc(C=C)cc3)c3ccccc3-c3cc(N(c4ccc(-c5ccccc5)cc4)c4ccc(-c5ccc(N(c6ccc(-c7ccccc7)cc6)c6ccc7c(c6)-c6ccccc6C7(c6ccc(C=C)cc6)c6ccc(C=C)cc6)cc5)cc4)ccc32)cc1]
38

-continued
39
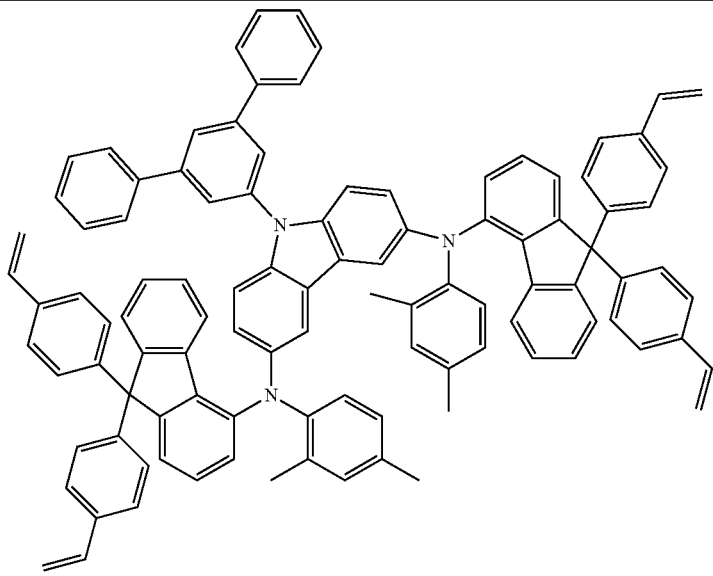
40
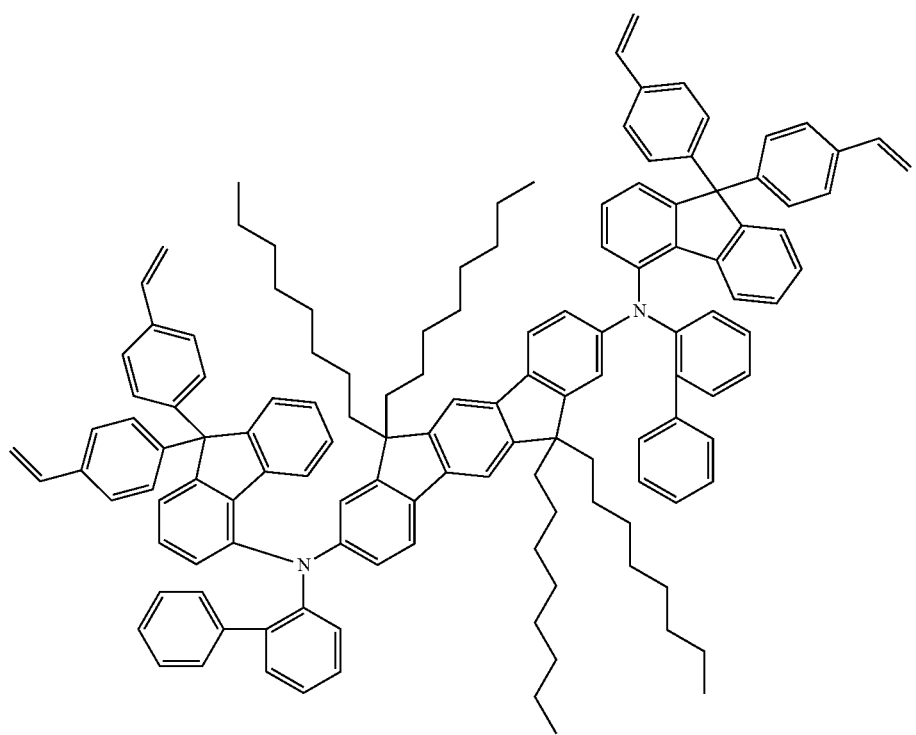 [SMILES: C=Cc1ccc(C2(c3ccc(C=C)cc3)c3ccccc3-c3c(N(c4ccc5c(c4)C(CCCCCCCC)(CCCCCCCC)c4cc6c(cc4-5)C(CCCCCCCC)(CCCCCCCC)c4cc(N(c5ccccc5-c5ccccc5)c5cccc7c5-c5ccccc5C7(c5ccc(C=C)cc5)c5ccc(C=C)cc5)ccc4-6)c4ccccc4-c4ccccc4)cccc32)cc1]

41
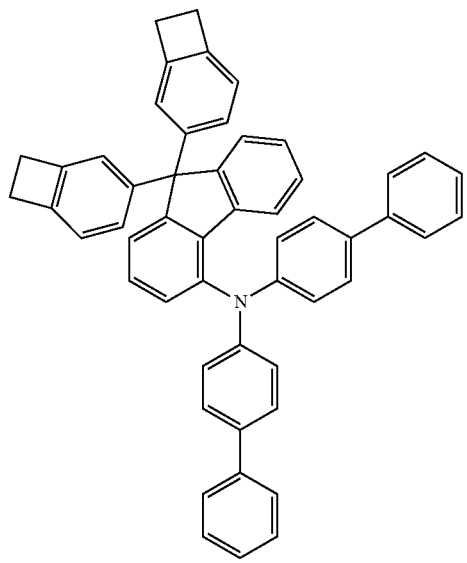 [SMILES: c1ccc(-c2ccc(N(c3ccc(-c4ccccc4)cc3)c3cccc4c3-c3ccccc3C4(c3ccc4c(c3)CC4)c3ccc4c(c3)CC4)cc2)cc1]
42
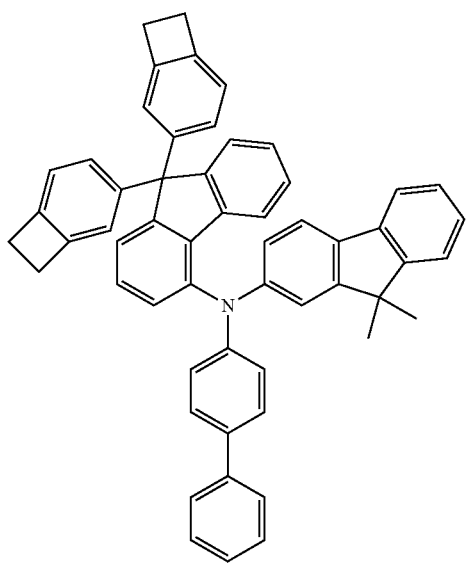 [SMILES: CC1(C)c2ccccc2-c2ccc(N(c3ccc(-c4ccccc4)cc3)c3cccc4c3-c3ccccc3C4(c3ccc4c(c3)CC4)c3ccc4c(c3)CC4)cc21]
43
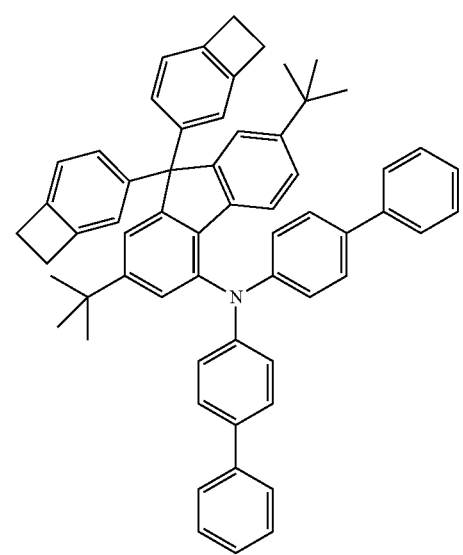 [SMILES: CC(C)(C)c1ccc2c(c1)C(c1ccc3c(c1)CC3)(c1ccc3c(c1)CC3)c1cc(C(C)(C)C)cc(N(c3ccc(-c4ccccc4)cc3)c3ccc(-c4ccccc4)cc3)c1-2]

-continued
44
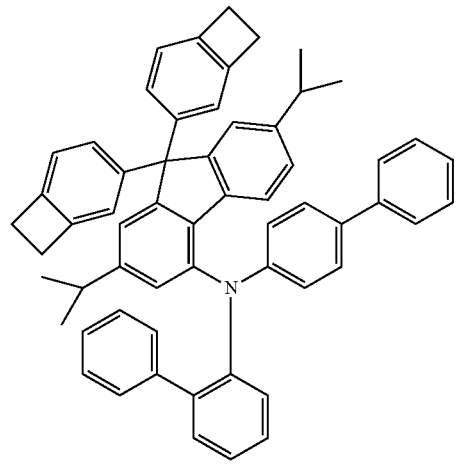 [SMILES: CC(C)c1ccc2c(c1)C(c1ccc3c(c1)CC3)(c1ccc3c(c1)CC3)c1cc(C(C)C)cc(N(c3ccc(-c4ccccc4)cc3)c3ccccc3-c3ccccc3)c1-2]
45
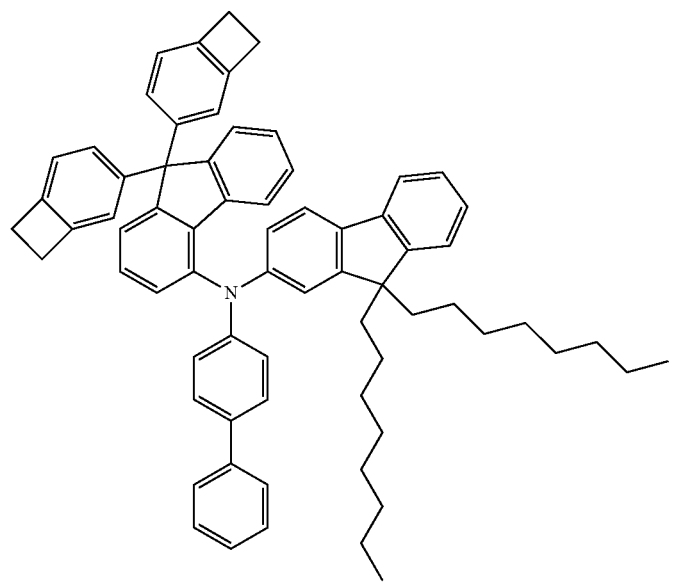 [SMILES: CCCCCCCCC1(CCCCCCCC)c2ccccc2-c2ccc(N(c3ccc(-c4ccccc4)cc3)c3cccc4c3-c3ccccc3C4(c3ccc4c(c3)CC4)c3ccc4c(c3)CC4)cc21]

46
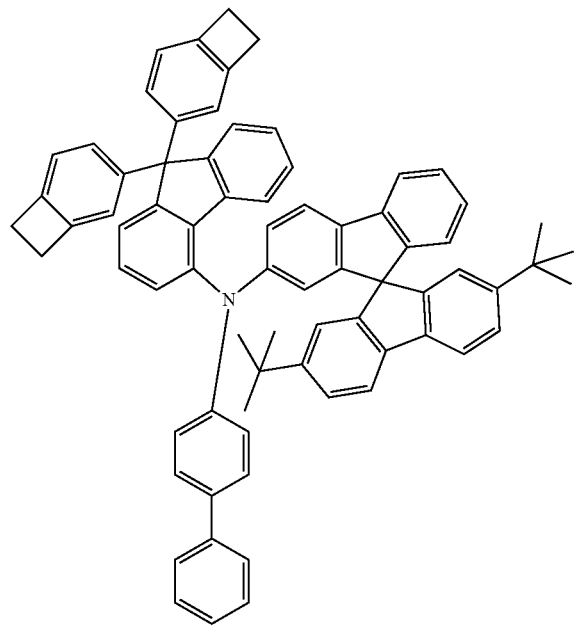 [SMILES: CC(C)(C)c1ccc2c(c1)C1(c3ccccc3-c3ccc(N(c4ccc(-c5ccccc5)cc4)c4cccc5c4-c4ccccc4C5(c4ccc5c(c4)CC5)c4ccc5c(c4)CC5)cc31)c1cc(C(C)(C)C)ccc1-2]
47
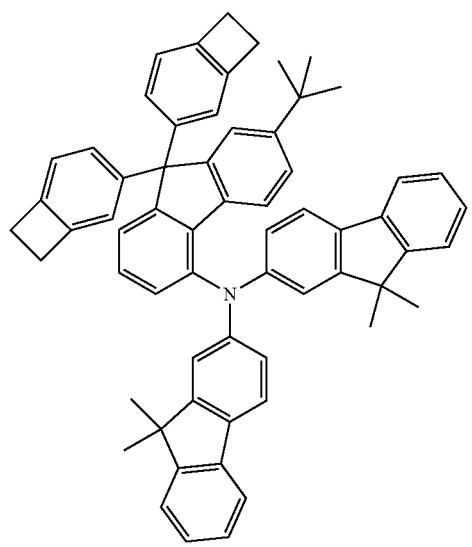 [SMILES: CC(C)(C)c1ccc2c(c1)C(c1ccc3c(c1)CC3)(c1ccc3c(c1)CC3)c1cccc(N(c3ccc4c(c3)C(C)(C)c3ccccc3-4)c3ccc4c(c3)C(C)(C)c3ccccc3-4)c1-2]
48
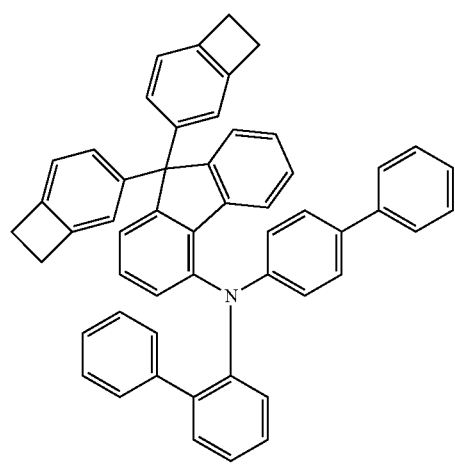 [SMILES: c1ccc(-c2ccc(N(c3ccccc3-c3ccccc3)c3cccc4c3-c3ccccc3C4(c3ccc4c(c3)CC4)c3ccc4c(c3)CC4)cc2)cc1]

-continued
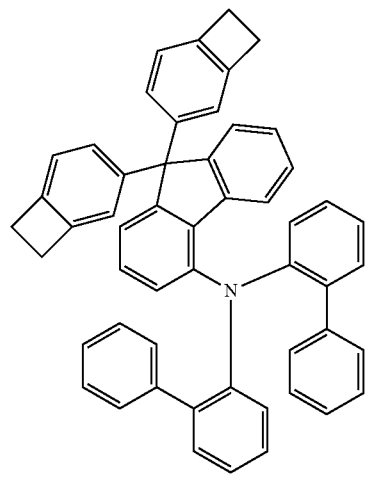 [SMILES: c1ccc(-c2ccccc2N(c2ccccc2-c2ccccc2)c2cccc3c2-c2ccccc2C3(c2ccc3c(c2)CC3)c2ccc3c(c2)CC3)cc1]
49
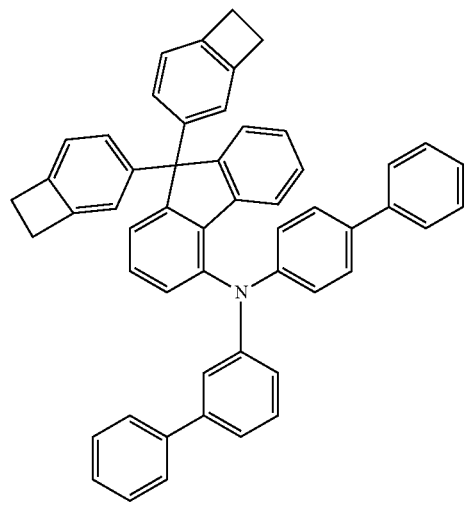 [SMILES: c1ccc(-c2ccc(N(c3cccc(-c4ccccc4)c3)c3cccc4c3-c3ccccc3C4(c3ccc4c(c3)CC4)c3ccc4c(c3)CC4)cc2)cc1]
50
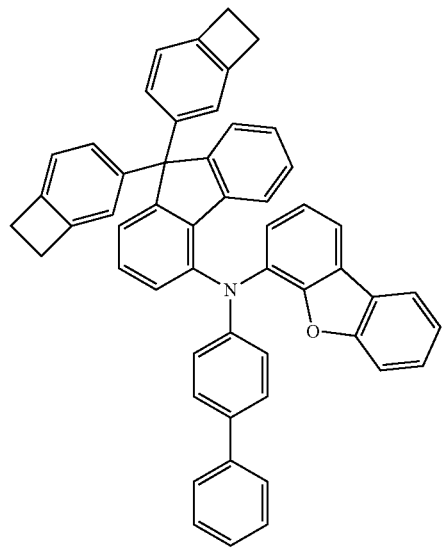 [SMILES: c1ccc(-c2ccc(N(c3cccc4c3-c3ccccc3C4(c3ccc4c(c3)CC4)c3ccc4c(c3)CC4)c3cccc4c3oc3ccccc34)cc2)cc1]
51

-continued
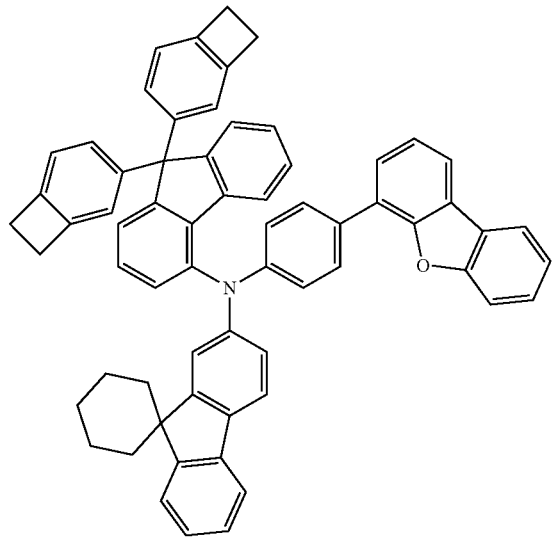 [SMILES: c1ccc2c(c1)-c1ccc(N(c3ccc(-c4cccc5c4oc4ccccc45)cc3)c3cccc4c3-c3ccccc3C4(c3ccc4c(c3)CC4)c3ccc4c(c3)CC4)cc1C21CCCCC1]
52
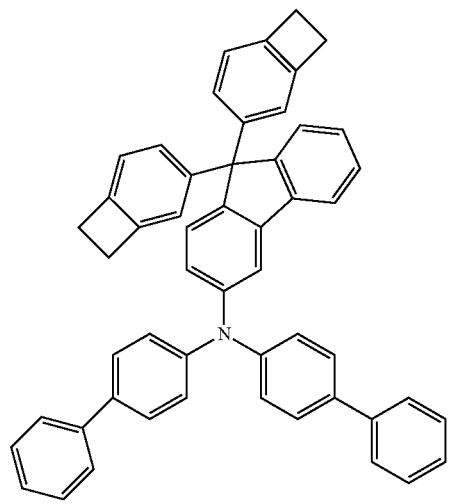 [SMILES: c1ccc(-c2ccc(N(c3ccc(-c4ccccc4)cc3)c3ccc4c(c3)-c3ccccc3C4(c3ccc4c(c3)CC4)c3ccc4c(c3)CC4)cc2)cc1]
53
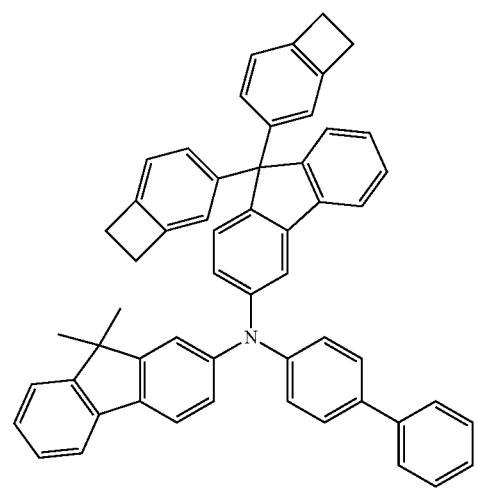 [SMILES: CC1(C)c2ccccc2-c2ccc(N(c3ccc(-c4ccccc4)cc3)c3ccc4c(c3)-c3ccccc3C4(c3ccc4c(c3)CC4)c3ccc4c(c3)CC4)cc21]
54

55
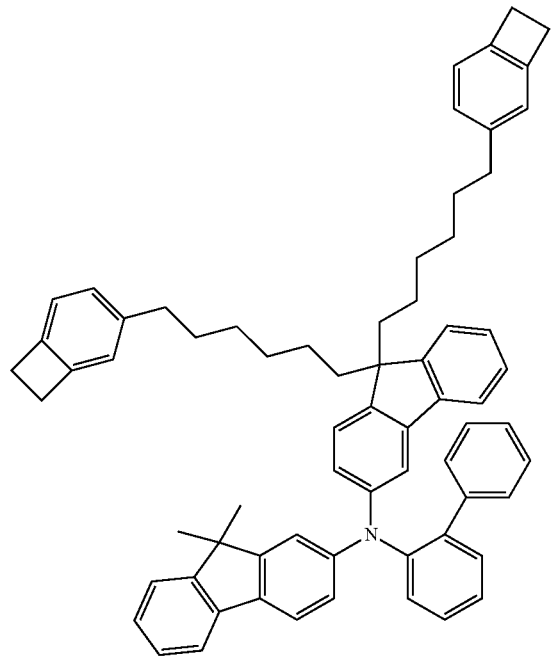 [SMILES: CC1(C)c2ccccc2-c2ccc(N(c3ccc4c(c3)-c3ccccc3C4(CCCCCCc3ccc4c(c3)CC4)CCCCCCc3ccc4c(c3)CC4)c3ccccc3-c3ccccc3)cc21]
56
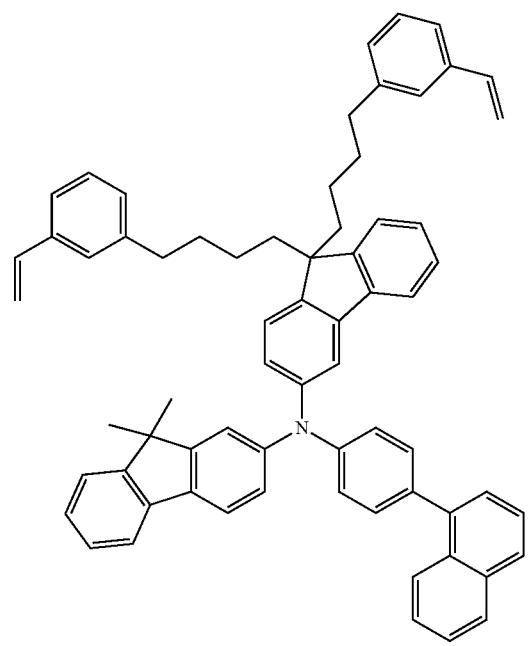 [SMILES: C=Cc1cccc(CCCCC2(CCCCc3cccc(C=C)c3)c3ccccc3-c3cc(N(c4ccc(-c5cccc6ccccc56)cc4)c4ccc5c(c4)C(C)(C)c4ccccc4-5)ccc32)c1]

-continued
57
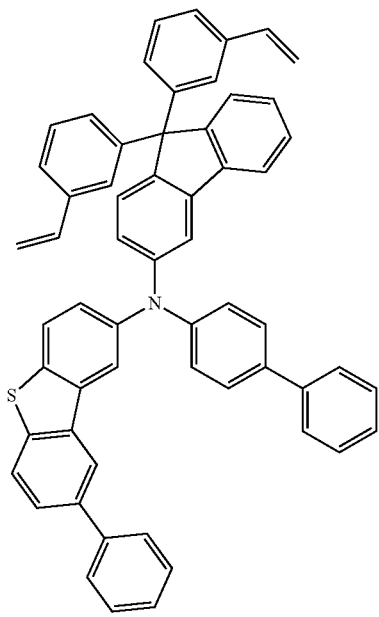 [SMILES: C=Cc1cccc(C2(c3cccc(C=C)c3)c3ccccc3-c3cc(N(c4ccc(-c5ccccc5)cc4)c4ccc5sc6ccc(-c7ccccc7)cc6c5c4)ccc32)c1]
58
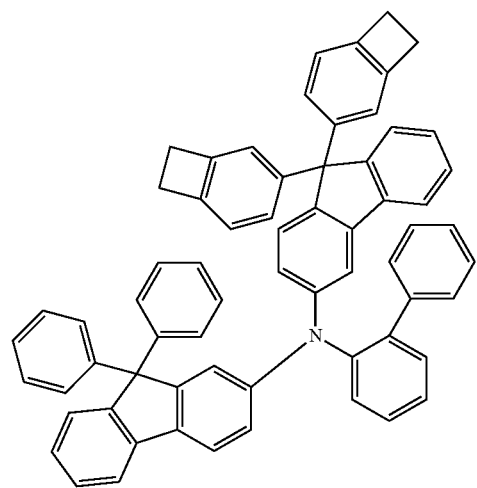 [SMILES: c1ccc(-c2ccccc2N(c2ccc3c(c2)-c2ccccc2C3(c2ccc3c(c2)CC3)c2ccc3c(c2)CC3)c2ccc3c(c2)C(c2ccccc2)(c2ccccc2)c2ccccc2-3)cc1]

-continued
59
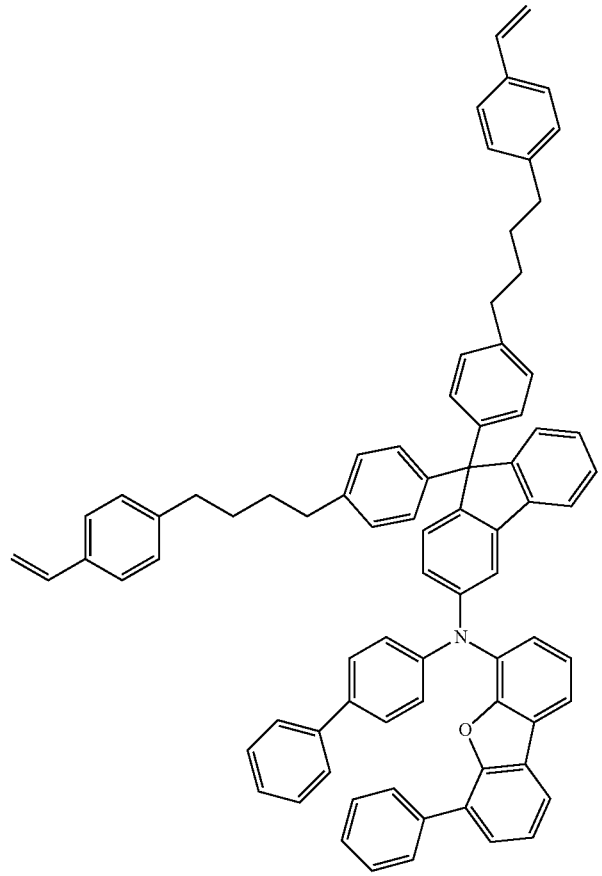 [SMILES: C=Cc1ccc(CCCCc2ccc(C3(c4ccc(CCCCc5ccc(C=C)cc5)cc4)c4ccccc4-c4cc(N(c5ccc(-c6ccccc6)cc5)c5cccc6c5oc5c(-c7ccccc7)cccc56)ccc43)cc2)cc1]
60
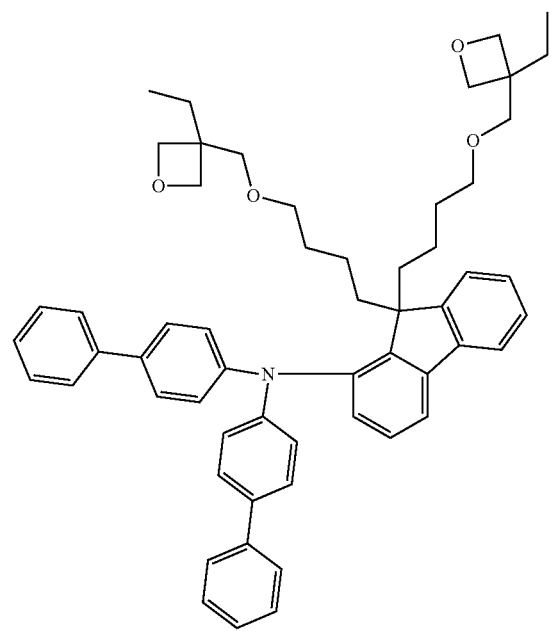 [SMILES: CCC1(COCCCCC2(CCCCOCC3(CC)COC3)c3ccccc3-c3cccc(N(c4ccc(-c5ccccc5)cc4)c4ccc(-c5ccccc5)cc4)c32)COC1]

61
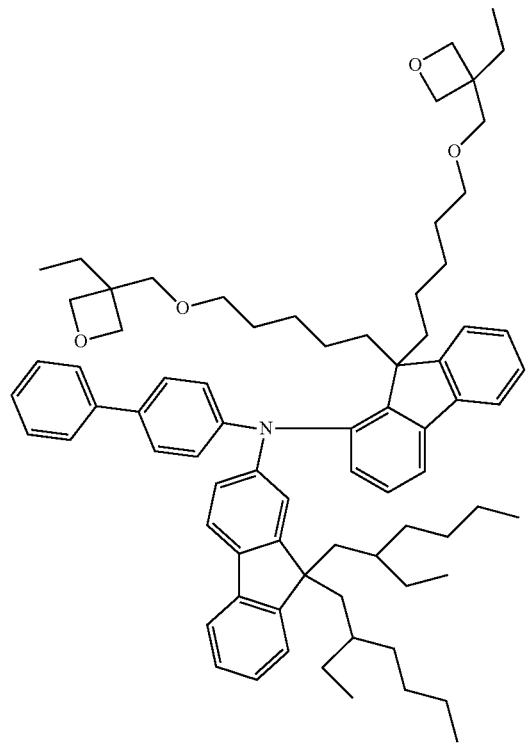 [SMILES: CCCCC(CC)CC1(CC(CC)CCCC)c2ccccc2-c2ccc(N(c3ccc(-c4ccccc4)cc3)c3cccc4c3C(CCCCCOCC3(CC)COC3)(CCCCCOCC3(CC)COC3)c3ccccc3-4)cc21]
62
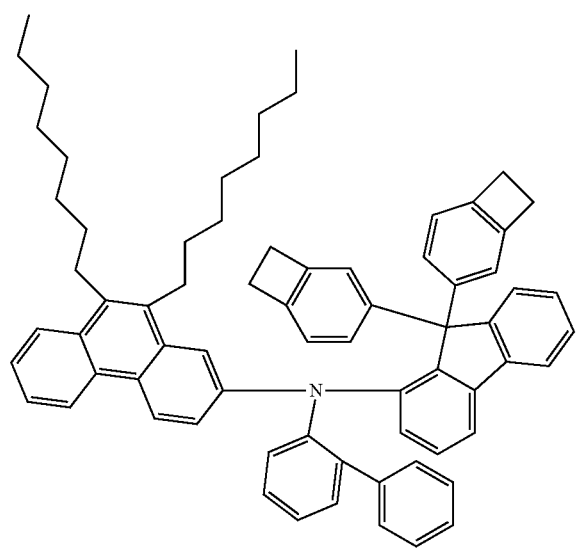 [SMILES: CCCCCCCCc1c(CCCCCCCC)c2cc(N(c3ccccc3-c3ccccc3)c3cccc4c3C(c3ccc5c(c3)CC5)(c3ccc5c(c3)CC5)c3ccccc3-4)ccc2c2ccccc12]

-continued
63
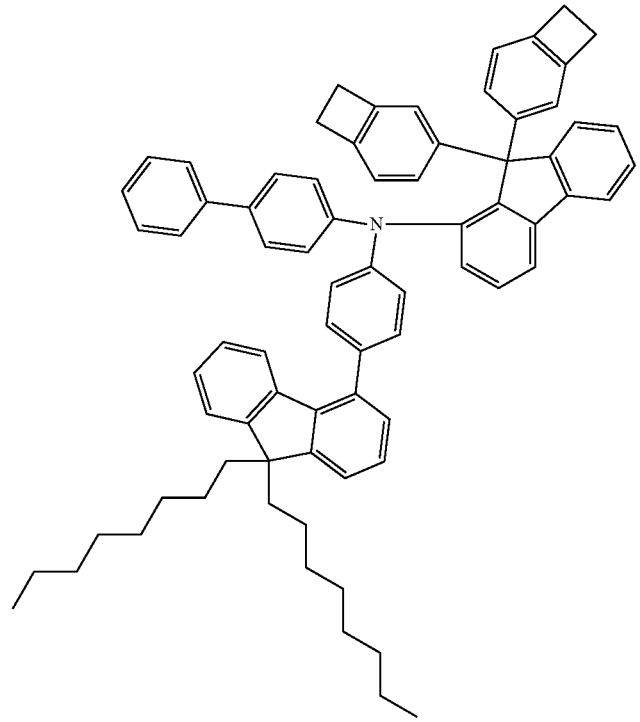 [SMILES: CCCCCCCCC1(CCCCCCCC)c2ccccc2-c2c(-c3ccc(N(c4ccc(-c5ccccc5)cc4)c4cccc5c4C(c4ccc6c(c4)CC6)(c4ccc6c(c4)CC6)c4ccccc4-5)cc3)cccc21]
64
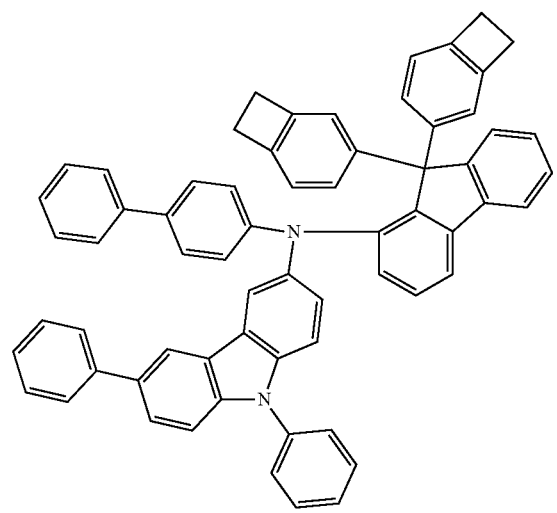 [SMILES: c1ccc(-c2ccc(N(c3ccc4c(c3)c3cc(-c5ccccc5)ccc3n4-c3ccccc3)c3cccc4c3C(c3ccc5c(c3)CC5)(c3ccc5c(c3)CC5)c3ccccc3-4)cc2)cc1]

65
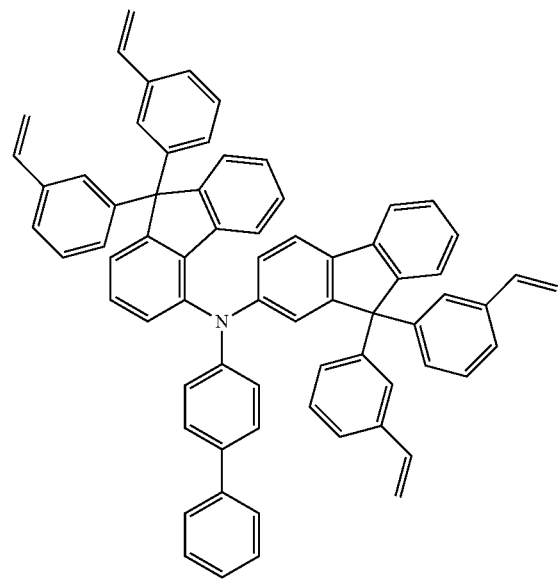 [SMILES: C=Cc1cccc(C2(c3cccc(C=C)c3)c3ccccc3-c3ccc(N(c4ccc(-c5ccccc5)cc4)c4cccc5c4-c4ccccc4C5(c4cccc(C=C)c4)c4cccc(C=C)c4)cc32)c1]
66
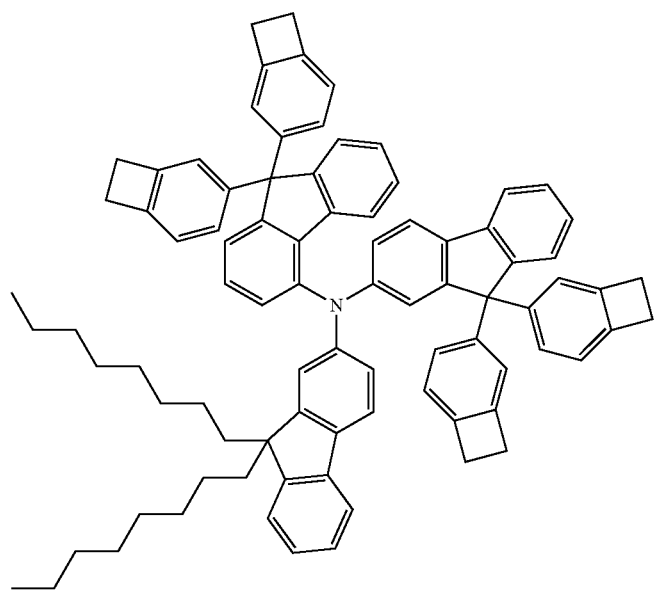 [SMILES: CCCCCCCCC1(CCCCCCCC)c2ccccc2-c2ccc(N(c3ccc4c(c3)C(c3ccc5c(c3)CC5)(c3ccc5c(c3)CC5)c3ccccc3-4)c3cccc4c3-c3ccccc3C4(c3ccc4c(c3)CC4)c3ccc4c(c3)CC4)cc21]

-continued
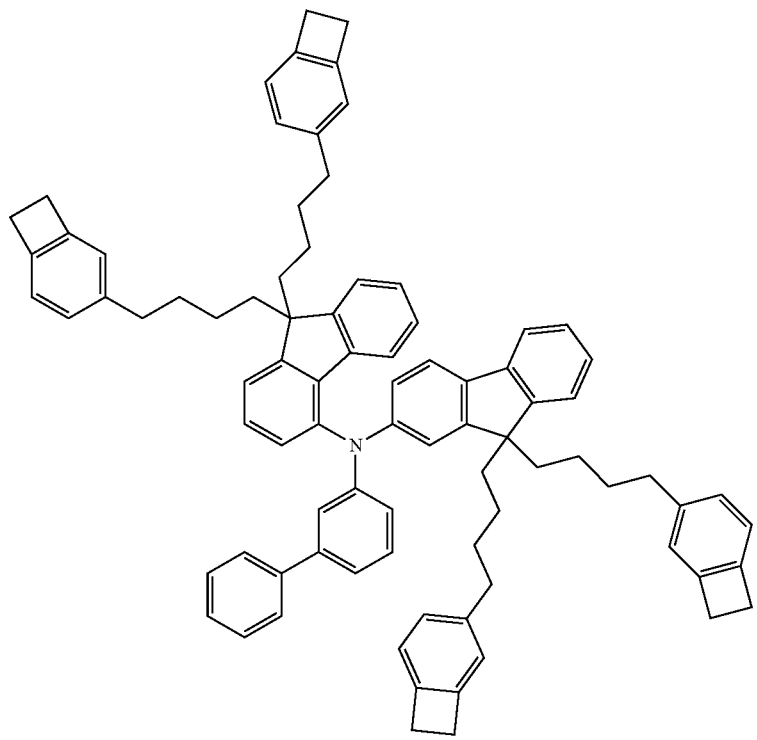 [SMILES: c1ccc(-c2cccc(N(c3ccc4c(c3)C(CCCCc3ccc5c(c3)CC5)(CCCCc3ccc5c(c3)CC5)c3ccccc3-4)c3cccc4c3-c3ccccc3C4(CCCCc3ccc4c(c3)CC4)CCCCc3ccc4c(c3)CC4)c2)cc1]
67
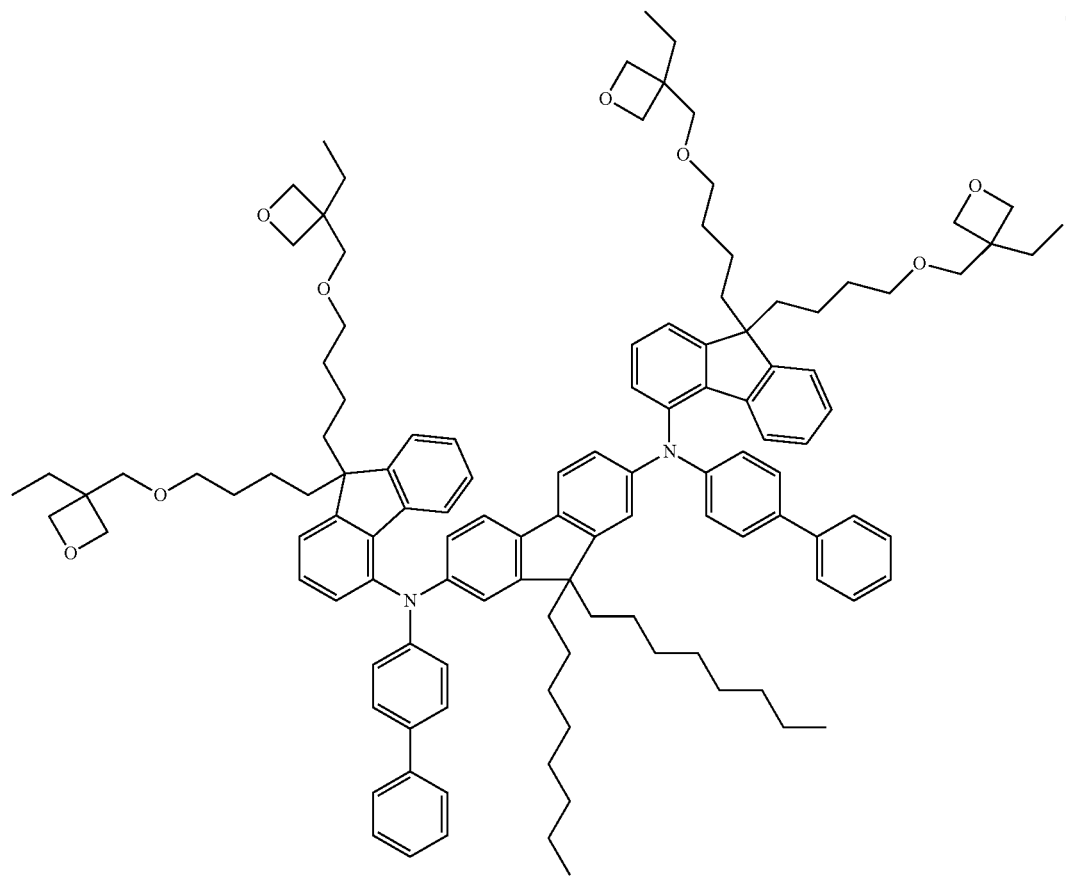 [SMILES: CCCCCCCCC1(CCCCCCCC)c2cc(N(c3ccc(-c4ccccc4)cc3)c3cccc4c3-c3ccccc3C4(CCCCOCC3(CC)COC3)CCCCOCC3(CC)COC3)ccc2-c2ccc(N(c3ccc(-c4ccccc4)cc3)c3cccc4c3-c3ccccc3C4(CCCCOCC3(CC)COC3)CCCCOCC3(CC)COC3)cc21]
68

-continued
69
70
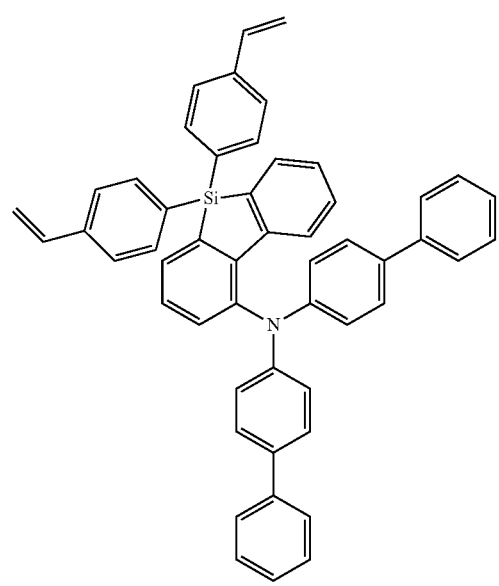 [SMILES: C=Cc1ccc([Si]2(c3ccc(C=C)cc3)c3ccccc3-c3c(N(c4ccc(-c5ccccc5)cc4)c4ccc(-c5ccccc5)cc4)cccc32)cc1]

-continued
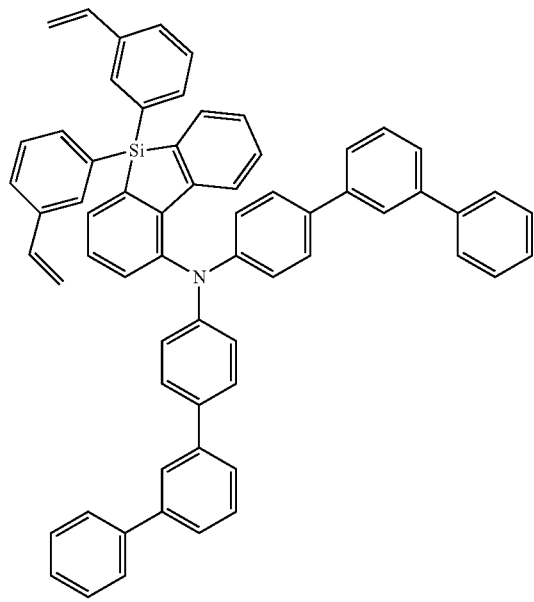 [SMILES: C=Cc1cccc([Si]2(c3cccc(C=C)c3)c3ccccc3-c3c(N(c4ccc(-c5cccc(-c6ccccc6)c5)cc4)c4ccc(-c5cccc(-c6ccccc6)c5)cc4)cccc32)c1]
71
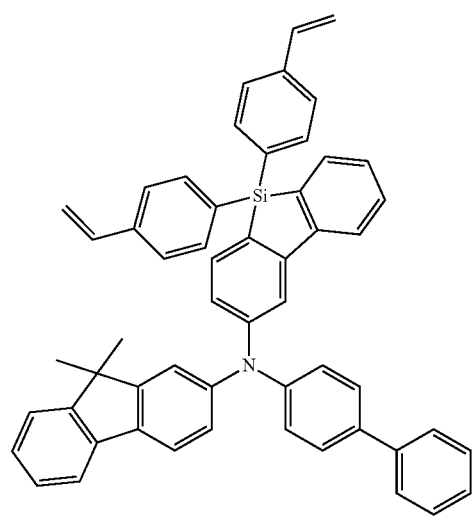 [SMILES: C=Cc1ccc([Si]2(c3ccc(C=C)cc3)c3ccccc3-c3cc(N(c4ccc(-c5ccccc5)cc4)c4ccc5c(c4)C(C)(C)c4ccccc4-5)ccc32)cc1]
72
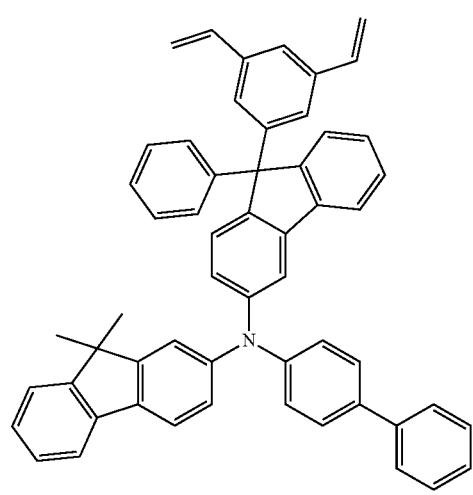 [SMILES: C=Cc1cc(C=C)cc(C2(c3ccccc3)c3ccccc3-c3cc(N(c4ccc(-c5ccccc5)cc4)c4ccc5c(c4)C(C)(C)c4ccccc4-5)ccc32)c1]
73

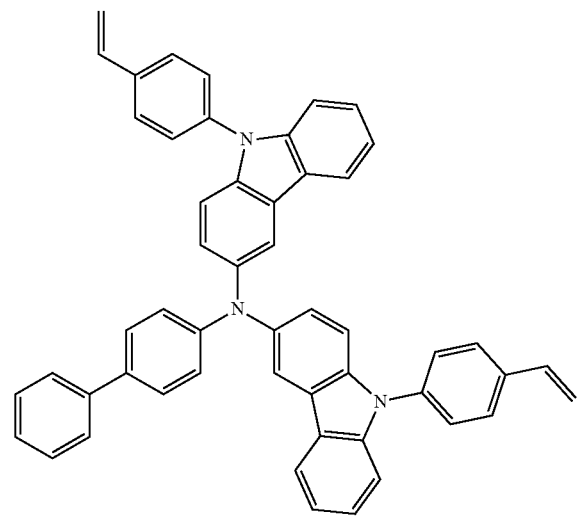 [SMILES: C=Cc1ccc(-n2c3ccccc3c3cc(N(c4ccc(-c5ccccc5)cc4)c4ccc5c(c4)c4ccccc4n5-c4ccc(C=C)cc4)ccc32)cc1]
74
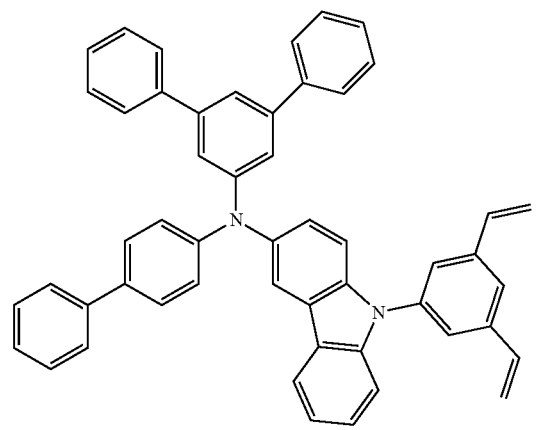 [SMILES: C=Cc1cc(C=C)cc(-n2c3ccccc3c3cc(N(c4ccc(-c5ccccc5)cc4)c4cc(-c5ccccc5)cc(-c5ccccc5)c4)ccc32)c1]
75
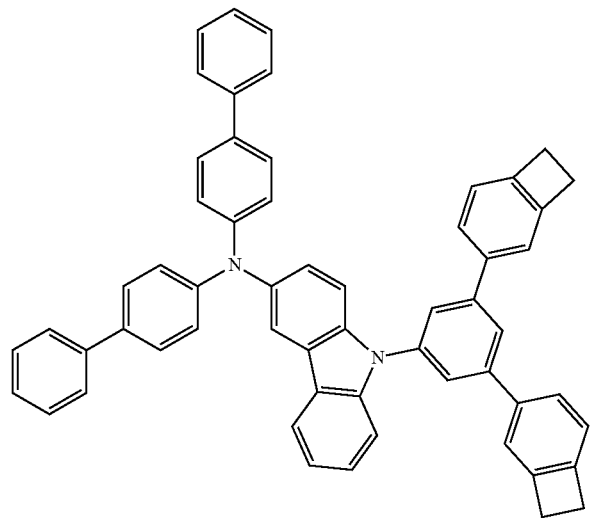 [SMILES: c1ccc(-c2ccc(N(c3ccc(-c4ccccc4)cc3)c3ccc4c(c3)c3ccccc3n4-c3cc(-c4ccc5c(c4)CC5)cc(-c4ccc5c(c4)CC5)c3)cc2)cc1]
76

77
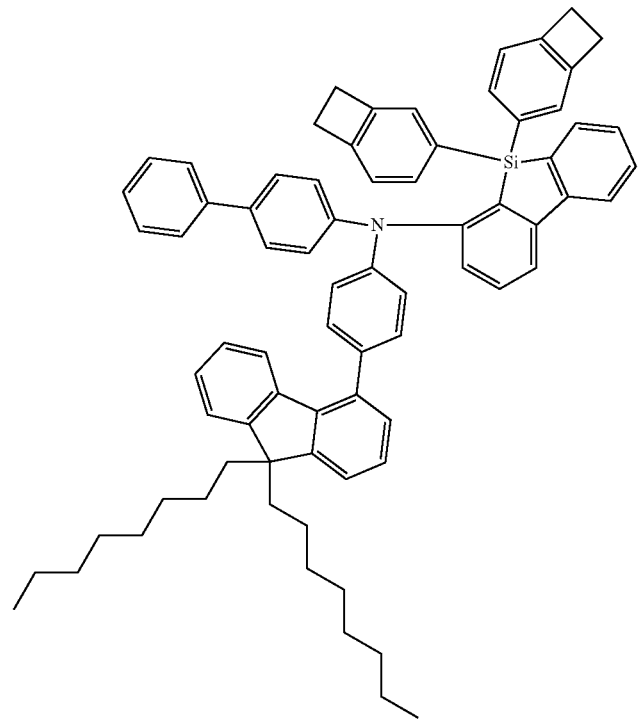 [SMILES: CCCCCCCCC1(CCCCCCCC)c2ccccc2-c2c(-c3ccc(N(c4ccc(-c5ccccc5)cc4)c4cccc5c4[Si](c4ccc6c(c4)CC6)(c4ccc6c(c4)CC6)c4ccccc4-5)cc3)cccc21]
78
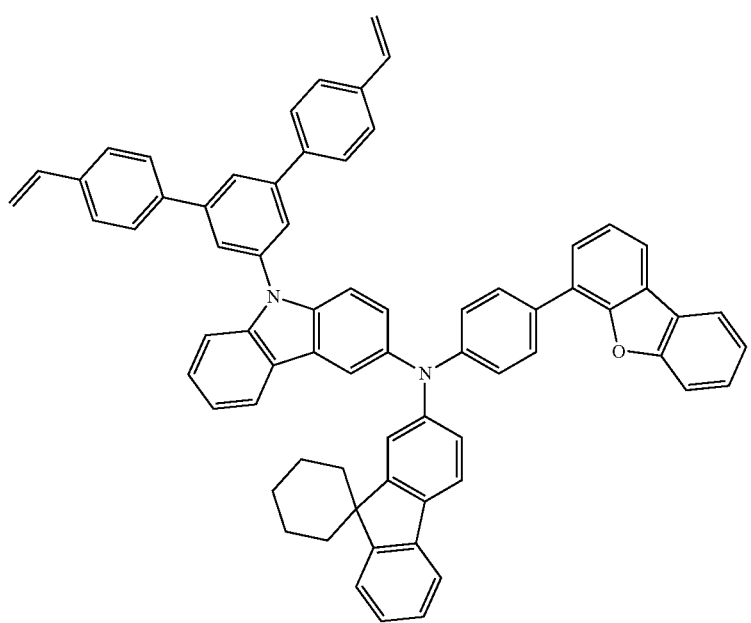 [SMILES: C=Cc1ccc(-c2cc(-c3ccc(C=C)cc3)cc(-n3c4ccccc4c4cc(N(c5ccc(-c6cccc7c6oc6ccccc67)cc5)c5ccc6c(c5)C5(CCCCC5)c5ccccc5-6)ccc43)c2)cc1]

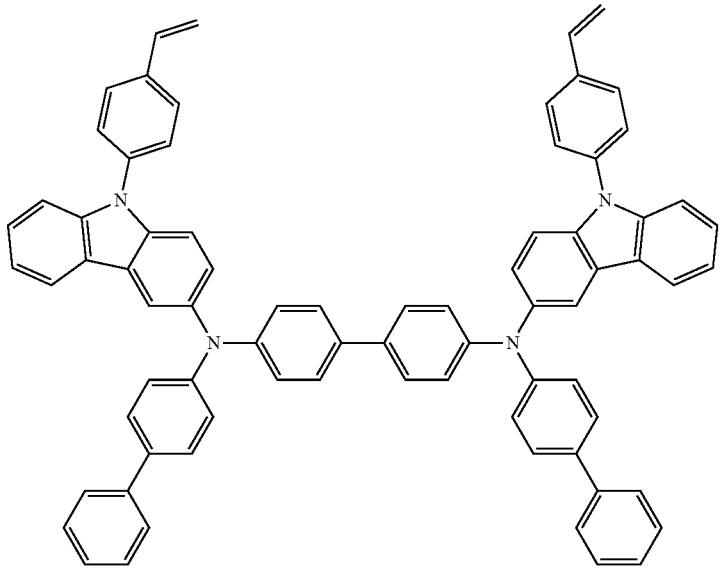 [SMILES: C=Cc1ccc(-n2c3ccccc3c3cc(N(c4ccc(-c5ccccc5)cc4)c4ccc(-c5ccc(N(c6ccc(-c7ccccc7)cc6)c6ccc7c(c6)c6ccccc6n7-c6ccc(C=C)cc6)cc5)cc4)ccc32)cc1]

79

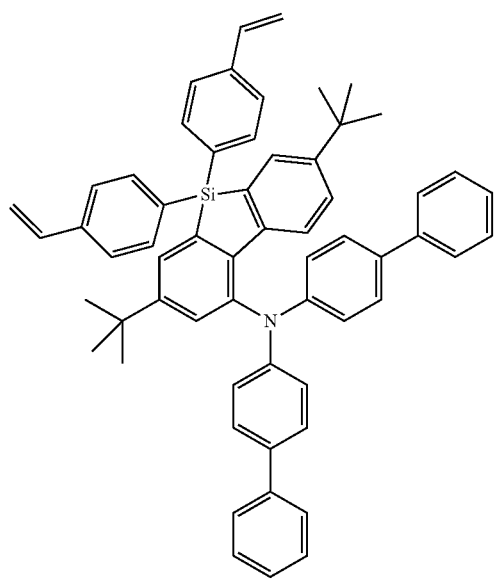 [SMILES: C=Cc1ccc([Si]2(c3ccc(C=C)cc3)c3cc(C(C)(C)C)ccc3-c3c(N(c4ccc(-c5ccccc5)cc4)c4ccc(-c5ccccc5)cc4)cc(C(C)(C)C)cc32)cc1]

80

The present invention furthermore relates to a crosslinked compound which is obtainable by crosslinking the groups Q of the compound of the formula (1). A crosslinked compound in the sense of the present invention is a compound which is obtainable from the compound of the formula (1) by carrying out the reaction of the crosslinkable group Q.

The crosslinkable compound of the formula (1) can be applied by coating from solution to a corresponding support substrate (glass, polymer etc.) or a layer which has already been deposited in advance and crosslinked either before or after removal of the solvent or during removal of the solvent.

The present invention thus also relates to a layer comprising one or more compounds according to the invention as defined above or comprising one or more compounds obtained by crosslinking the compounds according to the invention.

The present invention furthermore relates to a process for the production of a crosslinked layer by application and crosslinking of a compound of the formula (1). The process for the preparation of such a crosslinked layer comprises the following steps:

(a) provision of the compounds of formula (1) which contain one or more crosslinkable groups Q; and (b) crosslinking, which can be induced both thermally and also by radiation, preferably thermally.

The crosslinked layers prepared by the process according to the invention are insoluble in all common solvents. In this way, it is possible to produce defined layer thicknesses which are not dissolved or partially dissolved again, even by the application of subsequent layers.

The compound of the formula (1) here can be crosslinked as pure substance, or it can be applied as a mixture with at least one other compound and crosslinked together with the latter. In a preferred embodiment of the invention, the compound of the formula (1) is crosslinked as pure substance.

The layer comprising the crosslinkable compounds of formula (1) can be produced, for example, by coating from solution, preferably by gravure printing, ink-jet printing, nozzle printing, flexographic printing, dye coating, screen printing or spin coating. After application of a layer of the compound of the formula (1) and optionally removal of the solvent, the compound can be crosslinked. The crosslinking is preferably carried out with radiation induction (for example using UV light, visible light, microwaves, electron beams) or thermally, in particular thermally.

The present invention furthermore relates to a solution or a formulation comprising at least one compound of the formula (1) and one or more solvents. The way in which formulations of this type can be prepared is known to the person skilled in the art and described, for example, in WO 2002/072714, WO 2003/019694 and the literature cited therein.

These solutions can be used in order to produce thin layers, for example by surface-coating methods (for example spin coating) or by printing processes (for example ink-jet printing).

Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphtalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention also encompasses so-called hybrid devices, in which one or more layers which are processed from solution and layers which are produced by vapour deposition of low-molecular-weight substances may occur.

The present invention also relates to the use of the compounds according to the invention and the crosslinked compounds obtained therefrom in an electronic device.

The present invention again furthermore relates to an electronic device comprising one or more compounds of the formula (1) or one or more crosslinked compounds obtained by crosslinking the compound of the formula (1).

The electronic device is preferably an organic electroluminescent device (OLED), an organic integrated circuit (O-IC), an organic field-effect transistor (O-FT), an organic thin-film transistor (O-TFT), an organic, light-emitting transistor (O-LET), an organic solar cell (O-SC), an organic, optical detector, an organic photoreceptor, an organic field-quench device (O-FQD), a light-emitting electrochemical cell (LEC) or an organic laser diode (O-laser), preferably an organic electroluminescent device (OLED).

In the case of the hybrid device mentioned above, the term combined PLED/SMOLED (polymeric light emitting diode/ small molecule organic light emitting diode) systems is used in connection with organic electroluminescent devices.

The way in which OLEDs can be produced is known to the person skilled in the art and is described in detail, for example, as a general process in WO 2004/070772 A2, which should be adapted correspondingly for the individual case.

In a further embodiment of the present invention, the device comprises a plurality of layers. The compound of the formula (1) according to the invention or the crosslinked compound obtained therefrom may be present here in a hole-transport, hole-injection, emitter, electron-transport, electron-injection, charge-blocking and/or charge-generation layer.

The organic electroluminescent device according to the invention comprises cathode, anode and at least one emitting layer. Apart from these layers, the organic electroluminescent device may also comprise further layers, for example in each case one or more hole-injection layers, hole-transport layers, hole-blocking layers, electron-transport layers, electron-injection layers, exciton-blocking layers and/or charge-generation layers. Interlayers, which have, for example, an exciton-blocking function, may likewise be introduced between two emitting layers. However, it should be pointed out that each of these layers does not necessarily have to be present. It is also possible for a plurality of OLEDs to be arranged one above the other, enabling a further increase in efficiency to be achieved with respect to the light yield. In order to improve the coupling-out of light, the final organic layer on the light exit side in OLEDs may also be, for example, in the form of a nanofoam or another material having a low refractive index, resulting in a reduction in the proportion of total reflection.

It is also possible for the organic electroluminescent device according to the invention to comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers.

The device may comprise layers which are built up from low-molecular-weight compounds. These can be produced by vapour deposition of the compounds in a high vacuum or by application from solution. The device may likewise comprise layers which are built up from oligomeric, polymeric or dendritic compounds. These are produced, in particular, by application from solution.

The organic electroluminescent device according to the invention preferably has the following structure: anode/ optionally layer comprising a conductive polymer/one or more crosslinked layers, obtainable by crosslinking the compound of the formula (1)/emission layer and cathode.

In a preferred embodiment of the present invention, the compounds according to the invention and the crosslinked compounds obtained therefrom are used in a hole-transport layer or in a hole-injection layer. This layer is used as interlayer between the anode or the conductive polymer and the emitting layer. A hole-injection layer in the sense of the present invention denotes a layer which is directly adjacent to the anode. A hole-transport layer in the sense of the present invention denotes a layer which is arranged between a hole-injection layer and an emitting layer.

The crosslinked hole-transport layer or the crosslinked hole-injection layer may also additionally comprises one or more p-dopants as described, for example in WO 2013/ 081052 A1, WO 2013/047581 A1, EP 1725079 A1, EP 2469804 A2 and WO 2013/182389 A2.

Particularly preferred embodiments of p-dopants are known from the prior art and/or are commercially available as summarized in the following table:

| Dopant | Structure | CAS or litterature |
|---|---|---|
| D1 | 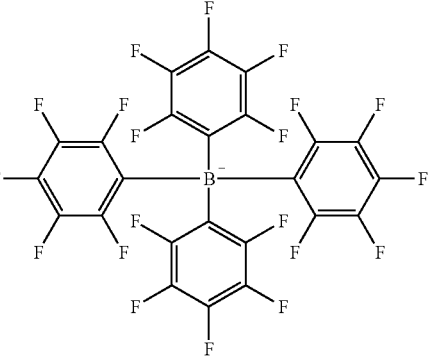 | 178233-72-2 |
| D2 | 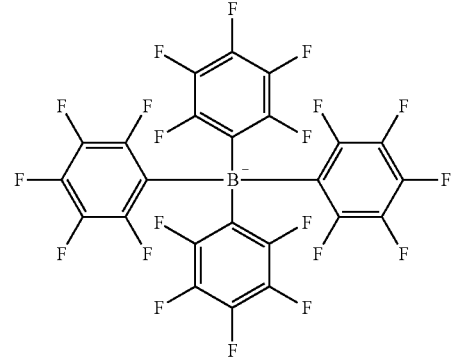 | 136040-19-2 |
| D3 | 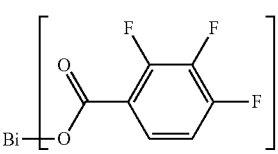 | WO 2013/182389 |

In particular for lighting applications, it is preferred for a p-doped layer of the compound of the formula (1) to be applied directly to the anode and crosslinked there. An additional layer comprising a conductive polymer is not necessary here, i.e. the crosslinked layer obtained by crosslinking the compound of the formula (1) serves as replacement for the doped conductive polymer. The layer thickness of this layer is preferably between 10 and 400 nm, particularly preferably between 20 and 200 nm.

The compounds of the formula (1) according to the invention and the crosslinked compounds according to the invention obtained therefrom are furthermore preferably used in a hole-transport layer, where this hole-transport layer is applied to a layer of a conductive polymer. Suitable as conductive polymer are all materials as usually used for this layer by the person skilled in the art, for example PEDOT/PSS, doped PANI or doped oligoanilines. The layer thickness of the hole-transport layer according to the invention is usually in the range from 10 to 400 nm, preferably in the range from 20 to 200 nm.

All materials as are usually used in organic electroluminescent devices and as are known to the person skilled in the art can be used in the further layers.

If the emitting layer used is a phosphorescent layer, this preferably consists of low-molecular-weight compounds which are applied from solution.

If the emitting layer used is a blue fluorescent layer, this preferably consists of low-molecular-weight compounds which are either applied from solution or applied by vacuum vapour deposition.

In particular in the above-mentioned cases of phosphorescent or blue-fluorescent emitter layers, but also in other electroluminescent devices, it is preferred for the organic electroluminescent device to comprise an electron-transport layer. This is preferably applied to the emitting layer by vapour deposition. Suitable materials for the electron-transport layer are benzimidazole derivatives, triazine derivatives and/or hydroxyquinoline complexes, such as, for example, LiQ (lithium quinolinate).

Preference is given to an organic electroluminescent device which is characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or inkjet printing. The compound of the formula (1) is particularly preferably applied from solution.

Preference is furthermore given to an organic electroluminescent device in which one or more layers are coated by means of a sublimation process, in which the materials are applied by vapour deposition in vacuum sublimation units at a pressure less than $10^{-5}$ mbar, preferably less than $10^{-6}$ mbar, particularly preferably less than $10^{-7}$ mbar.

Preference is likewise given to an organic electroluminescent device which is characterised in that one or more layers are coated by means of the OVPD (organic vapour phase deposition) process or with the aid of carrier-gas sublimation, in which the materials are applied at a pressure between $10^{-5}$ mbar and 1 bar.

It is also possible to produce the organic electroluminescent device as hybrid device by, for example, applying one or more layers from solution and applying one or more further layers by vacuum vapour deposition. Thus, for example, the layer comprising the compound of the formula (1) can be applied from solution and the emitting layer can be applied by vapour deposition. It is likewise possible to apply the layer comprising the compound of the formula (1) and the emitting layer from solution and to apply the electron-transport layer by vapour deposition.

As layer directly on the anode, use is preferably made of conductive doped polymers, such as, for example, in each case doped poly(ethylenedioxythiophene) (PEDOT), polyaniline (PANI) or oligoaniline, if a layer according to the invention is not used for this purpose.

The device is correspondingly structured, depending on the application, provided with contacts and finally hermetically sealed, since the lifetime of such devices is drastically shortened in the presence of water and/or air.

The present application text and also the examples below are principally directed to the use of the compounds of formula (1) according to the invention in relation to OLEDs and corresponding displays. In spite of this restriction of the description, it is possible for the person skilled in the art, without further inventive step, also to use the compounds according to the invention as semiconductors for the further uses described above in other electronic devices.

The following examples are intended to explain the invention without restricting it. In particular, the features, properties and advantages described therein of the defined compounds on which the relevant example is based can also be applied to other compounds which are not described in detail, but fall within the scope of protection of the claims, unless stated otherwise elsewhere.

SYNTHESIS EXAMPLES

Synthesis Example 1

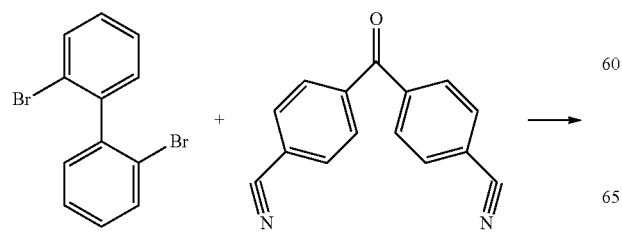

-continued

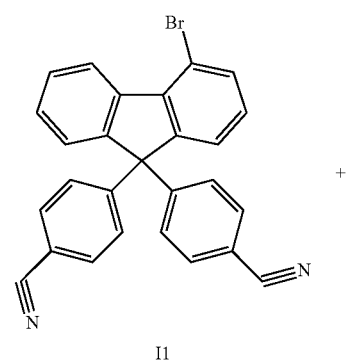

I1

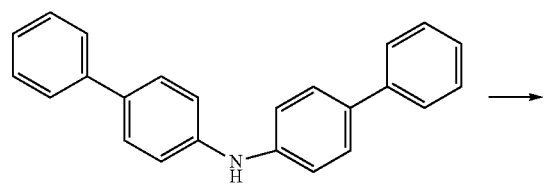

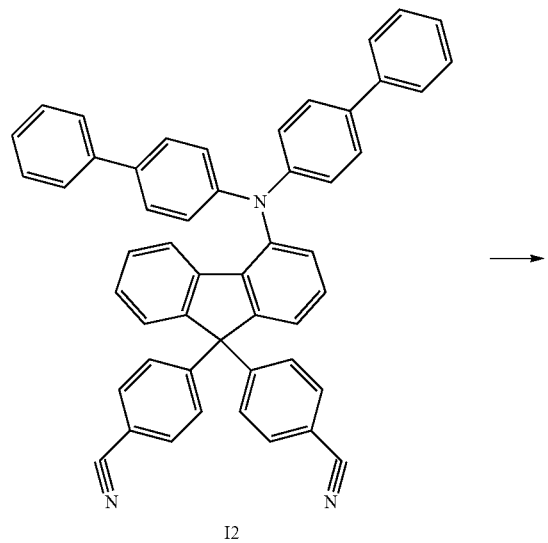

I2

-continued

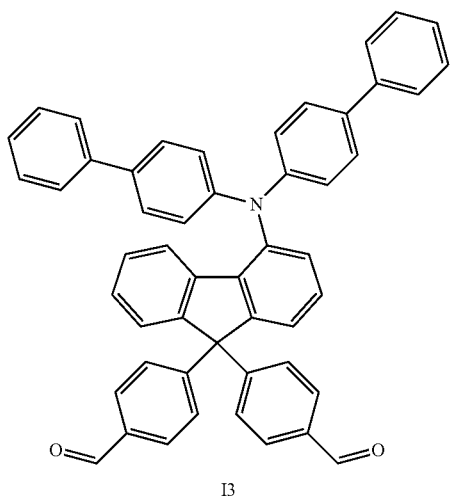

I3

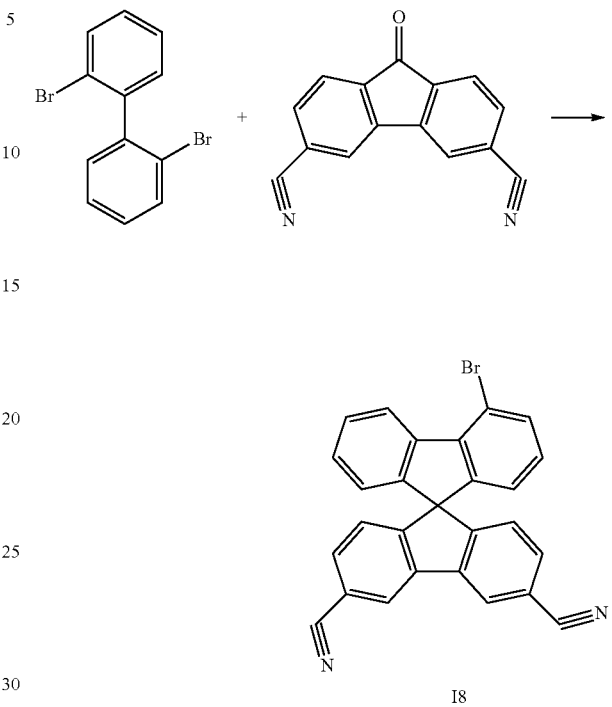

I8 was made analogous to I1 with a yield of 73% (CAS: 85313-23-1):

P1

123.4 g (388 mmol) 2,2'-Dibromo-biphenyl were dissolved in 450 ml dry THF and cooled to −78° C. 135 ml (323 mmol, 2.5 M in Hexane) n-BuLi was added slowly and the mixture was stirred for 45 min. 4,4'-Dicyanobenzophenone (CAS: 32446-66-5) was dissolved in 400 ml dry THF and cooled to −78° C. The mixture of n-Buli and 2,2'-Dibromobiphenyl was then transferred to the 4,4'-Dicyanobenzophenone solution. The reaction was warmed to room temperature over night and after that quenched with water. THF was evaporated in vacuo and the residue was extracted with ethyl acetate and water. The organic phase was dried, filtered and the solvent was removed in vacuo which resulted in 170 g of crude solid. The crude solid was refluxed over night with 2700 ml acetic acid and 200 ml (37%) hydrochloric acid. After cooling to RT the reaction mixture was poured in water and the resulting solid was filtered off, dissolved in dichloromethane, the solution was washed with water and NaHCO3, the organic phase was dried and the solvent removed in vacuo. The resulting solid was recrystallized in ethyl acetate and finally purified via flash chromatography. The resulting white solid I1 was obtained with a yield of 61% (88 g, 197 mmol).

25 g (56 mmol) I1 and 19.8 g (62 mmol, 1.1 eq) Bis-biphenyl-4-y-amine were added to 450 ml Toluene. Subsequently 10.2 g (11.2 mmol, 0.2 eq) $Pd_2dba_3$ and 10.7 g (112 mmol, 2 eq) Sodium-t-butylate were added and the mixture was degassed with argon. After 5 min degassing 25 g (11.2 mmol, 0.2 eq) tri-t-butylphosphine was added and the reaction was stirred at reflux over the weekend. After cooling to RT the mixture was filtered over Celite and subsequently purified via Soxhlet using Toluene as the solvent. The resulting solid was purified via flash chromatography. 14.6 g (21 mmol, 38%) of I2 was obtained.

22 g (31.3 mmol) I2 was dissolved in 170 ml Toluene and cooled to −78° C. At −78° C. DIBAL-H (250 ml, 1M in Hexane) was added slowly. The mixture was stirred for 30 min at −78° C. and the warmed to RT over night. The reaction was then quenched with MeOH and $H_2SO_4$. The mixture was extracted with ethyl acetate and washed with water. The resulting solid was purified with flash chromatography. 3.5 g (5 mmol, 16%) of intermediate I3 were obtained.

3.2 g (4.6 mmol) I3 was dissolved in 125 ml of dry THF. 18.1 g (50.6 mmol) of Methyltriphenylphosphoniumbromied was dissolved in 225 ml dry THF and cooled to −3° C. Then 5.6 g (59 mmol) Sodium-t-butylate was added at −3° C., the suspension was stirred for 60 min at −3° C. Then the solution of I3 in THF was added dropwise, the reaction mixture was stirred for 2 h at 0° C. and the warmed to RT over night. The solution was diluted with Toluene and quenched with water. The organic phase was separated and the aqueous phase was extracted with Toluene. The organic phases were dried and the solvent was evaporated in vacuo. The resulting solid was recrystallized from Toluene/MeOH. 1.9 g (2.7 mmol, 60%) of P1 was obtained as a white solid.

| Amine | Starting Material | Product | Yield |
|---|---|---|---|
| P2 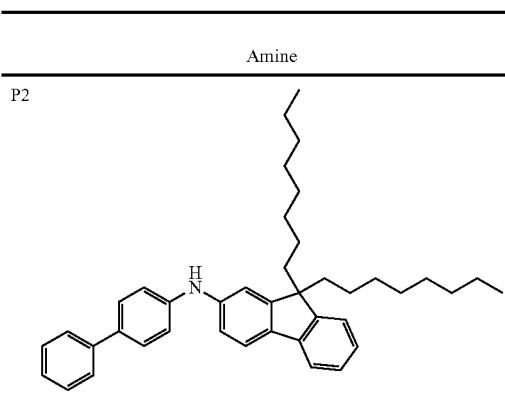 | I1 | 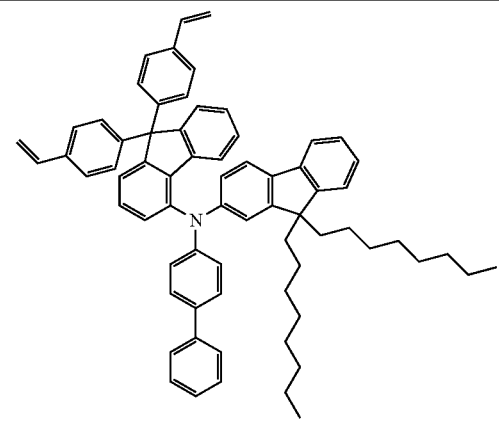 | 11% |
| P3 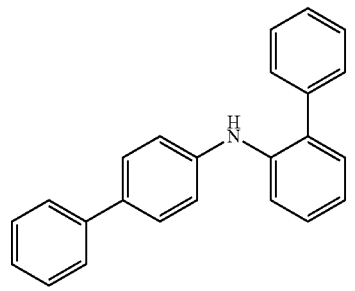 | I1 | 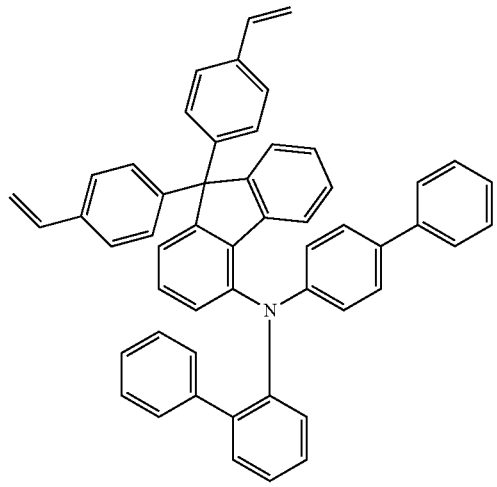 [SMILES: C=Cc1ccc(C2(c3ccc(C=C)cc3)c3ccccc3-c3c(N(c4ccc(-c5ccccc5)cc4)c4ccccc4-c4ccccc4)cccc32)cc1] | 18% |
| P4 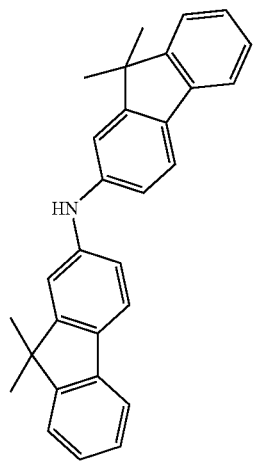 | I1 | 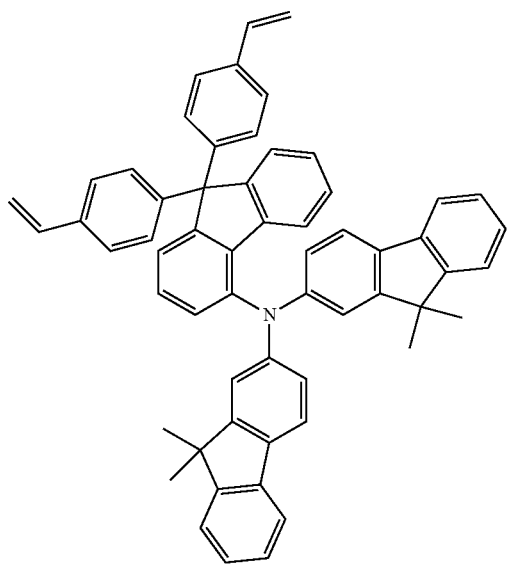 [SMILES: C=Cc1ccc(C2(c3ccc(C=C)cc3)c3ccccc3-c3c(N(c4ccc5c(c4)C(C)(C)c4ccccc4-5)c4ccc5c(c4)C(C)(C)c4ccccc4-5)cccc32)cc1] | 27% |

-continued
| Amine | Starting Material | Product | Yield |
|---|---|---|---|
| P9 | I8 | | 8% |
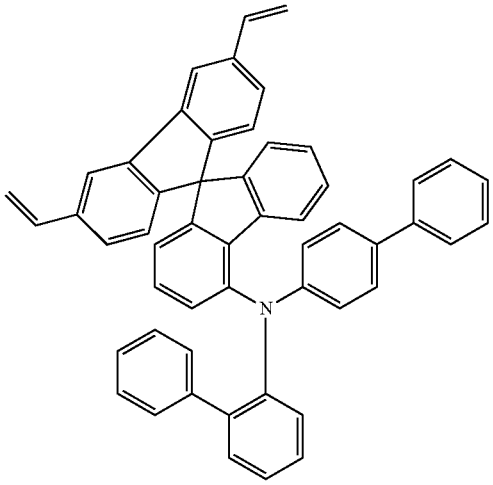 [SMILES: C=Cc1ccc2c(c1)-c1cc(C=C)ccc1C21c2ccccc2-c2c(N(c3ccc(-c4ccccc4)cc3)c3ccccc3-c3ccccc3)cccc21]
Synthesis Example 2
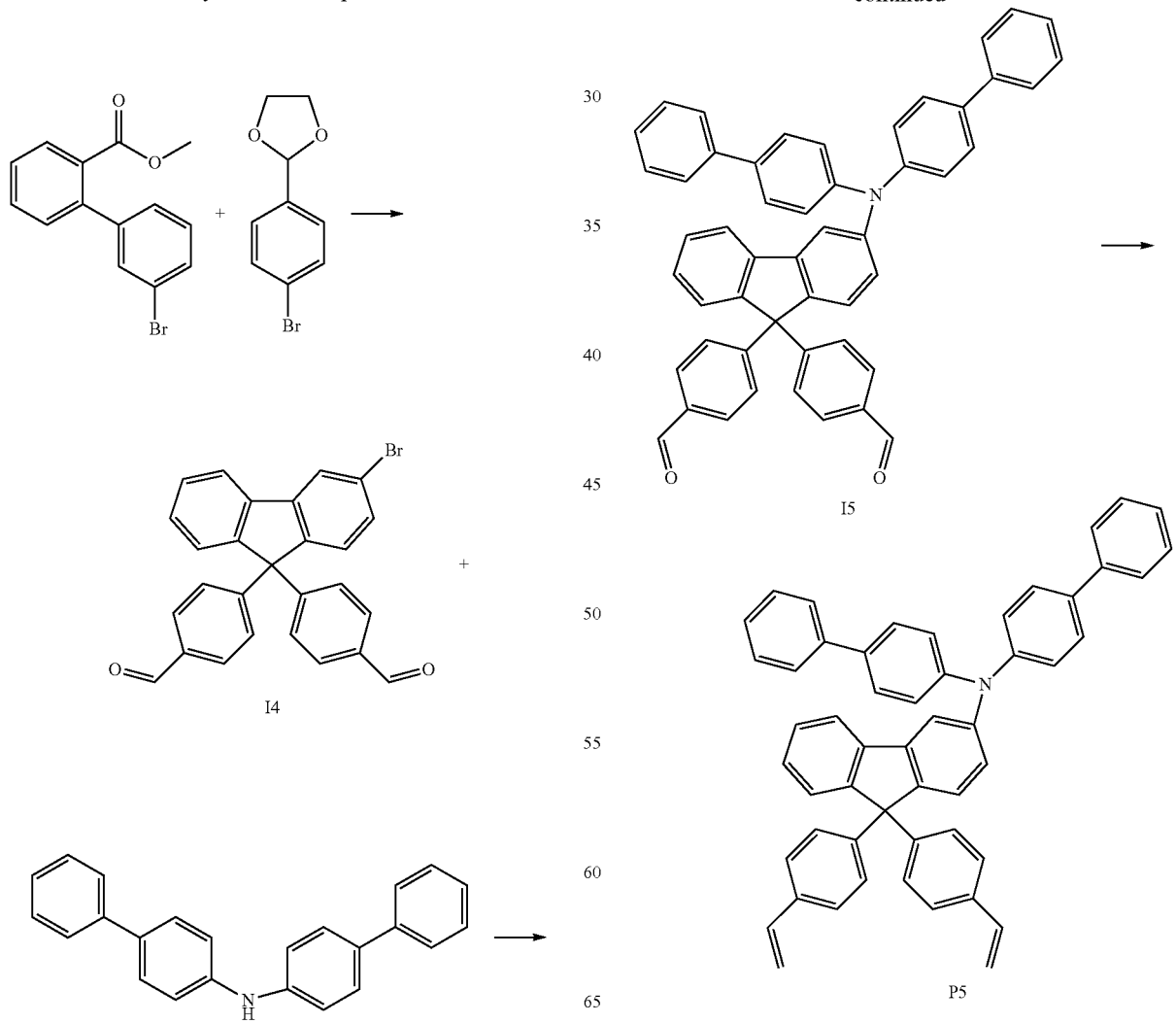

18 g (77 mmol) 2-(4-Bromophenyl)-1,3-dioxolane was dissolved in 150 ml dry THF and cooled to −78° C. 31 ml (77 mmol, 2.5 M solution) of n-BuLi was added dropwise and the solution was stirred for one hour at −78° C. 3′-Bromo-biphenyl-2-carboxylic acid (30.8 mmol, 9 g) was dissolved in 25 ml THF and added to the n-BuLi solution at −78° C. The reaction mixture was stirred for 1 h at −78° C. and then warmed to RT over the weekend. Ammoniumchloride solution was added to quench the reaction and the mixture was extracted with ethyl acetate. The combined organic phases were dried and the solvent was evaporated in vacuo. The resulting crude product was dissolved in 60 ml dry Toluene and 60 ml Hydrochloric acid (37%) as well as 115 ml acetic acid was added. The reaction was stirred at 80° C. over night. After cooling down to RT the water was added, the aqueous phase was extracted with toluene and the combined organic phases were washed with water and dried with Na$_2$SO$_4$. The solvent was removed in vacuo. The resulting solid was recrystallized in Heptane/Toluene. I4 was obtained as a white product with 76% yield (22.8 mmol, 10.3 g).

To obtain I5 and P5 the subsequent steps were performed analogous to Intermediates I2 and product P1.

| Name | Amine | Starting Material | Product | Yield |
|------|-------|-------------------|---------|-------|
| P6 |  | I4 |  | 5% |
| P7 |  |  |  | 16% |

Synthesis Example 3

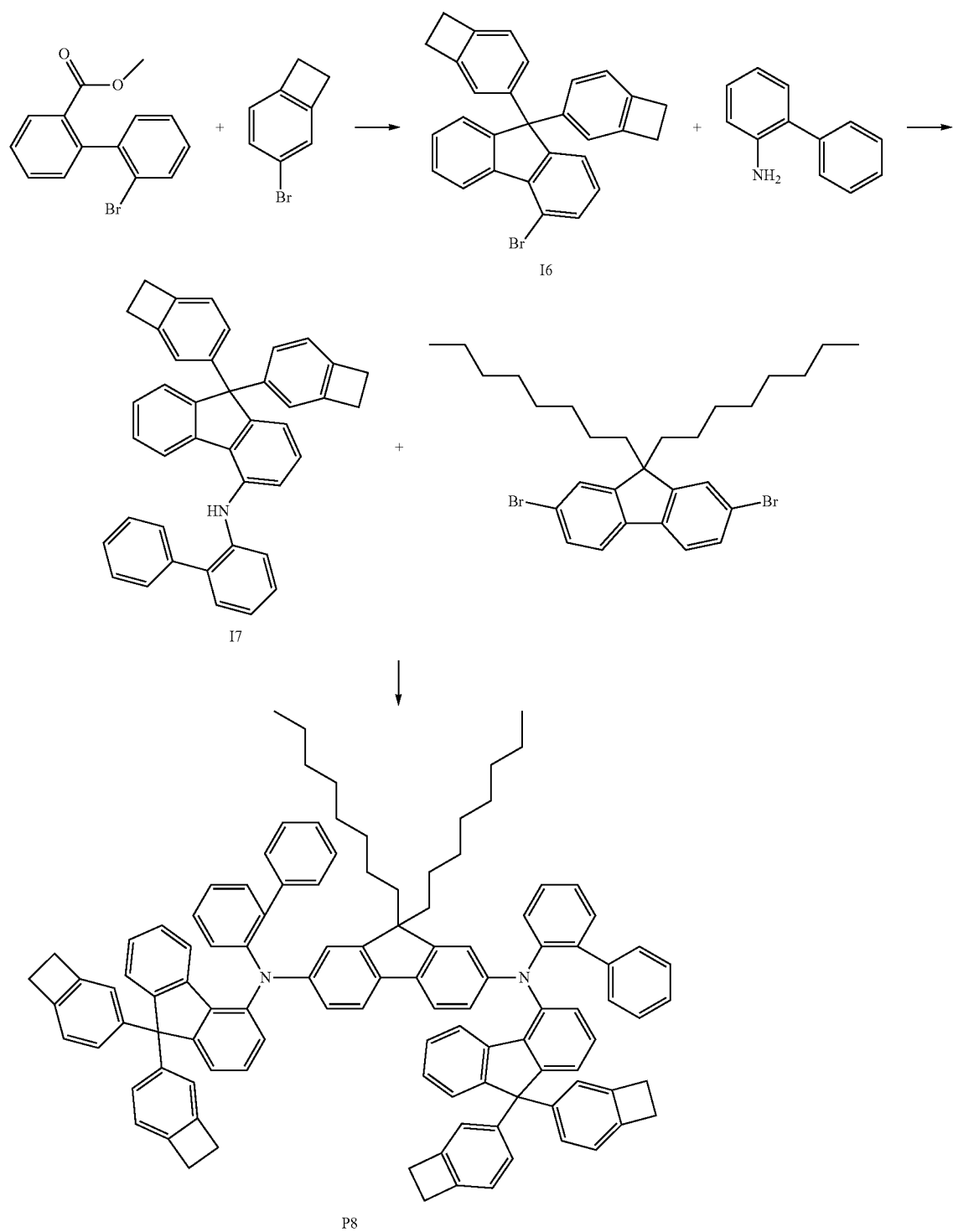

20 g (109 mmol) 2-(4-Bromophenyl)-cyclobutyl was dissolved in 150 ml dry THF and cooled to −78° C. 44 ml (109 mmol, 2.5 M solution) of n-BuLi was added dropwise and the solution was stirred for one hour at −78° C. 2′-Bromobiphenyl-2-carboxylic acid (43.6 mmol, 12.7 g) was dissolved in 25 ml THF and added to the n-BuLi solution at −78° C. The reaction mixture was stirred for 1 h at −78° C. and then warmed to RT over the weekend. Ammoniumchloride solution was added to quench the reaction and the mixture was extracted with ethyl acetate. The combined organic phases were dried and the solvent was evaporated in vacuo. The resulting crude product was dissolved in 60 ml dry Toluene and 60 ml Hydrochloric acid (37%) as well as 115 ml acetic acid was added. The reaction was stirred at 80° C. over night. After cooling down to RT the water was added, the aqueous phase was extracted with toluene and the combined organic phases were washed with water and dried with $Na_2SO_4$. The solvent was removed in vacuo. The resulting solid was recrystallized in Heptane/Toluene. I6 was obtained as a white product with 85% yield (37.1 mmol, 16.6 g).

I6 (15 g, 33.4 mmol), o-biphenylamine (6.2 g, 36.7 mmol) and Sodium-t-butylate (10.6 g, 110 mmol) were dissolved in 200 ml toluene. The mixture was degassed for 15 minutes and subsequently Pd(dppf)Cl2 (1.8 g, 2.2 mmol) was added. The solution was heated at reflux for 4 hours and then cooled to RT. The mixture was filtered over Alox using toluene as the solvent. The resulting solid was recrystallized from toluene/heptanes. I7 was obtained as a white solid with a yield of 63% (11.3 g, 21 mmol).

4.7 g (8.5 mmol) 2,7-dibromo-9,9-dioctyl-fluorene and 10 g (18.6 mmol, 2.2 eq) I7 were added to 100 ml Toluene. Subsequently 1.5 g (1.7 mmol, 0.2 eq) $Pd_2dba_3$ and 1.6 g (17 mmol, 2 eq) Sodium-t-butylate were added and the mixture was degassed with argon. After 5 min degassing 3.8 g (1.7 mmol, 0.2 eq) tri-t-butylphosphine was added and the reaction was stirred at reflux over the weekend. After cooling to RT the mixture was filtered over Celite and subsequently purified via Soxhlet using Toluene as the solvent. The resulting solid was purified via flash chromatography. 9.7 g (6.6 mmol, 78%) of P8 was obtained.

| | Amine | Starting Material | Product | Yield |
|---|---|---|---|---|
| P10 | | | | 32% |

*The Wittig Reaction was performed analogous to the synthesis of P1.

Comparative Example V1: Synthesis is Described in WO2013007348

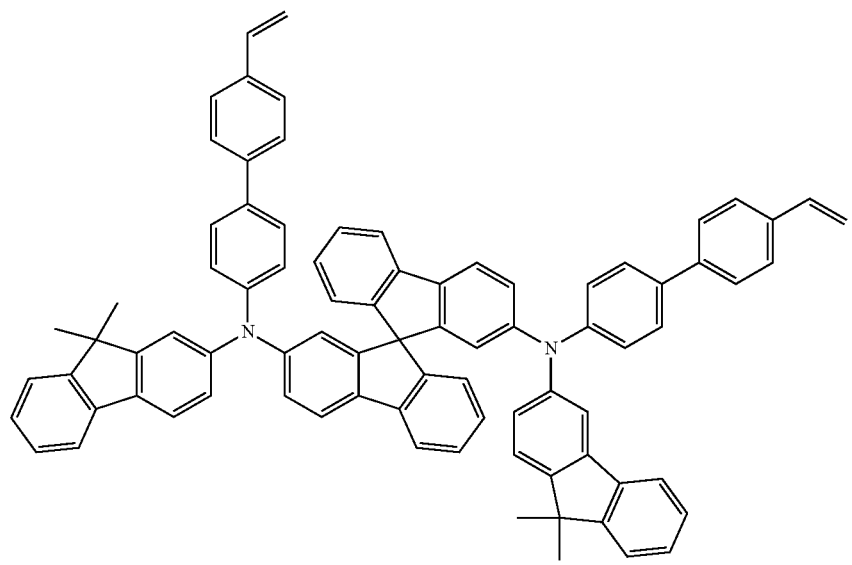

V1

Device Examples

The cross-linkable small molecules according to the invention can be processed from solution and result in OLEDs which are significantly easier to produce than vacuum-processed OLEDs, but nevertheless have good properties.

Whether the cross-linkable small molecules according to the invention give a completely insoluble layer after cross-linking is tested analogously to WO 2010/097155.

Table C1 shows the remaining layer thickness of the originally 20 nm after the washing operation described in WO 2010/097155. If the layer thickness does not reduce, the formed film is insoluble and the cross-linking is thus adequate.

TABLE C1

Check of the residual layer thickness from originally 20 nm after washing test

| Polymer | Residual layer thickness after washing test [in nm] Crosslinking at 220° C. |
|---|---|
| V1 | 19.2 |
| P1 | 18.9 |
| P10 | 20 |

As can be seen in Table C1, all three molecules V1, P1 and P10 show acceptable cross-linking at 220° C. Due to its 4 cross-linking groups, the layer out of cross-linked P10 is completely insoluble.

The production of solution-based OLEDs of this type has already been described many times in the literature, for example in WO 2004/037887 and WO 2010/097155. The process is adapted to the circumstances described below (layer-thickness variation, materials).

The molecules according to the invention are used in the following layer sequence:
substrate,
ITO (50 nm),
PEDOT (80 nm),
hole-transport layer (HTL) (20 nm),
emission layer (EML) (60 nm),
hole-blocking layer (HBL) (10 nm)
electron-transport layer (ETL) (40 nm),
cathode.

Glass plates coated with structured ITO (indium tin oxide) in a thickness of 50 nm serve as substrate. These are coated with PEDOT:PSS for better processing. The spin coating is carried out from water in air. The layer is dried by heating at 180° C. for 10 minutes. PEDOT:PSS is purchased from Heraeus Precious Metals GmbH & Co. KG, Germany. The hole-transport and emission layers are applied to these coated glass plates.

The compounds according to the invention and comparative compounds, in each case dissolved in toluene, are used as hole-transport layer. The typical solids content of such solutions is about 7 g/l if the layer thickness of 20 nm is to be achieved by means of spin coating. The layers are applied by spin coating in an inert-gas atmosphere, in the present case argon, and dried by heating at 220° C. for 60 minutes.

The emission layer is always composed of at least one matrix material (host material) and an emitting dopant (emitter). Furthermore, mixtures of a plurality of matrix materials and co-dopants may occur. An expression such as H1 (92%):dopant (8%) here means that material H1 is present in the emission layer in a proportion by weight of 92% and the dopant is present in the emission layer in a proportion by weight of 8%. The mixture for the emission layer is dissolved in toluene. The typical solids content of such solutions is about 18 g/l if, as here, the layer thickness of 60 nm which is typical for a device is to be achieved by means of spin coating. The layers are applied by spin coating in an inert-gas atmosphere, in the present case argon, and dried by heating at 160° C. for 10 minutes.

The materials used in the present case are shown in Table C2.

TABLE C2

Structural formulae of the materials used in the emission layer

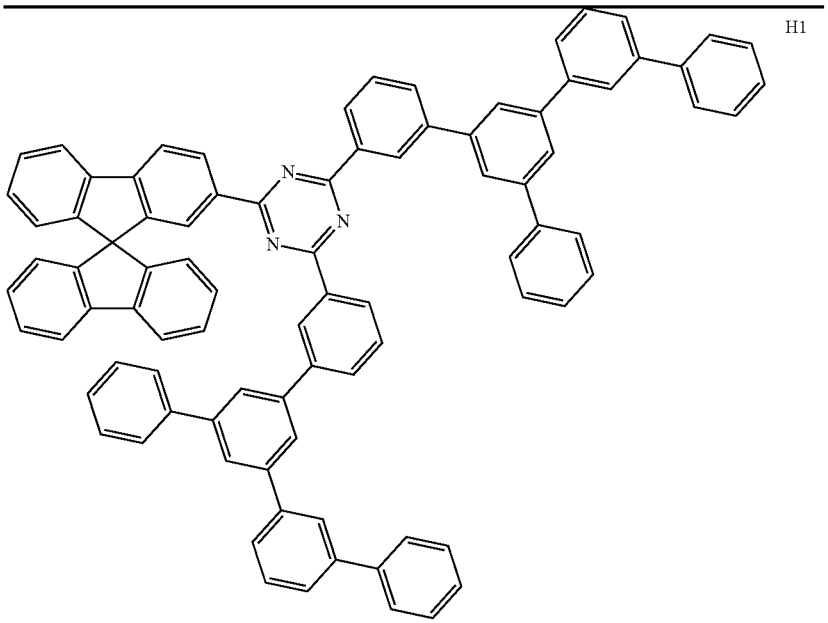

TABLE C2-continued

Structural formulae of the materials used in the emission layer

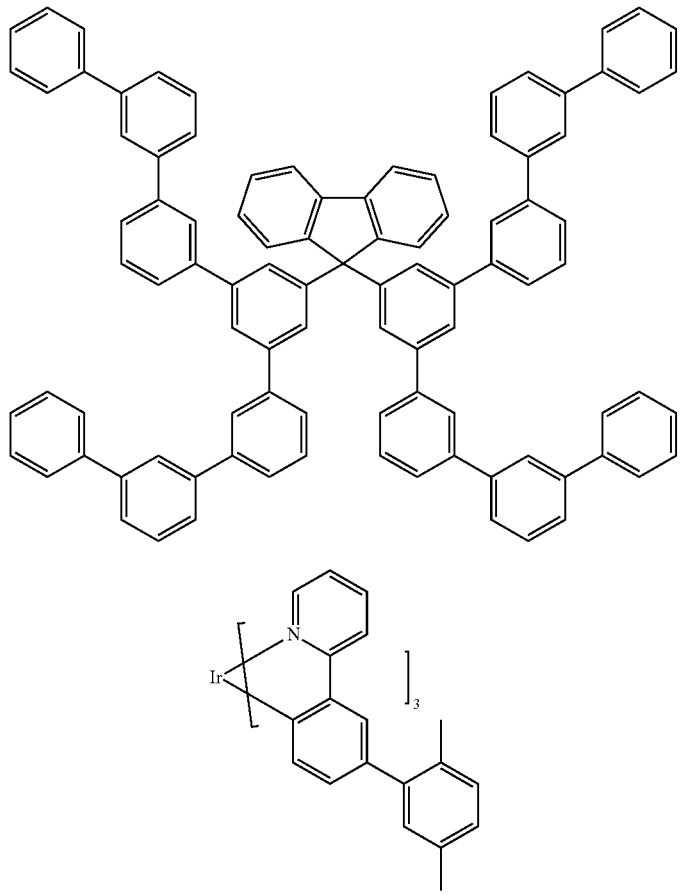
H2

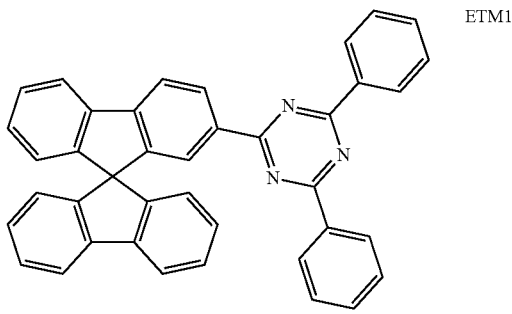
TEG

The materials for the hole-blocking layer and electron-transport layer are applied by thermal vapour deposition in a vacuum chamber and are shown in Table C3. The hole-blocking layer consists of ETM1. The electron-transport layer consists of the two materials ETM1 and ETM2, which are mixed with one another in a proportion by volume of 50% each by coevaporation.

TABLE C3

HBL and ETL materials used

ETM1

TABLE C3-continued

HBL and ETL materials used

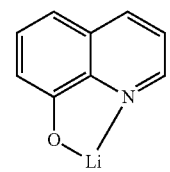
ETM2

The cathode is formed by the thermal evaporation of an aluminum layer with a thickness of 100 nm.

The precise structure of the OLEDs is shown in Table C4. Column HTL shows the molecule used and the temperature at which the layer is dried by heating and crosslinked.

TABLE C4

Structure of the OLEDs

| Example | HTL Molecule | T [° C.] | EML Composition |
|---------|--------------|----------|-----------------|
| C01 | V1 | 220° C. | H1 30%; H2 55%; TEG 15% |
| C02 | P1 | 220° C. | H1 30%; H2 55%; TEG 15% |
| C03 | P10 | 220° C. | H1 30%; H2 55%; TEG 15% |

The OLEDs are characterised by standard methods. For this purpose, the electroluminescence spectra, current/voltage/luminous density characteristic lines (IUL characteristic lines) assuming Lambert emission characteristics and the (operating) lifetime are determined. The IUL characteristic lines are used to determine characteristic numbers such as the operating voltage (in V) and the external quantum efficiency (in %) at a certain luminance. LT80 @ 10000 cd/m² is the lifetime by which the OLED has dropped from an initial luminance of 10000 cd/m² to 80% of the initial intensity, i.e. to 8000 cd/m².

The properties of the various OLEDs are summarised in Table C5. Example C01 is a comparative examples, both other examples show properties of OLEDs according to the invention.

TABLE C5

Properties of the OLEDs

| Example | Efficiency at 1000 cd/m² % EQE | Voltage at 1000 cd/m² [V] | LT80 at 10000 cd/m² [h] |
|---|---|---|---|
| C01 | 17.0 | 4.8 | 110 |
| C02 | 16.6 | 5.1 | 140 |
| C03 | 17.0 | 4.9 | 190 |

As Table C5 shows, the polymers according to the invention give rise to improvements over the prior art, in particular with respect to lifetime, on use as hole-transport layer in OLEDs. Green emitting OLEDs comprising the materials according to the invention are produced.

Example C03 shows better lifetime than example C01: although the molecule P10 has four cross-linking groups, the lifetime is better than in example C01, where molecule V1 has only two cross-linking groups. Molecule P10 is according to the invention and improves lifetime significantly.

The invention claimed is:
1. A crosslinked compound obtained by crosslinking groups Q of a compound of the formula (2) or (3),

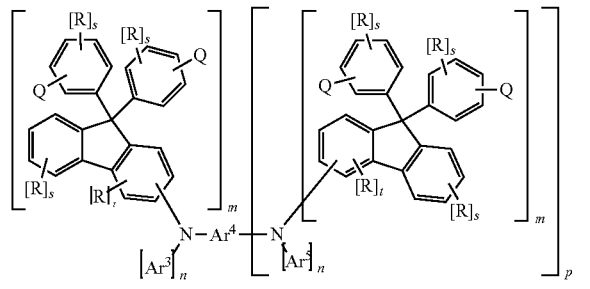

formula (2)

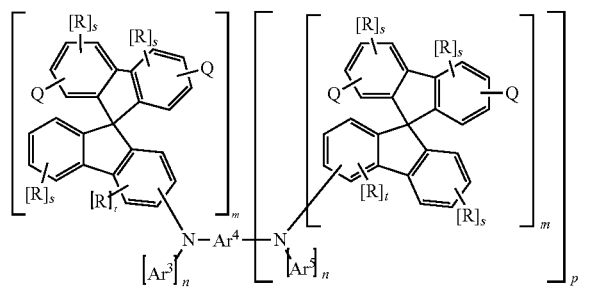

formula (3)

where
Ar³, Ar⁴, Ar⁵ are selected on each occurrence, identically or differently, from the group consisting of an aromatic or heteroaromatic ring system having 5 to 60 aromatic ring atoms, which may be substituted by one or more radicals R;

Q is on each occurrence, identically or differently, a crosslinkable group bonded to the adjacent phenyl group via a single bond, or Q is a crosslinkable mono- or polycyclic group condensed on the adjacent phenyl group;

R is on each occurrence, identically or differently, H, D, F, Cl, Br, I, CHO, N(Ar)$_2$, C(=O)Ar, P(=O)(Ar)$_2$, S(=O)Ar, S(=O)$_2$Ar, (R)C=C(R)Ar, CN, NO$_2$, Si(R$^1$)3, B(OR$^1$)$_2$, B(R$^1$)$_2$, B(N(R$^1$)$_2$)$_2$, OSO$_2$R$^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^1$, where one or more, non-adjacent CH$_2$ groups may be replaced by (R$^1$)C=C(R$^1$), C≡C, Si(R$^1$)$_2$, Ge(R$^1$)$_2$, Sn(R$^1$)$_2$, C=O, C=S, C=Se, P(=O)(R$^1$), SO, SO$_2$, N(R$^1$), O, S or CON(R$^1$) and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^1$, or an aryloxy or heteroaryloxy group having 5 to 60 aromatic ring atoms, which may be substituted by one or more radicals R$^1$, where optionally two adjacent substituents R can form a mono- or polycyclic, aliphatic, aromatic or heteroaromatic ring system with one another;

Ar is an aromatic or heteroaromatic ring system having 5 to 60 aromatic ring atoms, which may be substituted by one or more radicals R$^1$;

R$^1$ is on each occurrence, identically or differently, H, D, F, Cl, Br, I, CHO, N(R$^2$)$_2$, C(=O)R$^2$, P(=O)(R$^2$)$_2$, S(=O)R$^2$, S(=O)$_2$R$^2$, (R$^2$)C=C(R$^2$)$_2$, CN, NO$_2$, Si(R$^2$)$_3$, B(OR$^2$)$_2$, B(R$^2$)$_2$, B(N(R$^2$)$_2$)$_2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more, non-adjacent CH$_2$ groups may be replaced by (R$^2$)C=C(R$^2$), C≡C, Si(R$^2$)$_2$, Ge(R$^2$)$_2$, Sn(R$^2$)$_2$, C=O, C=S, C=Se, P(=O)(R$^2$), SO, SO$_2$, N(R$^2$), O, S or CON(R$^2$) and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, where optionally two adjacent substituents R$^1$ can form a mono- or polycyclic, aliphatic, aromatic or heteroaromatic ring system with one another;

R$^2$ is on each occurrence, identically or differently, H, D, F, Cl, Br, I, CHO, CN, NO$_2$, a straight-chain alkyl, alkoxy or thioalkoxy group having 1 to 20 C atoms or a straightchain alkenyl or alkynyl group having 2 to 20 C atoms or a branched or cyclic alkyl, alkenyl, alkynyl, alkoxy or thioalkoxy group having 3 to 20 C atoms, or an aromatic or heteroaromatic ring system having 5 to 30 aromatic ring atoms or an aryloxy or heteroaryloxy group having 5 to 30 aromatic ring atoms; where optionally two adjacent substituents $R^2$ can form a mono- or polycyclic, aliphatic, aromatic or heteroaromatic ring system with one another;

m is on each occurrence, identically or differently, 1 or 2;

n is on each occurrence, identically or differently, 0 or 1;

with the proviso that m+n=2 in the amino moiety comprising a group $Ar^3$ and an aromatic or heteroaromatic ring system containing Y, and m+n=2 in the amino moiety comprising a group $Ar^5$ and an aromatic or heteroaromatic ring system containing Y;

p is 1;

s is on each occurrence, identically or differently, 0, 1, 2, 3 or 4; and t is on each occurrence, identically or differently, 0, 1, 2 or 3.

2. The compound according to claim 1, with the proviso that s≤3 and t≤2 when the corresponding phenyl ring is substituted by a group Q which corresponds to a mono- or polycyclic group condensed on this phenyl ring.

3. The compound according to claim 1, characterized in that Q is on each occurrence, identically or differently, a crosslinkable group selected from terminal or cyclic alkenyl groups, terminal dienyl groups, terminal alkynyl groups, alkenyloxy groups, dienyloxy groups, alkynyloxy groups, acrylic acid derivatives, oxetane groups, oxirane groups, silanes groups and cyclobutane groups.

4. The compound according to claim 1, characterized in that Q is selected from groups of the following formulae Q1 to Q24,

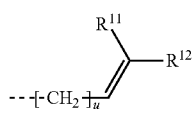

Q1

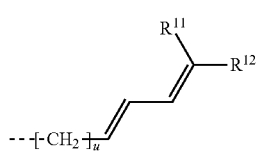

Q2

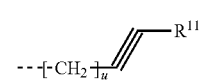

Q3

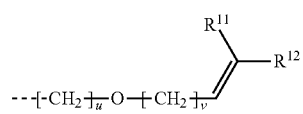

Q4

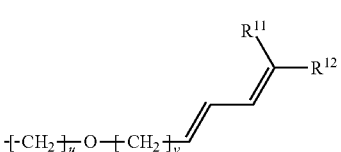

Q5

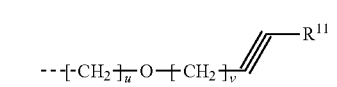

Q6

-continued

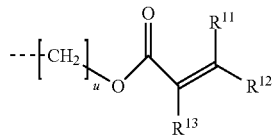

Q7

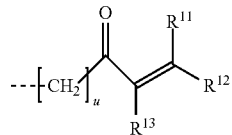

Q8

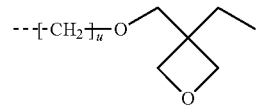

Q9

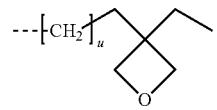

Q10

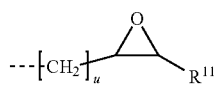

Q11

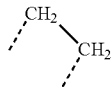

Q12

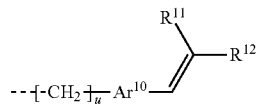

Q13

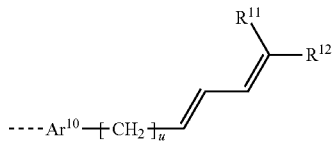

Q14

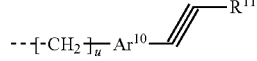

Q15

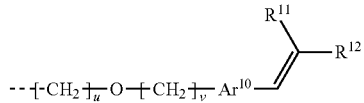

Q16

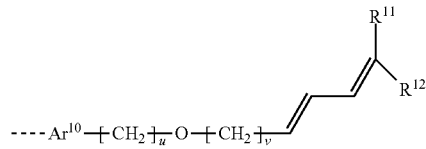

Q17

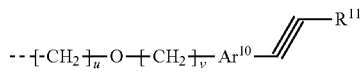

Q18

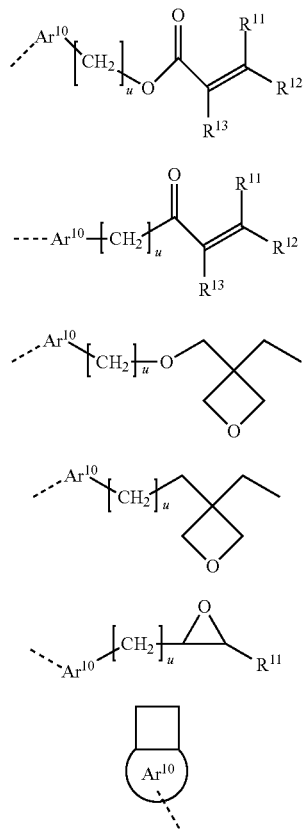

where the dashed bond in the formulae Q1 to Q11, Q13 to Q24 and the dashed bonds in the formula Q12 represent the linking of the crosslinkable group to; the adjacent phenyl group of the formula (2) or (3); and where $R^{11}$, $R^{12}$ and $R^{13}$ are on each occurrence, identically or differently, H, a straight-chain or branched alkyl group having 1 to 6 C atoms;

$Ar^{10}$ is on each occurrence, in each case identically or differently, a mono- or polycyclic, aromatic or heteroaromatic ring system having 5 to 60 aromatic ring atoms, which may be substituted by one or more radicals R, where R is as defined in claim 1;

u is an integer from 0 to 8; and v is an integer from 1 to 8.

5. The compound according to claim 1, where $Ar^3$, $Ar^4$ and $Ar^5$ are selected on each occurrence, identically or differently, from the group consisting of an aromatic or heteroaromatic ring system having 5 to 30 aromatic ring atoms, which may be substituted by one or more radicals R.

6. The compound according to claim 1, where $Ar^3$, $Ar^4$ and $Ar^5$ are selected on each occurrence, identically or differently, from the group consisting of benzene, naphthalene, anthracene, biphenyl, terphenyl, quaterphenyl, fluorene, dibenzofuran, dibenzothiophene, carbazole, indolocarbazole, indenocarbazole, pyridine, quinoline, isoquinoline, pyridazine, benzopyridazine, pyrimidine, benzopyrimidine, quinoxaline, pyrazine, azacarbazole, benzocarboline, 1,3,5-triazine, 1,2,4-triazine, 1,2,3-triazine, each of which may be substituted by one or more radicals R.

7. The compound according to claim 1, where m is equal to 1 and n is equal to 1.

8. The compound according to claim 1, where m is equal to 1.

9. A formulation comprising at least one compound according to claim 1 and at least one solvent.

10. An electronic device comprising at least one compound according to claim 1 selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

11. An organic electroluminescent device comprising a compound according to claim 1 wherein the compound is used in a hole-transport layer or in a hole-injection layer, where this layer may also be doped.

12. The compound according to claim 1, where $Ar^3$ and $Ar^5$ are selected on each occurrence, identically or differently, from the groups of the following formulae (A-1) to (A-51),

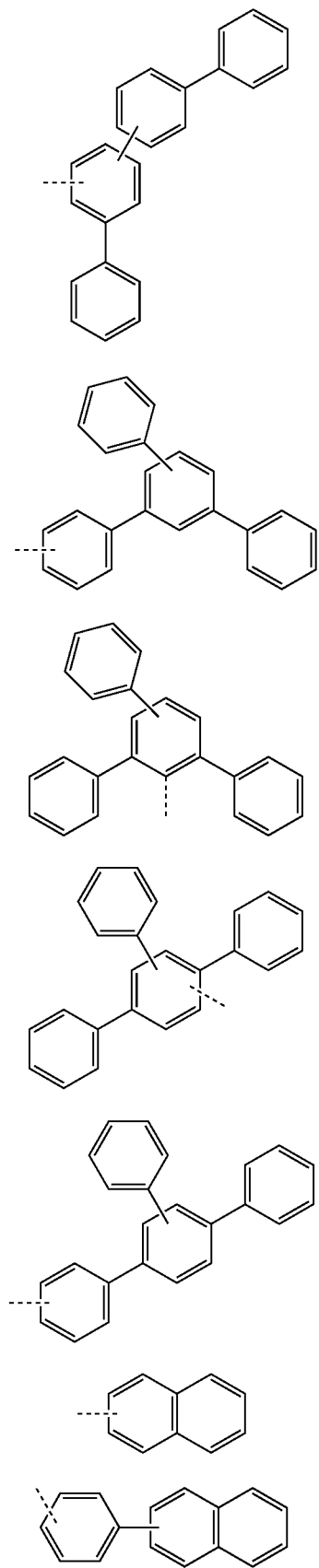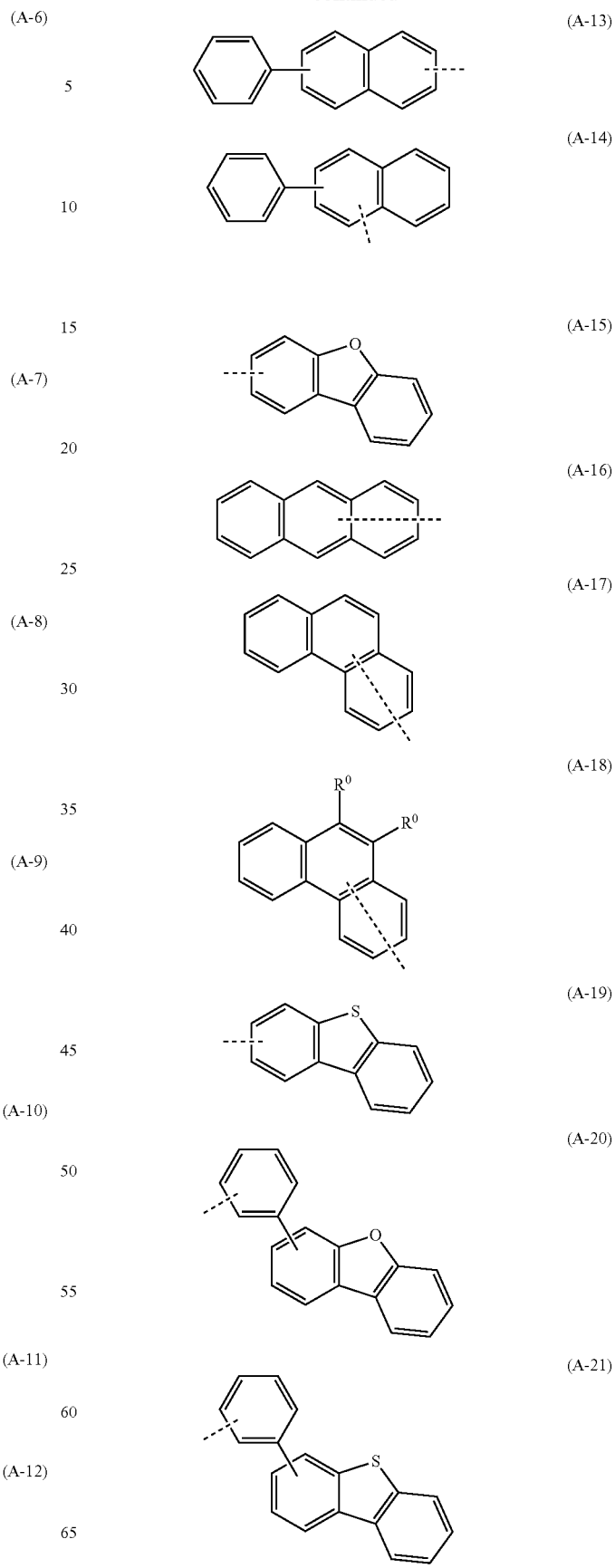

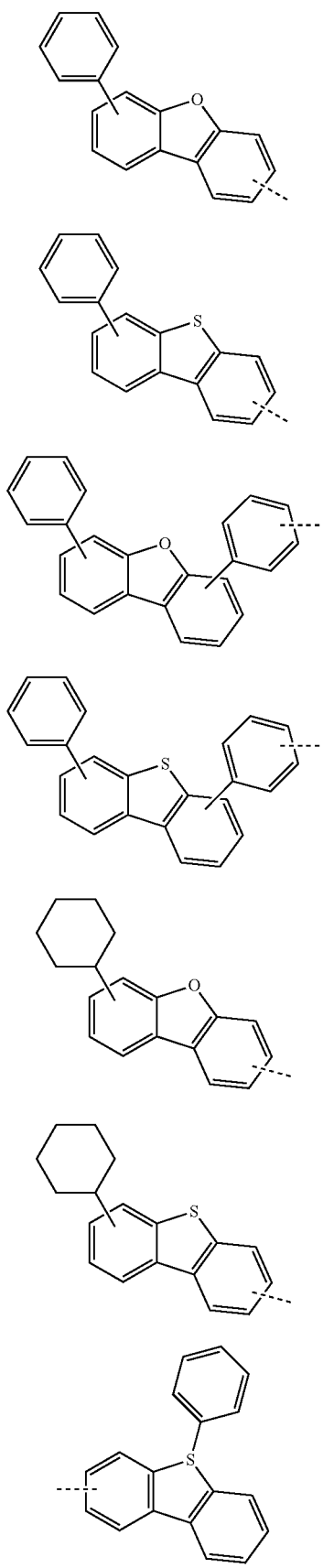
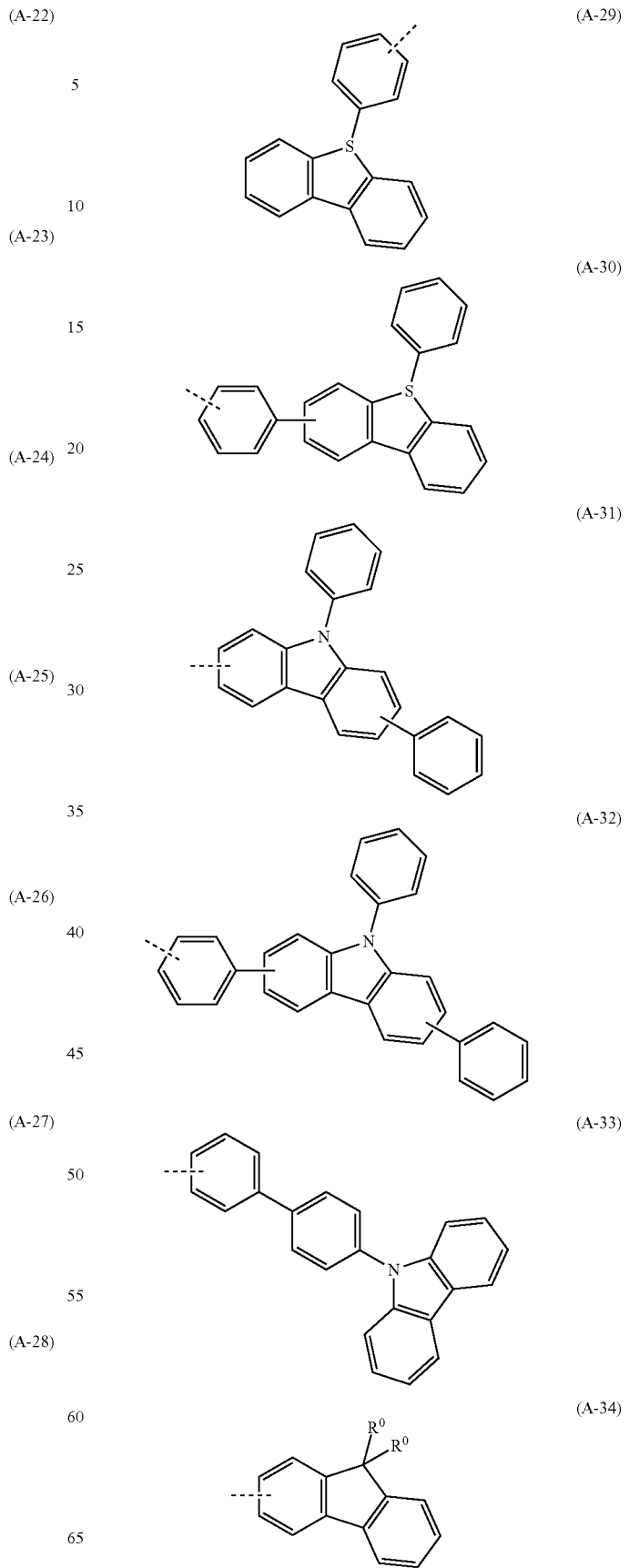

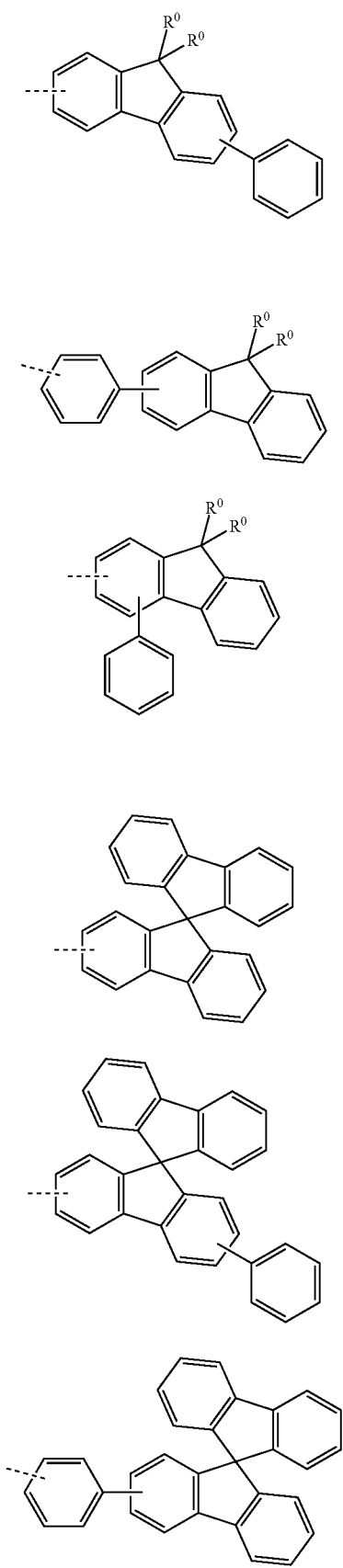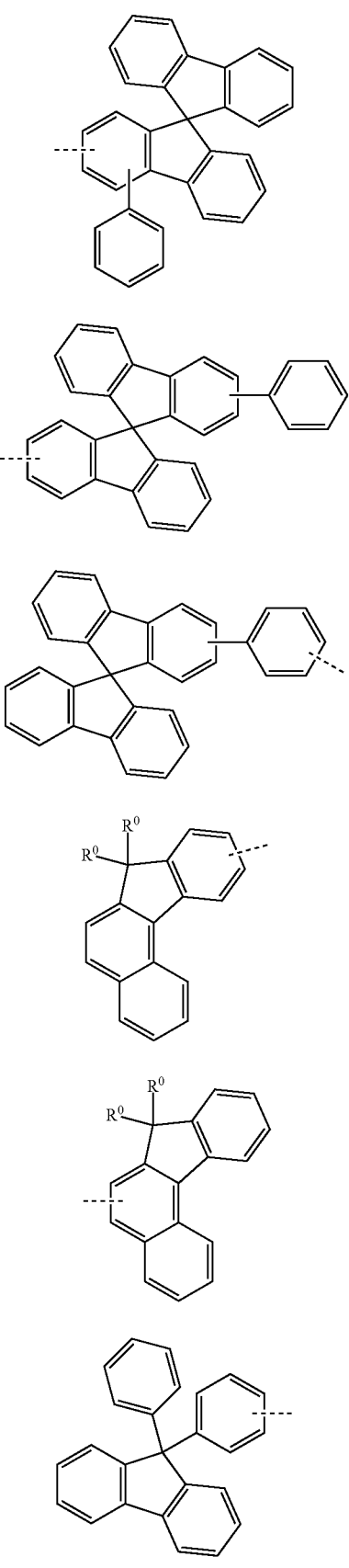

-continued

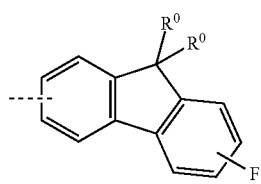 (A-47)

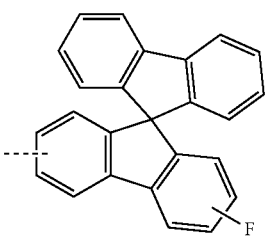 (A-48)

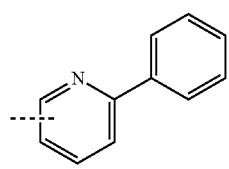 (A-49)

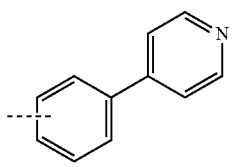 (A-50)

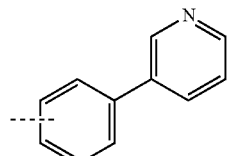 (A-51)

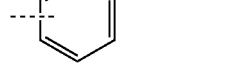

where the dashed bond indicates the bond to the nitrogen atom, where the groups of formulae (A-1) to (A-51) may further be substituted at each free position by a group R as defined in claim 1, and where $R^0$, in formulae (A-18), (A-34) to (A-37), (A-44), (A-45) and (A-47), is selected on each occurrence, identically or differently, from the group consisting of H, D, F, CN, $Si(R^3)_3$, a straight-chain alkyl group having 1 to 20 C atoms or a branched or cyclic alkyl group having 3 to 20 C atoms, each of which may be substituted by one or more radicals $R^1$, an aromatic or heteroaromatic ring system having 5 to 18 aromatic ring atoms, which may in each case be substituted by one or more radicals $R^1$, where two adjacent substituents $R^0$ may optionally form a mono- or polycyclic, aliphatic ring system or aromatic ring system, which may be substituted by one or more radicals $R^1$.

13. The compound according to claim 12, where $Ar^4$ is on each occurrence, identically or differently, selected from the groups of the following formulae (B-1) to (B-24),

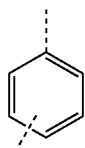 B-1

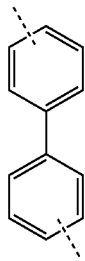 B-2

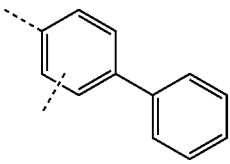 B-3

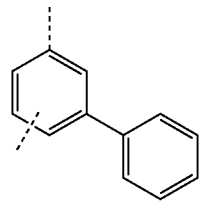 B-4

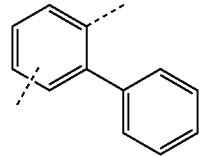 B-5

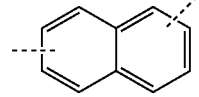 B-6

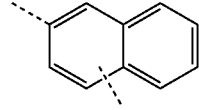 B-7

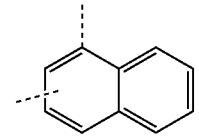 B-8

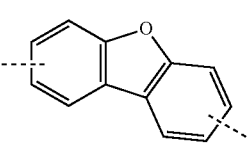 B-9

-continued
B-10
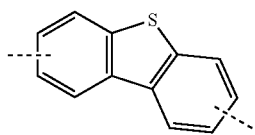
B-11
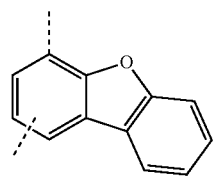
B-12
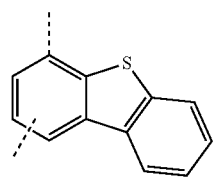
B-13
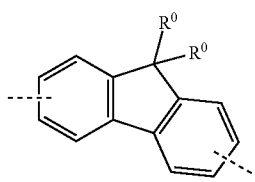
B-14
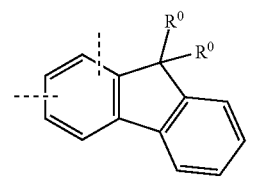
B-15
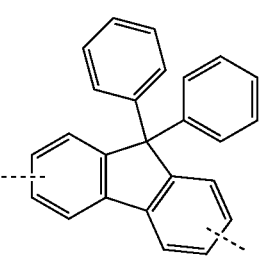
B-16
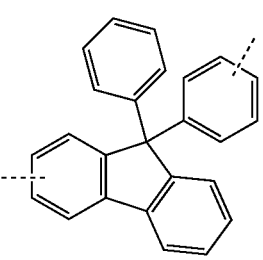
-continued
B-17
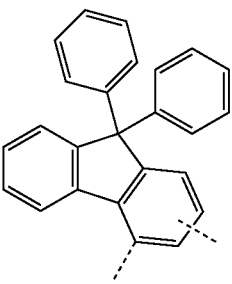
B-18
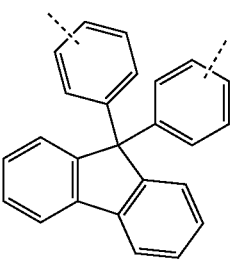
B-19
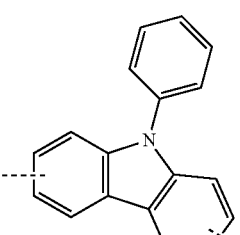
B-20
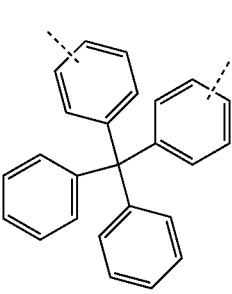
B-21
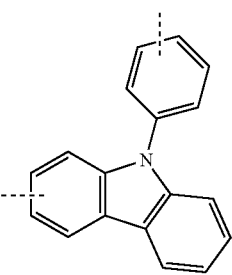
B-22
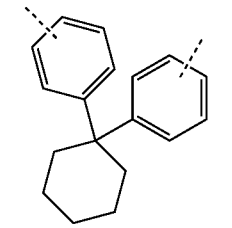

-continued

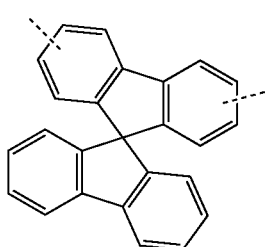

B-23

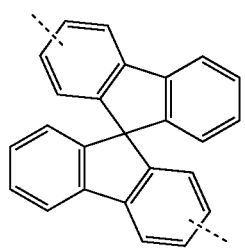

B-24 where the dashed bonds in (B-1) to (B-24) indicate the bonds to the nitrogen atoms of the arylamino groups depicted in formula (2) or (3);

where the groups of formulae (B-1) to (B-24) may further be substituted at each free position by a group R, wherein R is on each occurrence, identically or differently, H, D, F, Cl, Br, I, CHO, $N(Ar)_2$, $C(=O)Ar$, $P(=O)(Ar)_2$, $S(=O)Ar$, $S(=O)_2Ar$, $(R)C=C(R)Ar$, CN, $NO_2$, $Si(R^1)_3$, $B(OR^1)_2$, $B(R^1)_2$, $B(N(R^1)_2)_2$, $OSO_2R^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^1$, where one or more, non-adjacent $CH_2$ groups may be replaced by $(R^1)C=C(R^1)$, $C\equiv C$, $Si(R^1)_2$, $Ge(R^1)_2$, $Sn(R^1)_2$, $C=O$, $C=S$, $C=Se$, $P(=O)(R^1)$, SO, $SO_2$, $N(R^1)$, O, S or $CON(R^1)$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may be substituted by one or more radicals $R^1$, where optionally two adjacent substituents R can form a mono- or polycyclic, aliphatic, aromatic or heteroaromatic ring system with one another;

Ar is an aromatic or heteroaromatic ring system having 5 to 60 aromatic ring atoms, which may be substituted by one or more radicals $R^1$;

$R^1$ is on each occurrence, identically or differently, H, D, F, Cl, Br, I, CHO, $N(R^2)_2$, $C(=O)R^2$, $P(=O)(R^2)_2$, $S(=O)R^2$, $S(=O)_2R^2$, $(R^2)C=C(R^2)_2$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more, non-adjacent $CH_2$ groups may be replaced by $(R^2)C=C(R^2)$, $C\equiv C$, $Si(R^2)_2$, $Ge(R^2)_2$, $Sn(R^2)_2$, $C=O$, $C=S$, $C=Se$, $P(=O)(R^2)$, SO, $SO_2$, $N(R^2)$, O, S or $CON(R^2)$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, where optionally two adjacent substituents $R^1$ can form a mono- or polycyclic, aliphatic, aromatic or heteroaromatic ring system with one another;

$R^2$ is on each occurrence, identically or differently, H, D, F, Cl, Br, I, CHO, CN, $NO_2$, a straight-chain alkyl, alkoxy or thioalkoxy group having 1 to 20 C atoms or a straight-chain alkenyl or alkynyl group having 2 to 20 C atoms or a branched or cyclic alkyl, alkenyl, alkynyl, alkoxy or thioalkoxy group having 3 to 20 C atoms, or an aromatic or heteroaromatic ring system having 5 to 30 aromatic ring atoms or an aryloxy or heteroaryloxy group having 5 to 30 aromatic ring atoms; where optionally two adjacent substituents $R^2$ can form a mono- or polycyclic, aliphatic, aromatic or heteroaromatic ring system with one another;

and where $R^0$ has the same meaning as in claim 12.

\* \* \* \* \*